US012708673B2

(12) United States Patent
Ruoslahti et al.

(10) Patent No.: US 12,708,673 B2
(45) **Date of Patent: *Aug. 18, 2026**

(54) METHODS AND COMPOSITIONS RELATED TO PEPTIDES AND PROTEINS WITH C-TERMINAL ELEMENTS

(71) Applicant: Sanford Burnham Prebys Medical Discovery Institute, La Jolla, CA (US)

(72) Inventors: Erkki Ruoslahti, La Jolla, CA (US); Tambet Teesalu, La Jolla, CA (US); Kazuki Sugahara, La Jolla, CA (US)

(73) Assignee: Sanford Burnham Prebys Medical Discovery Institute, La Jolla, CA (US)

( * ) Notice: Subject to any disclaimer, the term of this patent is extended or adjusted under 35 U.S.C. 154(b) by 81 days.

This patent is subject to a terminal disclaimer.

(21) Appl. No.: 17/681,380

(22) Filed: Feb. 25, 2022

(65) Prior Publication Data

US 2023/0173097 A1 Jun. 8, 2023

Related U.S. Application Data

(63) Continuation of application No. 12/390,061, filed on Feb. 20, 2009, now Pat. No. 11,260,133.

(60) Provisional application No. 61/030,409, filed on Feb. 21, 2008.

(51) Int. Cl.
*A61K 47/69* (2017.01)
*A61K 47/62* (2017.01)
*A61K 47/64* (2017.01)

(52) U.S. Cl.
CPC .......... *A61K 47/6923* (2017.08); *A61K 47/62* (2017.08); *A61K 47/64* (2017.08)

(58) Field of Classification Search
None
See application file for complete search history.

(56) References Cited

U.S. PATENT DOCUMENTS

| | | | |
|---|---|---|---|
| 5,262,176 | A | 11/1993 | Palmacci |
| 5,662,885 | A | 9/1997 | Pollak |
| 6,177,542 | B1 | 1/2001 | Ruoslahti |
| 6,530,944 | B2 | 3/2003 | West |
| 6,576,239 | B1 | 6/2003 | Ruoslahti |
| 6,967,238 | B2 | 11/2005 | Blaschuk |
| 7,034,109 | B2 | 4/2006 | Bonny |
| 7,063,847 | B1 | 6/2006 | Sanderson |
| 7,544,767 | B2 | 6/2009 | Ruoslahti |
| 10,500,246 | B2 | 12/2019 | Ruoslahti et al. |
| 2001/0002150 | A1 | 5/2001 | Frigo |
| 2002/0055174 | A1 | 5/2002 | Rittner |
| 2002/0068272 | A1 | 6/2002 | Larocca |
| 2002/0132990 | A1 | 9/2002 | Huston |
| 2002/0193295 | A1 | 12/2002 | Calenoff |
| 2003/0003100 | A1 | 1/2003 | Levy |
| 2003/0077289 | A1 | 4/2003 | Wang |
| 2003/0082143 | A1 | 5/2003 | Larocca |
| 2003/0082176 | A1 | 5/2003 | Lebowitz |
| 2003/0083261 | A1 | 5/2003 | Yu |
| 2003/0125283 | A1 | 7/2003 | Gatenby |
| 2003/0148263 | A1 | 8/2003 | Larocca |
| 2003/0166601 | A1 | 9/2003 | Woodle |
| 2004/0005309 | A1 | 1/2004 | Lebowitz |
| 2004/0219169 | A1 | 11/2004 | Bermudes |
| 2005/0038239 | A1 | 2/2005 | Catchpole |
| 2005/0054563 | A1 | 3/2005 | Desnoyer |
| 2005/0071088 | A1 | 3/2005 | Landfield |
| 2005/0085417 | A1 | 4/2005 | Wickstrom |
| 2005/0147993 | A1 | 7/2005 | Khan |
| 2005/0233356 | A1 | 10/2005 | Jones |
| 2005/0260756 | A1 | 11/2005 | Troy |
| 2005/0281805 | A1 | 12/2005 | Lebowitz |
| 2006/0014712 | A1 | 1/2006 | Neuman |
| 2006/0051315 | A1 | 3/2006 | Scaria |
| 2006/0070133 | A1 | 3/2006 | Dean |
| 2006/0100134 | A1 | 5/2006 | Guo |
| 2006/0147922 | A1 | 7/2006 | Watts |
| 2006/0147997 | A1 | 7/2006 | Ramakrishnan |
| 2006/0153775 | A1 | 7/2006 | Von Wronski |
| 2006/0154340 | A1 | 7/2006 | Louie |
| 2006/0160743 | A1 | 7/2006 | Zhang |
| 2006/0172941 | A1 | 8/2006 | Rastelli |
| 2006/0233807 | A1 | 10/2006 | Svanborg |

(Continued)

FOREIGN PATENT DOCUMENTS

| | | |
|---|---|---|
| EP | 0045665 | 2/1982 |
| JP | 2004512275 | 4/2004 |

(Continued)

OTHER PUBLICATIONS

Caveliers, et al., "Evaluation of 99mTc-RP128 as a potential inflammation imaging agent: human dosimetry and first clinical results", *J. Nucl. Med.*, 42:154-61 (2001).
Monsky, et al., "Augmentation of transvascular transport of macromolecules and nanoparticles in tumors using vascular endothelial growth factor", *Cancer Res.*, 59:4129-35 (1999).
Morishiita, et al., "A novel approach using functional peptides for efficient intestinal absorption of insulin", *J Contr. Rel*, 118:177-84 (2007).
Ruoslahti, et al., "Vascular homing peptides with cell-penetrating properties", *Curr. Pharm. Des.*, 11(28):3655-60 (2005).
Von Wronski, et al., "Tuftsin binds neuropilin-1 through a sequence similar to that encoded by exon 8 of vascular endothelial growth factor", *JBC*, 281:5702-10 (2006).

(Continued)

*Primary Examiner* — Tara L Martinez
(74) *Attorney, Agent, or Firm* — PABST PATENT GROUP LLP

(57) ABSTRACT

Disclosed are compositions and methods useful for targeting and internalizing molecules into cells of interest and for penetration by molecules of tissues of interest. The compositions and methods are based on peptide sequences that are selectively internalized by a cell, penetrate tissue, or both. The disclosed internalization and tissue penetration is useful for delivering therapeutic and detectable agents to cells and tissues of interest.

20 Claims, 28 Drawing Sheets

Specification includes a Sequence Listing.

(56) References Cited

U.S. PATENT DOCUMENTS

| | | | |
|---|---|---|---|
| 2006/0239968 | A1 | 10/2006 | Arap |
| 2006/0242725 | A1 | 10/2006 | Strong |
| 2006/0257942 | A1 | 11/2006 | Waldo |
| 2007/0041904 | A1 | 2/2007 | Jiang |
| 2007/0111251 | A1 | 5/2007 | Rosania |
| 2007/0111270 | A1 | 5/2007 | Zhang |
| 2007/0157328 | A1 | 7/2007 | Ramrakha |
| 2007/0212332 | A1 | 9/2007 | Baylink |
| 2007/0231862 | A1 | 10/2007 | Diamond |
| 2007/0287680 | A1 | 12/2007 | Cuchelkar |
| 2007/0292920 | A1 | 12/2007 | Lin |
| 2007/0299043 | A1 | 12/2007 | Hunter |
| 2008/0014143 | A1 | 1/2008 | Ruoslahti |
| 2008/0234183 | A1 | 9/2008 | Hallbrink |
| 2008/0305119 | A1 | 12/2008 | Dewhurst |
| 2008/0311136 | A1 | 12/2008 | Beusker |
| 2009/0031733 | A1 | 2/2009 | Weaver |
| 2009/0087899 | A1 | 4/2009 | McKnight |
| 2009/0092548 | A1 | 4/2009 | Ferrara |
| 2009/0176660 | A1 | 7/2009 | Yla-Herttuala |
| 2009/0176710 | A1 | 7/2009 | Hadwiger |
| 2009/0186802 | A1 | 7/2009 | Alluis |
| 2009/0226372 | A1 | 9/2009 | Ruoslahti |
| 2009/0246133 | A1 | 10/2009 | Ruoslahti |
| 2009/0257951 | A1 | 10/2009 | Ruoslahti |
| 2009/0258926 | A1 | 10/2009 | Divita |
| 2009/0280058 | A1 | 11/2009 | Troy |
| 2009/0305329 | A1 | 12/2009 | Szilak |
| 2009/0317802 | A1 | 12/2009 | Bhatia |
| 2009/0325866 | A1 | 12/2009 | Kim |
| 2010/0016215 | A1 | 1/2010 | Moulton |
| 2010/0022466 | A1 | 1/2010 | Raucher |
| 2010/0048487 | A1 | 2/2010 | Uno |
| 2010/0061932 | A1 | 3/2010 | Brock |
| 2010/0061942 | A1 | 3/2010 | Ma |
| 2010/0099627 | A1 | 4/2010 | Seger |
| 2010/0143454 | A1 | 6/2010 | Mclinden |
| 2010/0172835 | A1 | 7/2010 | Ruoslahti |
| 2010/0279918 | A1 | 11/2010 | Langel |
| 2026/0048133 | A1 | 2/2026 | Ruoslahti et al. |

FOREIGN PATENT DOCUMENTS

| | | | |
|---|---|---|---|
| JP | 2006257074 | | 9/2006 |
| JP | 2007511209 | | 5/2007 |
| WO | 1995022996 | | 8/1995 |
| WO | 2002018572 | | 3/2002 |
| WO | 0231109 | | 4/2002 |
| WO | WO2003-106491 | * | 6/2003 |
| WO | 03106491 | | 12/2003 |
| WO | 2004074432 | | 9/2004 |
| WO | 2005042034 | | 5/2005 |
| WO | 2006096207 | | 9/2006 |
| WO | 2007014391 | | 1/2007 |
| WO | 2007090194 | | 8/2007 |
| WO | 2007108749 | | 9/2007 |
| WO | 2009036092 | | 3/2009 |
| WO | 2009105671 | | 8/2009 |
| WO | 2009126349 | | 10/2009 |
| WO | 2010075540 | | 7/2010 |

OTHER PUBLICATIONS

Abi-Habib, et al., "A urokinase-activated recombinant diphtheria toxin targeting the granulocyte-macrophage colony-stimulating factor receptor is selectively cytotoxic to human acute myeloid leukemia blasts", Blood, 104: 2143-8(2004).

Acevedo, et al., "Semaphorin 3A suppresses VEGF-mediated angiogenesis yet acts as a vascular permeability factor", Blood , 111:2674-80 (2008).

Allam, et al., "Cholera toxin triggers apoptosis in human lung cancer cell lines", Cancer Res., 57:2615-2618 (1997).

Almquist, et al., "Synthesis and biological activity of a ketomethylene analogue of a tripeptide inhibitor of angiotensin converting enzyme", J. Med. Chem., 23:1392-8 (1980).

Altin and Pagler, "A one-step procedure for biotinylation and chemical cross-linking of lymphocyte surface and intracellular membrane-associated molecules", Anal Biochem., 224: 382-9(1995).

Andreasen, "The plasminogen activation system in tumor growth, invasion, and metastasis", Cell. Mol. Life Sci., 57:25-40 (2000).

Arap, et al., "Cancer treatment by targeted drug delivery to tumor vasculature in a mouse model", Science 279:377-380 (1998).

Arap, et al., "Targeting the prostate for destruction through a vascular address", PNAS, 99:1527-1531 (2002).

Arbeit, et al., "Progressive squamous epithelial neoplasia in K14-human papillomavirus type 16 transgenic mice", J Virol., 68:4358-68 (1994).

Arleth, et al., "Detailed structure of hairy mixed micelles formed by phosphatidylcholine and PEGylated phospholipids in aqueous media", Langmuir, 21:3279-90 (2005).

Assa-Munt, et al., "Solution structures and integrin binding activities of an RGD peptide with two isomers", Biochemistry, 40:2373-8 (2001).

Bardeesy, et al., " Pancreatic cancer biology and genetics", Nature Rev Cancer, 2:897-909, 2002).

Bartlett, et al., "Impact of tumor-specific targeting on the biodistribution and efficacy of siRNA nanoparticles measured by multimodality in vivo imaging", PNAS, 104:15549-54 (2007).

Benner, "Expanding the genetic lexicon: incorporating non-standard amino acids into proteins by ribosome-based synthesis", TIB Tech, 12:158-63 (1994).

Berg, et al., "Physiological functions of endosomal proteolysis", Biochem. J., 307: 313-26 (1995).

Biacchesi, et al., "Modification of the trypsin-dependent cleavage activation site of the human metapneumovirus fusion protein to be trypsin independent does not increase replication or spread in rodents or nonhuman primates", J. Virol., 80:5798-5806 (2006).

Biology Online, accessed Dec. 23, 2016.

Blasi and Carmeliet, "uPAR: a versatile signalling orchestrator", Nat Rev Mol Cell Biol., 3:932-43 (2002).

Brewis, et al., "Particle assembly incorporating a VP22-BH3 fusion protein, facilitating intracellular delivery, regulated release, and apoptosis", Mol. Ther., 7:262-70 (2003).

Brooks, et al., "Integrin alpha v beta 3 antagonists promote tumor regression by inducing apoptosis of angiogenic blood vessels", Cell, 79:1157-64 (1994).

Brown and Ruoslahti, "Metadherin, a cell-surface protein in breast tumors that mediates lung metastasis", Cancer Cell, 5:365-374 (2004).

Cahill, et al., "Site specific mutagenesis with unnatural amino acids", TIBS, 14(10):400-3 (1989).

Chambers, et al., "Flavivirus genome organization, expression, and replication", Annu. Rev. Microbiol., 44:649-88 (1990).

Cheresh, et al., "Biosynthetic and functional properties of an Arg-Gly-Asp-directed receptor involved in human melanoma cell attachment to vitronectin, fibrinogen, and von Willebrand factor", J Biol Chem., 262:17703-17710 (1987).

Christian, et al., "Nucleolin expressed at the cell surface is a marker of endothelial cells in tumor blood vessels", J Cell Biol. 163:871-8 (2003).

Conese, et al., "alpha-2 Macroglobulin receptor/Ldl receptor-related protein(Lrp)-dependent internalization of the urokinase receptor", J Cell Biol., 131:1609-22 (1995).

Curnis, et al., "Coupling tumor necrosis factor-a with av integrin ligands improves its antineoplastic activity", Cancer Res. 64:565-571 (2004).

Debele, et al., "Specificity profiling of seven human tissue kallikreins reveals individual subsite preferences", J Biol Chem., 281: 25678-88 (2006).

Derfus, et al., "Targeted Quantum Dot Conjugates for siRNA Delivery", Bioconjug Chem, 18: 1391-6 (2007).

Derossi, et al., "Trojan peptides: the penetratin system for intracellular delivery", Trends Cell Biol., 8:84-7 (1998).

Dharap, et al., "Targeted proapoptotic LHRH-BH3 peptide", Pharm Res., 20:889-96 (2003).

(56) References Cited

OTHER PUBLICATIONS

Drake, et al., "Assessing tumor growth and distribution in a model of prostate cancer metastasis using bioluminescence imaging", Clin Exp Metastasis, 22:674-684 (2005).
Duckert, et al., "Prediction of proprotein convertase cleavage sites", Protein Eng. Design & Selection, 17(1):107-12 (2004).
Dykxhoorn, et al., "The silent treatment: siRNAs as small molecule drugs", Gene Ther. 13:541-52 (2006).
Elango, et al., "The mumps virus fusion protein mRNA sequence and homology among the paramyxoviridae proteins", J. Gen. Virol. 70:801-807 (1989).
Eliceiri and Cheresh, "Adhesion events in angiogenesis", Curr Opin Cell Biol 13:563-68 (2001).
Elliott and O'Hare, "Intercellular trafficking and protein delivery by a herpesvirus structural protein", Cell, 88:223-33 (1997).
Esmon, et al., "Cell mediated events that control blood coagulation and vascular injury", Annu. Rev. Cell. Biol., 9:1-26 (1993).
Falanga, et al. "Wound bed score and its correlation with healing of chronic wounds", Dermatol Ther 19:383-90 (2006).
Fenart and Cecchelli, "Protein transport in cerebral endothelium. In vitro transcytosis of transferring", Meth. Mol. Med., 89:277-90 (2003).
Fogal, et al., "Mitochondrial/ Cell surface protein p32/gC1qR as a molecular target in tumor cells and tumor stroma", Cancer Res., 68:7210-18 (2008).
Folkman, "Angiogenesis", Annu Rev Med. 57:1-18, (2006).
Fujikawa, et al., "Activation of bovine factor X (Stuart factor): conversion of factor Xa alpha to factor Xa beta", PNAS, 72:3359-63 (1975).
Gammon, et al., "Quantitative Analysis of Permeation Peptide Complexes Labeled with Technetium-99m: Chiral and Sequence-Specific Effects on Net Cell Uptake", Bioconjugate Chem., 14:368-76 (2003).
GenBank Accession No. Q1YF93 "CueR-like heavy metal response, transcription regulator", 1 page, Submitted Mar. 2006, first published May 2, 2006, accessed Aug. 24, 2011.
Geretti, et al., "Neuropilin structure governs VEGF and semaphorin binding and regulates angiogenesis", Angiogenesis, 11:31-39 (2008).
Gonzalez-Reyes, et al., "Cleavage of the human respiratory syncytial virus fusion protein at two distinct sites is required for activation of membrane fusion", PNAS, 98:9859-64 (2001).
Goodman and Ro, "Peptidomimetics for Drug Design", Buerger's Medicinal Chemistry Drug Discovery vol. 1 (ed M.E. Wolff; John Wiley & Sons, pp. 803-861 (1995).
Gordon, et al., "Proteolytic activation of bacterial toxins by eukaryotic cells is performed by furin and by additional cellular proteases", Infec. Immun. 63:82-7(1995).
Grabitz, et al., "Science with no fiction: measuring the veracity of scientific reports by citation analysis", 1-9, bioRxiv.org., Preprint Article (2017).
Grebrehiwet, et al., "gC1q-R/p33: structure-function predictions from the crystal structure", Immunobiology, 205:421-32 (2002).
Green, et al., "Autonomous functional domains of chemically synthesized human immunodeficiency virus tat trans-activator protein", Cell, 55:1179-88 (1988).
Hagedorn and Bikfalvi, "Target molecules for anti-angiogenic therapy: from basic research to clinical trials", Crit. Rev. Oncol. Hematol. 34:89-110 (2000).
Hambley and Hait,"Is Anticancer Drug Development Heading in the Right Direction?" Cancer Res., 69:1259-62 (2009).
Hamzah, et al., "Vascular Targeting of Anti-CD40/IL2 into Autochthonous Tumors Enhances Immunotherapy", J. Clin. Invest., 118:1691-99 (2008).
Hanahan, "Heritable formation of pancreatic-cell tumors in transgenic mice expressing recombinant insulin/simian virus 40 oncogenes", Nature, 315:115-22 (1985).
Hann, "On the double bond isostere of the peptide bond: preparation of an enkephalin analogue", J. Chem. Soc Perkin Trans., 1: 307-14 (1982).
Hansen, et al., "A urokinase-type plasminogen activator-inhibiting cyclic peptide with an unusuall P2 residue and an extended protease binding surface demonstrates new modalities for enzyme inhibition", J Biol Chem., 280:38242-37 (2005).
Heldin, et al., "High interstitial fluid pressure—an obstacle in cancer therapy", Nat Rev Cancer 4:806-13 (2004).
Hezel, et al., "Genetics and biology of pancreatic ductal adenocarcinoma", Genes Dev, 20:1218-49 (2006).
Hoffman, et al., "In vivo and ex vivo selections using phage-displayed libraries", Phage Display: A Practical Approach, T. Clarkson and H. Lowman, eds. (Oxford, U.K.: Oxford University Press), Chap 10:171(2004).
Hoffman, et al., "Progressive vascular changes in a transgenic mouse model of squamous cell carcinoma", Cancer Cell, 4:383-91 (2003).
Holladay, et al., "Synthesis of hydroxyethylene and ketomethylene dipeptide isosteres", Tetrahedron Lett, 24:4401-4 (1983).
Hong, et al., "Targeting neuropilin 1 as an antitumor strategy in lung cancer", Clinical. Cancer Res., 13(6): 4759-68 (2007).
Hooper, et al., "Membrane protein secretases", Biochem. J. 321:265-279 (1997).
Horswill, et al., "Cyclic Peptides, a Chemical Genetics Tool for Biologists", Cell Cycle, 4(4):552-555 (2005).
Hruby, "Conformational restrictions of biologically active peptides via amino acid side chain groups", Life Sci., 31:189-99 (1982).
Hudson, et al., "Methionine enkephalin and isosteric analogues. I. Synthesis on a phenolic resin support". Int J Pept Prot Res., 14:177-85 (1979).
Ibba and Hennecke, "Towards engineering proteins by site-directed incorporation in vivo of non-natural amino acids", Biotechnology, 12:678-82 (1994).
Ibba, "Strategies for in vitro and in vivo translation with non-natural amino acids", Biotechnology and & Genetic Engineering Reviews, 13:197-216 (1995).
International Preliminary Report on Patentability and Written Opinion for PCT/US2009/031305 dated (Jul. 20, 2010).
International Search Report and Written Opinion for application PCT/US09/34713 dated Aug. 4, 2009.
International Search Report PCT application PCT/US2010/039539 dated Oct. 25, 2010.
International Search Report PCT/US2009/031305, mailed Mar. 10, 2010.
Jain, "Normalization of tumor vasculature: An emerging concept in antiangiogenic therapy", Science, 307:58-62 (2005).
Jain, "Vascular and interstitial barriers to delivery of therapeutic agents in tumors", Cancer Metastasis Rev, 9:253-266 (1990).
Jain, et al., "Effect of vascular normalization by antiangiogenic therapy on interstitial hypertension, peritumor edema, and lymphatic metastasis: insights from a mathematical model", Cancer Res., 67:2729-35 (2007).
Jarvinen and Ruoslahti, "Molecular changes in the vasculature of injured tissues", Am. J. Path., 171:702-711 (2007).
Jennings-White, et al., "Synthesis of ketomethylene analogs of dipeptides", Tetrahedron Lett., 23:2533 (1982).
Jia, et al., "Characterization of a bicyclic peptide neuropilin-1 (NP-1) antagonist (EG3287) reveals importance of vascular endothelial growth factor exon 8 for NP-1 binding and role of NP-1 in KDR signaling", J. Biol. Chem., 281:13493-502 (2006).
Jia, et al., "Cysteine-rich and basic domain HIV-1 Tat peptides inhibit angiogenesis and induce endothelial cell apoptosis", Biochem. Biophys. Res. Commun., 283:469-79 (2001).
Jiang, et al., Tumor imagining by means of proteolytic activation of cell-openetrating peptides, PNAS, 101:17867-72 (2004).
Johannsen, et al., "Proteins of purified Epstein-Barr virus", PNAS, 101:16286-91 (2004).
Joliot, et al., "Antenapedia homeobox peptide regulates neural morphogenesis", PNAS, 88:1864-68 (1991).
Joyce, et al., "Stage-specific vascular markers revealed by phage display in a mouse model of pancreatic islet tumorigenesis", Cancer Cell, 4:393-403 (2003).
Kamei, et al., "Importance of intermolecular interaction on the improvement of intestinal therapeutic peptide/protein absorption using cell-penetrating peptides", J Contr. Rel., 136:179-86 (2009).

(56) References Cited

OTHER PUBLICATIONS

Kamei, et al., "Usefulness of cell-penetrating peptides to improve intestinal insulin absorption.", J Contr. Rel., 132:21-5 (2008).
Kandela, et al., "Registered report: Coadministration of a tumor-penetrating peptide enhances the efficacy of cancer drugs", eLife. 10.7554/eLife.06959, includes opublished correction (2015).
Karmali, et al., "Targeting of albumin-embedded paclitaxel nanoparticles to tumors", Nanomedicine, 5:73-82 (2009).
Ke, et al., "Optimal subsite occupancy and design of selective inhibitor of urokinase", J. Biol. Chem., 272:20456-62 (1997).
Kerbel, et al., "The anti-angiogenic basis of metronomic chemotherapy", Nat Rev Cancer, 4: 423-36 (2004).
Kirsch, et al., "Anti-angiogenic treatment strategies for malignant brain tumors", J. Neurooncol., 50:149-63 (2000).
Klenk, et al., "Host cell proteases controlling virus pathogenicity", Trends Microbiol, 2:39-43 (1994).
Koga, et al., "Nucleotide Sequence and Expression of the Feline Vascular Endothelial Growth Factor", J. Vet. Med. Sci., 64(5):453-456 (2002).
Koivunen, et al., "Phage libraries displaying cyclic peptides with different ring sizes: ligand specificities of the RGD-directed integrins", Biotechnology, 13:265-70 (1995).
Koivunen, et al., "Selection of peptides binding to the alpha 5 beta 1 integrin from phage display library", J Biol Chem, 268:20205-10 (1993).
Kolonin, et al., "Synchronous selection of homing peptides for multiple tissues by in vivo phage display", FASEB, 20:979-81 (2006).
Koya, et a., "Nucleotide sequence and expression of the feline vascular endothelial growth factor", J Vet Med Sci., 64(5):453-6 (2002).
Kreitman and Pastan, "Recombinant toxins containing human granulocyte-macrophage colony-stimulating factor and either pseudomonas exotoxin or diphtheria toxin kill gastrointestinal cancer and leukemia cells", Blood, 90:252-9 (1997).
Kumar, et al., "Transvascular delivery of small interfering RNA to the central nervous system", Nature, 448:39-43 (2007).
Laakkonen, et al., "A tumor-homing peptide with a targeting specificity related to lymphatic vessels", Nature Med., 8:751-55 (2002b).
Laakkonen, et al., "Antitumor activity of a homing peptide that targets tumor lymphatics and tumor cells", PNAS, 101:9381-86 (2004).
Laakkonen, et al., "Peptide targeting of tumor lymph vessels", Ann NY Ac Sci., 1131:37-43 (2008).
Li and Huang "Surface-modified LPD nanoparticles for tumor targeting", Ann N.Y. Acad. Sci. 1082, 1-8 (2006).
Li, et al., "The role of the transferrin-transferrin-receptor system in drug delivery and targeting", Trends Pharmacol. Sci. 23, 206-209 (2002).
Liu, et al. "Targeting of tumor cells by cell surface urokinase plasminogen activator-dependent anthrax toxim", J Biol Chem. 276:17976-84 (2001).
Liu, et al., "In vivo biodistribution and highly efficient tumour targeting of carbon nanotubes in mice", Nat. Nanotech., 2:47-52 (2007).
Liu, et al., "In vivo interrogation of the molecular display of atherosclerotic lesion surfaces", American Journal of Pathology, 163:1859-71 (2003).
Liu, et al., "Prostate-specific Membrane Antigen Directed Selective Thrombotic Infarction of Tumors", Cancer Res., 62:5470-5 (2002).
Maeda, et al., "Vascular permeability enhancement in solid tumor: various factors, mechanisms involved and its implications", Int Immunopharmacol, 3:319-28 (2003).
Mantis, et al., "Replication Study: Coadministration of a tumor-penetrating peptide enhances the efficacy of cancer drugs", eLife, 10.7554/eLife.17584 (2017).
Marin, et al., "Role of vascular nitric oxide physiological and pathological conditions", Pharmacol Ther, 75:111-34 (1997).
Martin, et al., "Cancer gene therapy by thyroid hormone-mediated expression of toxin genes", Cancer Res., 60:3218-24 (2000).
Mayer, et al., "The role of tumor-associated macrophages in the delivery of liposomal doxorubicin to solid murine fibrosarcoma tumors", J Pharm. Exp Ther, 280:1406-14 (1997).
Meade and Dowdy, "Exogenous siRNA delivery using peptide transduction domains/cell penetrating peptides", Adv. Drug Delivery Reviews. 59(2-3):134-40 (2007).
Medarova, et al., "In vivo imaging of siRNA delivery and silencing in tumors",. Nat Med, 13: 372-7 (2007).
Miles and Miles, "Vascular reactions to histamine, histamine-liberator and leukotaxine in the skin of guinea-pigs", J Physiol, 118:228-57 (1952).
Minchinton and Tannock, "Drug penetration in solid tumours", Nat Rev Cancer 6:583-92 (2006).
Moghimi, et al., "Long-circulating and target-specific nanoparticles: Theory to practice", Pharm. Rev. 53:283-318 (2001).
Morley, "Modulation of the action of regulatory peptides by structural modification", Trends, Pharm Sci,. 463-468 (1980).
Moulard. and Decroly, "Maturation of HIV envelope glycoprotein precursors by cellular endoproteases", Biochim. Biophys. Acta, 1469:121-132 (2000).
Murakami and Etlinger, "Degradation of proteins with blocked amino groups by cytoplasmic proteases", Biochem. Biophys. Res. Comm., 146:1249-59 (1987).
Murohara, et al., "Vascular endothelial growth factor/vascular permeability factor enhances vascular permeability via nitric oxide and prostacyclin", Circ., 97:99-107 (1998).
Murphy, et al., "Nanoparticle-mediated drug delivery to tumor vasculature suppresses metastasis", PNAS, 105:9343-48 (2008).
Myrberg, et al., "Design of a Tumor-Homing Cell-Penetrating Peptide", Bioconjugate Chem., 19:70-75 (2008).
Nyberg, et al., "Trypsins and their role in carcinoma growth", Exp Cell Res., 312:1219-28 (2006).
Osborne and Coronado-Heisohn, "Targeting the epidermal growth factor receptor in breast cancer cell lines with a recombinant ligand fusion toxin (DAB389EGF)", Cancer J. Sci. Am. 2:175 (1996).
Park, et al., "Magnetic iron oxide nanoworms for tumor targeting and imaging",. Adv. Mater., 20:1630-5 (2008).
Park, et al., "Systematic surface engineering of magnetic nanoworms for in vivo tumor targeting", Small, 5:694-700 (2009).
Pasqualini, et al., "Alpha v integrins as receptors for tumor targeting by circulating ligands", Nature Biotechnol., 15:542-6 (1997).
Pellet-Many, et al., "Neuropilins: structure, function and role in disease", Biochem J, 411:211-26 (2008).
Pellinen, et al., "Integrin traffic", J Cell Sci 119:3723-31 (2006).
Pero, et al., "Combination treatment with Grb7 peptide and Doxorubicin or Trastuzumab (Herceptin) results in cooperative cell growth inhibition in breast cancer cells", British Journal of Cancer, 96(10):1520-1525 (2007).
Pierschbacher and Ruoslatli, "Cell attachment activity of fibronectin can be duplicated by small synthetic fragments of the molecule", Nature, 309:30-33 (1984).
Pilch, et al., "Peptides selected for binding to clotted plasma accumulate in tumor stroma and wonds", PNAS, 103:2800-4 (2006).
Pipkorn, et al. , "Delivery of substances and their target-specific topical activation", Biochim Biophys Acta, 1758(5):606-10 (2006).
Pirollo, et al., "Materializing the potential of small interfering RNA via a tumor-targeting nanodelivery system", Cancer Res., 67:2938-43 (2007).
Polyakov, et al., "Novel Tat-Peptide Chelates for Direct Transduction of Technetium-99m and Rhenium into Human Cells for Imaging and Radiotherapy". Bioconjugate Chem., 11:762-71 (2000).
Porkka, et al., "A fragment of the HMGN2 protein homes to the nuclei of tumor cells and tumor endothelial cells in vivo", PNAS, 99:7444-9 (2002).
Puente, et al., "Human and mouse proteases: a comparative genomic approach", Nat Rev Genet, 4:544-8 (2003).
Rajotte and Ruoshahti, "Membrane dipeptidase is the receptor for a lung-targeting peptide identified by in vivo phage display", J. Biol. Chem., 274:11593-11598 (1999).
Rajotte, et al., "Molecular heterogeneity of the vascular endothelium revealed by in vivo phage display", J Clin Invest., 102:430-7 (1998).

(56) References Cited

OTHER PUBLICATIONS

Rijken, “Plasminogen activators and plasminogen activator inhibitors: biochemical aspects”, Baillieres Clin Haematol., 8:291-312 (1995).
Rizo and Gierasch, “Constrained peptides: models of bioactive peptides and protein substructures”, Ann. Rev. Biochem., 61:387 (1992).
Rubinstein, et al., “Receptor for the globular heads of C1q (gC1q-R, p33, hyaluronan-binding protein) is preferentially expressed by adenocarcinoma cells”, Int J Cancer 100:741-50 (2004).
Ruiz-Linares, et al., “Processing of yellow fever virus polyprotein: role of cellular proteases in maturation of the structural proteins”, J. Virol., 63:4199-4209 (1989).
Ruoslahti and Rajotte, “An address system in the vasculature of normal tissues and tumors”, Annu. Rev. Immunol., 18:813-827 (2000).
Ruoslahti, “RGD story: a personal account. A Landmark Essay”, Matrix Biology 2:459-65 (2003).
Ruoslahti, “Specialization of tumour vasculature”, Nat. Rev. Cancer, 2:83-90 (2002).
Ruoslahti, et al., “Targeting of drugs and nanoparticles to tumors”, The Journal of Cell Biology, 188(6):759-768 (2010).
Ruoslahti,. “Drug targeting to specific vascular sites”, Drug Discovery Today. 7:1138-43 (2002).
Ruoslahti “Vascular zip codes in angiogenesis and metastasis”, Biochem. Soc. Transact., 32:397-402 (2004).
Rusnak, et al., “The effects of the novel, reversible epidermal growth factor receptor/ErbB-2 tyrosine kinase inhibitor, GW2016, on the growth of human normal and tumor-derived cell lines in vitro and in vivo”, Mol Cancer Ther., 1:85-94 (2001).
Sanchez, et al., “Crimean-congo hemorrhagic fever virus glycoprotein precursor is cleaved by Furin-like and SKI-1 proteases to generate a novel 38-kilodalton glycoprotein”, J. Virol., 80:514-25 (2006).
Sandgren, et al., “Nuclear targeting of macromolecular polyanious by an HIV—Tate derived peptide. Role for cell-surface proteoglycans”, J. Biol. Chem., 277:38877-83 (2002).
Sehgal, et al., “Photoinduced cytotoxicity and biodistribution of prostate cancer cell-targeted porphyrins”, J. Med. Chem, 51:6014-20 (2008).
Simberg, et al., “Biomimetic amplification of nanoparticle homing to tumors”, PNAS, 104:932-936 (2007).
Singer, et al., “Cutaneous wound healing”, NEJM, 341:738-46 (1999).
Sipkins, et al., “Detection of tumor angiogenesis in vivo by alphaVbeta3-targeted magnetic resonance imaging”, Nat. Med., 4:623-26 (1998).
Sjoberg, et al., “Furin cleavage potentiates the membrane fusion-controlling intersubunit disulfide bond isomerization activity of leukemia virus”, Env. J. Virol., 80:5540-51 (2006).
Smyth and Trapani, “Granzymes: exogenous proteinases that induce target cell apoptosis”, Immunology Today, 16: 202-206 (1995).
Soker, et al., “Neuropilin-1 is expressed by endothelial and tumor cells as an isoform-specific receptor for vascular endothelial growth factor”, Cell, 92:735-45 (1998).
Sokoloff, et al., “A new peptide ligand that targets particles and heterologous proteins to hepatocyctes in vivo”, Mol. Ther. 8:867-72 (2003).
Sokoloff, et al., “The interactions of peptides with the innate immune system studied with use of T7 phage peptide display”, Mol. Ther., 2:131-39 (2000).
Spatola, et al., “Structure-activity relationships of enkephalins containing serially replaced thiomethylene amide bond surrogates”, Life Sci 38:1243-9 (1986).
Spatola, “Peptide Backbone Modifications”, Chemistry and Biochemistry of Amino Acids, Pepides, and Proteins, B. Weinstein, eds., Marcel Dekker, New York, p. 267 (1983).
Spiridon, et al., “Targeting multiple Her-2 epitopes with monoclonal antibodies results in improved antigrowth activity of a human breast cancer cell line in vitro and in vivo”, Clin Cancer Res, 8:1720-30 (2002).
Starzec, et al., “Antiangiogenic and antitumor activities of peptide inhibiting the vascular endothelial growth factor binding to neuropilin-1”, Life Sci, 79:2370-81 (2006).
Steinhauer, “Role of hemagglutinin cleavage for the pathogenicity of influenza virus”, Virology, 258:1-20 (1999).
Sternlicht, et al., “How matrix metalloproteinases regulate cell behavior”, Annu. Rev. Cell. Dev. Biol., 17:463-513 (2001).
Sugahara, et al. “Coadministration of a tumor-penetrating peptide enhances the efficacy of cancer drugs”, Am. Assoc. Adv of Sci., 328(5981): 1031-35 (2010).
Sugahara, et al., “Chondroitin sulfate E fragments enhance CD44 cleavage and CD44 dependent motility in tumor cells”, Cancer Res., 68:7191-9 (2008).
Sugahara, et al., “Hyaluronan oligosaccharides induce CD44 cleavage and promote cell migration in CD44-expressing tumor cells”, J Biol Chem., 278:32259-65 (2003).
Sugahara, et al., “Tissue penetrating delivery of compounds and nanoparticles into tumors”, Cancer Cell 16(6):510-20 (2009).
Talanian, et al., “Substrate specificities of caspase family proteases”, J. Biol. Chem., 272: 9677-82 (1997).
Teesalu, et al., “Tumor-Penetrating Peptides”, Frontiers in Oncology, 3(216): 1-8 (2013).
Teesalu, et al., “C-end rule peptides mediate neuropilin-1-dependent cell, vascular and tissue penetration”, PNAS, 106(38):16157-62 (2009).
Thomas, “Furin at the cutting edge: from protein traffic to embryogenesis and disease”, Nature Rev. Mol. Cell. Biol. 3:753-66 (2002).
Thomas, et al., “Tissue distribution and pharmacokinetics of an ATWLPPR-conjugated chlorin-type photosensitizer targeting neuropilin-1 in glioma-bearing nude mice”, Photochemical & photobiological Sciences, 7(4):433 (2008).
Thornberry, et al., “A combinatorial approach defines specificities of members of the caspase family and granzyme B. Functional relationships established for key mediators of apoptosis”, J. Biol. Chem. 272: 17907-11 (1997).
Thorson, et al., “A biosynthetic approach for the incorporation of unnatural amino acids into proteins”, Methods in Molec. Biol., 77:43-73 (1991).
Thurber, et al., “Antibody tumor penetration: transport opposed by systemic and antigen-mediated clearance”, Adv Drug Deliv Rev, 60:1421-34 (2008).
Tian, et al., “A 20 residues Motif Delineates the Furin Cleavage Site and its Physical Properties May Influence Viral Fusion”, BioChemistry Insights, 2:9-20 (2009).
Tirand, et al., “A peptide competing with VEGF165 binding on neuropilin-1 mediates targeting of a chlorin-type photosensitizer and potentiates its photodynamic activity in human endothelial cells”, J Contr. Rel., 111:153-64 (2006).
Tkachenko, et al., “Multifunctional gold nanoparticle-peptide complexes for nuclear targeting”, J Am Chem Soc. 125:4700-1 (2003).
Torgersen, et al., “Internalization of cholera toxin by diffeent endocytic mechanisms”, J. Cell. Sci., 114:3737-47 (2001).
Tucker, “Alpha v integrin inhibitors and cancer therapy”, Curr Opin Investig Drugs 4:722-31 (2003).
Tyagi, et al., “Internalization of HIV-1 tat requires cell surface heparan sulfate proteoglycans”, J. Biol. Chem., 276:3254-61 (2001).
Uhland, “Matriptase and its putative role in cancer”, Cell. Mol. Life Sci., 63:2968-78 (2006).
Uprichard, “The therapeutic potential of RNA interference”, FEBS Lett., 579:5996-6007 (2005).
Vander Kooi, et al., “Structural basis for ligand and heparin binding to neuropilin B domains”, PNAS, 104(15):6152-57 (2007).
Varsanyi, et al., “Isolation and characterization of the measles virus F1 polypeptide: comparison with other paramyxovirus fusion proteins”, Virology 147:110-17 (1985).
Vey, et al., “Proteolytic processing of human cytomegalovirus glycoprotein B (gpUL55) is mediated by the human endoprotease furin”, Virology 206:746-49 (1995).
von Maltzahn, et al., “In vivo tumor cell targeting with “click” nanoparticles”, Bioconjug Chem, 19:1570-8 (2008).
Weissleder, et al., “Cell-specific targeting of nanoparticles by multivalent attachment of small molecules”, Nat. Biotechnol., 23:1418-23 (2005).

(56) References Cited

OTHER PUBLICATIONS

Weissleder, et al., "Long-circulating iron oxide for MR imaging", Adv. Drug Deliv. Rev., 16: 321-34 (1995).
Werb, "ECM and cell surface proteolysis: regulating cellular ecology", Cell, 91:439-42 (1997).
White, et al. Antibody-targeted immunotherapy for treatment of malignancy, Annu Rev Med., 52:125-41 (2001).
Wolfsberg, et al., "ADAM, a novel family of membrane proteins containing A Disintegrin and Metalloprotease domain: multipotential functions in cell-cell and cell-matrix interactions", J. Cell Biol., 131:275-8 (1995).
Wool-Lewis and Bates, "Endoproteolytic processing of the ebola virus envelope glycoprotein: cleavage is not required for function", J. Virol. 73:1419-26 (1999).
Yang, et al., "A fluorescent orthotopic bone metasis model of human prostate cancer", Cancer Res, 59:781-6, 1999).
Yuan, et al., "Microvascular permeability and interstitial penetration of sterically stabilized (stealth) liposomes in a human tumor xenograft", Cancer Res, 54:3352-56 (1994).
Zhang, et al., "Dynamic imaging of arginine-rich heart-targeted vehicles in a mouse model", Biomaterials, 29:1976-88 (2008).
Zhang, et al., Lymphatic zip codes in premalignant lesions and tumors. Cancer Res. 66, 5696-5706 (2006).
Zhang, et al., "Molecular profiling of heart endothelial cells", Circulation. 112:1601-11 (2005).
Zorko and Langel, "Cell-penetrating peptides: mechanism and kinetics of cargo delivery", Adv Drug Deliv Rev. 57:529-45 (2005).

* cited by examiner

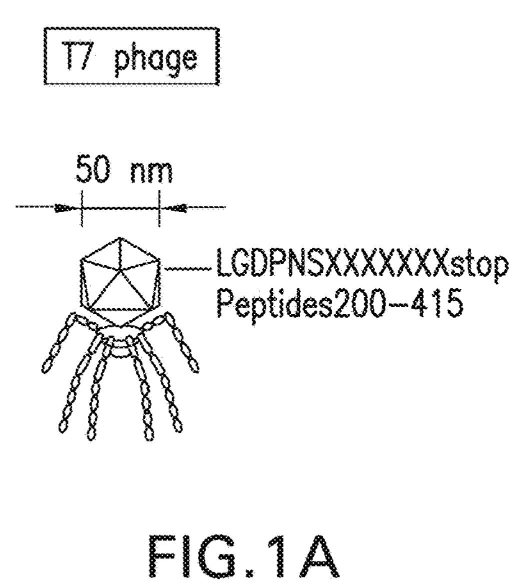

FIG.1A

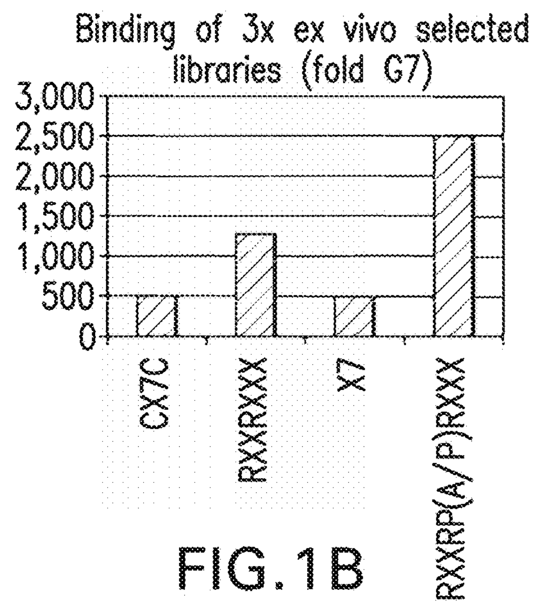

FIG.1B

| BINDING CONDITIONS | DISPLAYED PEPTIDES AFTER 3 ROUNDS OF SELECTION | | | |
|---|---|---|---|---|
| | CX7C | RXXRXXX | RXXRP(A/P)RXXX | X7 |
| 4 °C | CSVIQRSPR<br>CAPRTPR<br>PIPAR<br>CPR<br>CIKTAR<br>CLQPR<br>CSGIR<br>CVRSPR<br>CRTVVR<br>CNHGNRQQC | RGARDIR<br>RPVRTSR<br>R<br>RLSRNPR<br>RPTRMPR<br>RVSRR<br>RGVR<br>RM<br>RIRRTDR<br>RLQRVHR | RVRRPARTSF<br>RKFRRPPRRVLA<br>RTMTRPARASV<br>REVRPPR<br>RHLRPAR<br>RVKRPPRAER<br>RPGRPPRFSA<br>RAQRPARDHR<br>R<br>RAPRPAR | VVERVRR<br>DKDKPLR<br>GTWKQAR<br>AVRRSAR<br>AKGRSPR<br>ARVRGYR<br>RGVRGFR<br>RTQR<br>SIRRPPR<br>RSRTQSR |
| 37 °C+ acid wash | CRPVR<br>CSKTAR<br>CSLRTPK<br>CRKKR<br>CRRR<br>CRKR<br>CRPRR<br>CPKRDR<br>CREKPER<br>CMPKRER | RTVRAAR<br>RGARR<br>RSQRSAR<br>REKRVTR<br>RPGRSRR<br>RRPRPAR<br>RFVRQST<br>RSGRAMR<br>RGPRVSR<br>RTVRNSR | RERRPARETT<br>RGLRPAR<br>RVYRPARNLR<br>RVGRPARSRS<br>RITRPAR<br>RDRRPPR<br>RFGRPPR<br>RGTRPARWDR<br>RGVRPPR<br>RGVRPARSIH | GGTRPVR<br>RAVRSPR<br>HTHRLPR<br>VKGPARR<br>IPVRSLR<br>LRKYSTR<br>DRGAR<br>DRLRHAR<br>GMGRKFR<br>GRHSEVR |

FIG.1C

Binding of T7 to PPC1 cells at 4 °C
FIG.2A
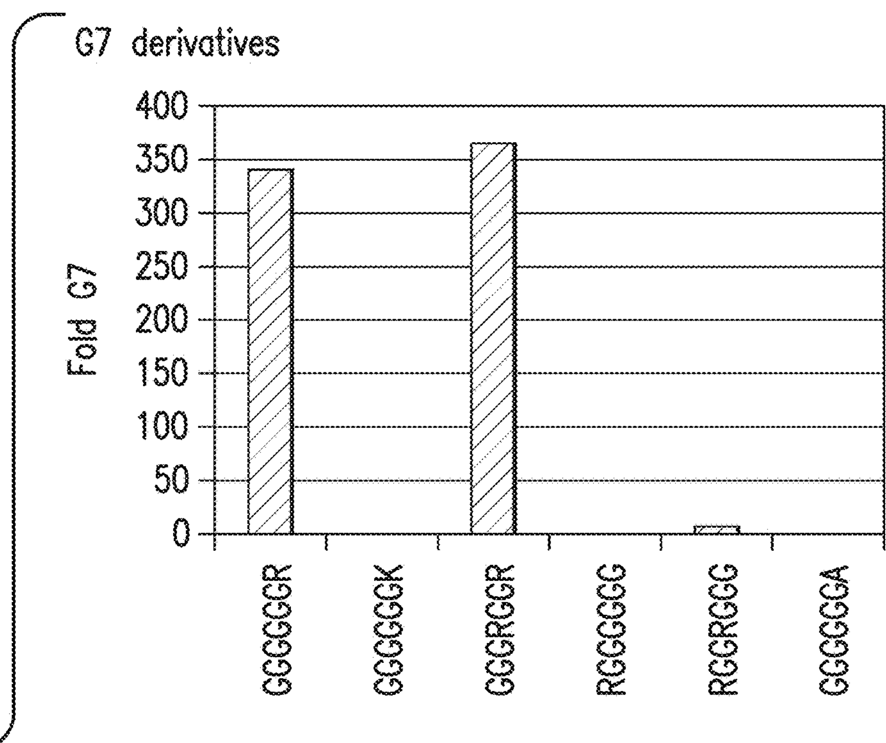
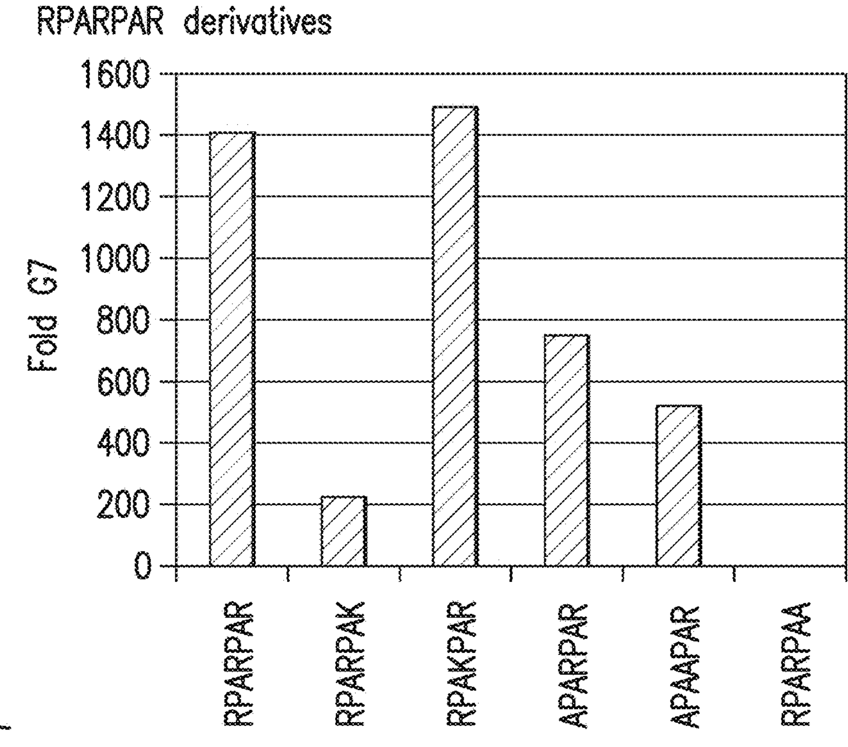

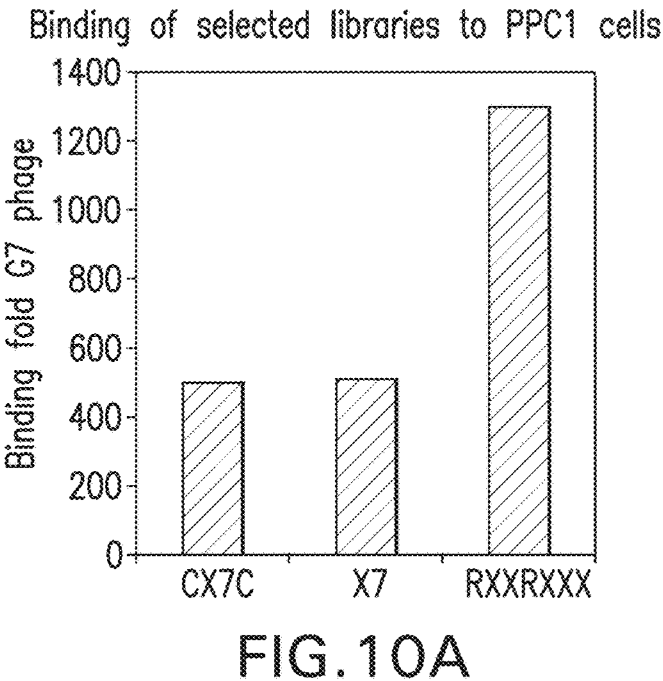

FIG. 10A

| BINDING | CX7C | X7 | RXXRXXX |
|---|---|---|---|
| 4 °C | CSVIQRSPR<br>CAPRTPR<br>PIPAR<br>CPR<br>CIKTAR<br>CLQPR<br>CSGIR<br>CVRSPR<br>CRTVVR<br>CNHGNRQQC | VVERVRR<br>DKDKPLR<br>GTWKQAR<br>AVRRSAR<br>AKGRSPR<br>ARVRGYR<br>RGVRGFR<br>RTQR<br>SIRRPPR<br>RSRTQSR | RPVRTSR<br>R<br>RLSRNPR<br>RPTRMPR<br>RGVR<br>RIRRTDR<br>RLQRVHR<br>RPARPAR<br>RGERPPR<br>RVTRPPR |
| 37 °C + acid wash | CRPVR<br>CSKTAR<br>CSLRTPK<br>CRKKR<br>CRRR<br>CRKR<br>CRPRR<br>CPKRDR<br>CREKPER<br>CMPKRER | GGTRPVR<br>RAVRSPR<br>HTHRLPR<br>VKGPARR<br>IPVRSLR<br>LRKYSTR<br>DRGAR<br>DRLRHAR<br>GMGRKFR<br>GRHSEVR | RTVRAAR<br>RGARR<br>RSQRSAR<br>REKRVTR<br>RPGRSRR<br>RRPRPAR<br>RFVRQST<br>RSGRAMR<br>RGPRVSR<br>RTVRNSR |

FIG. 10B

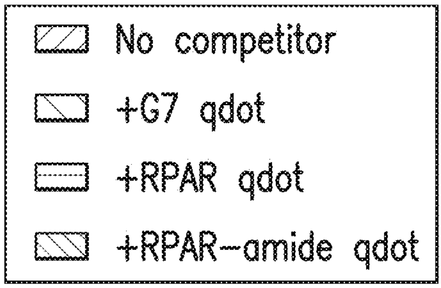
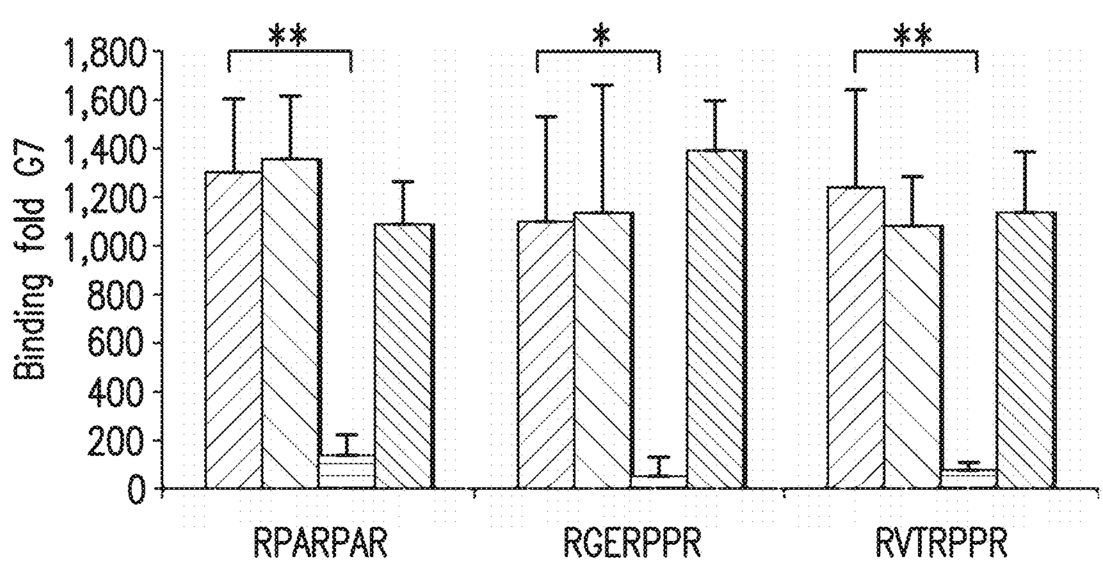
FIG.12A

Phage immunoreactivity in lung

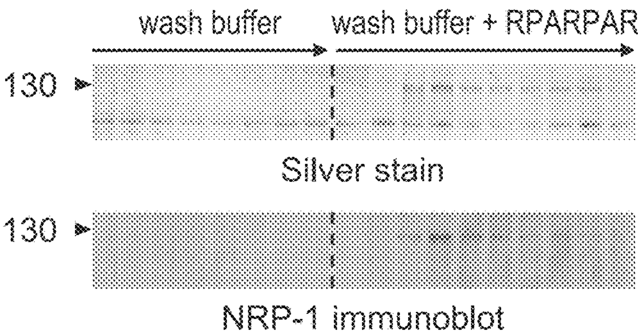
FIG.18A
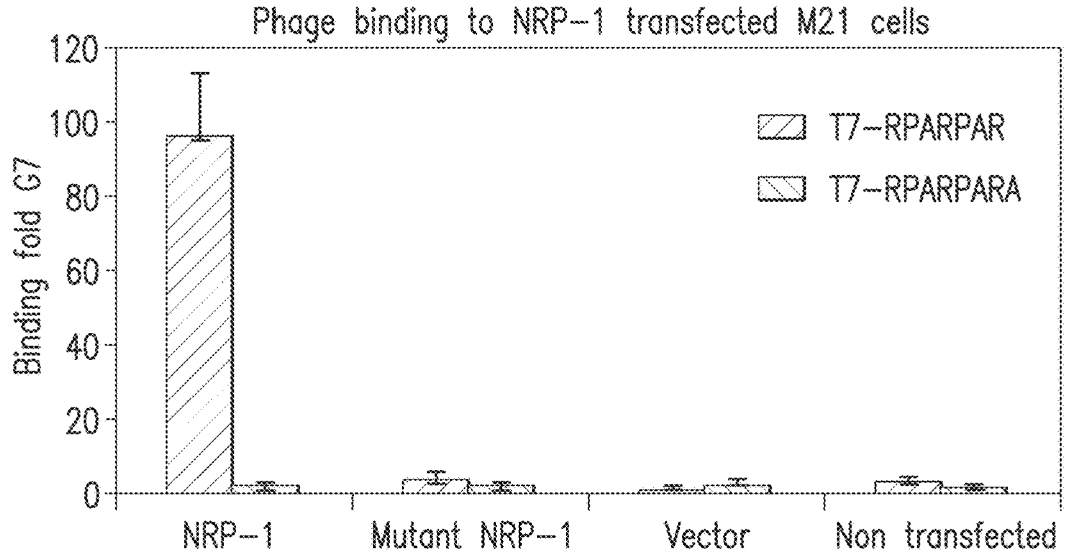
FIG.18B
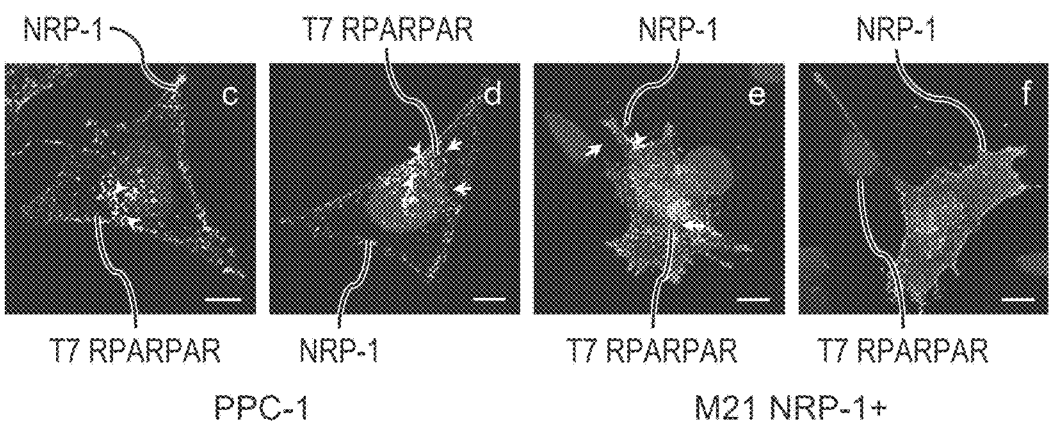
FIG.18C

SEQUENCE LISTING

```
<160> NUMBER OF SEQ ID NOS: 191

<210> SEQ ID NO 1
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 1

Gly Gly Gly Gly Gly Gly Arg
1               5


<210> SEQ ID NO 2
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 2

Arg Pro Ala Arg Pro Ala Arg
1               5


<210> SEQ ID NO 3
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)

<400> SEQUENCE: 3

Arg Pro Ala Arg Pro Ala Arg Ala
1               5


<210> SEQ ID NO 4
<211> LENGTH: 9
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(9)

<400> SEQUENCE: 4

Cys Arg Gly Asp Lys Gly Pro Asp Cys
1               5


<210> SEQ ID NO 5
<211> LENGTH: 14
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(14)

<400> SEQUENCE: 5
```

```
Lys Leu Ala Lys Leu Ala Lys Lys Leu Ala Lys Leu Ala Lys
1               5                   10


<210> SEQ ID NO 6
<211> LENGTH: 12
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(12)

<400> SEQUENCE: 6

Cys Ser Trp Arg Gly Leu Glu Asn His Arg Met Cys
1               5                   10


<210> SEQ ID NO 7
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 7

Cys Arg Glu Lys Ala
1               5


<210> SEQ ID NO 8
<211> LENGTH: 12
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(11)

<400> SEQUENCE: 8

Gly Gly Gly Arg Lys Lys Arg Ser Thr Gly Gly Gly
1               5                   10


<210> SEQ ID NO 9
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 9

Gly Gly Gly Arg Lys Lys Arg
1               5


<210> SEQ ID NO 10
<211> LENGTH: 12
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(11)

<400> SEQUENCE: 10
```

```
Gly Gly Gly Leu Val Pro Arg Gly Ser Gly Gly Gly
1               5                   10


<210> SEQ ID NO 11
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 11

Gly Gly Gly Leu Val Pro Arg
1               5


<210> SEQ ID NO 12
<211> LENGTH: 13
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(12)

<400> SEQUENCE: 12

Gly Gly Gly Pro Cys Pro Gly Arg Val Val Gly Gly Gly
1               5                   10


<210> SEQ ID NO 13
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)

<400> SEQUENCE: 13

Gly Gly Gly Pro Cys Pro Gly Arg
1               5


<210> SEQ ID NO 14
<211> LENGTH: 13
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(13)

<400> SEQUENCE: 14

Gly Gly Gly Pro Gly Ser Gly Arg Ser Ala Gly Gly Gly
1               5                   10


<210> SEQ ID NO 15
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)
```

<400> SEQUENCE: 15

Gly Gly Gly Pro Gly Ser Gly Arg
1 5

<210> SEQ ID NO 16
<211> LENGTH: 13
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(13)

<400> SEQUENCE: 16

Gly Gly Gly Pro Gly Ser Gly Lys Ser Ala Gly Gly Gly
1 5 10

<210> SEQ ID NO 17
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)

<400> SEQUENCE: 17

Gly Gly Gly Pro Gly Ser Gly Lys
1 5

<210> SEQ ID NO 18
<211> LENGTH: 10
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(10)

<400> SEQUENCE: 18

Cys Gly Leu Ile Ile Gln Lys Asn Glu Cys
1 5 10

<210> SEQ ID NO 19
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 19

Arg Xaa Xaa Arg Xaa Xaa Xaa
1 5

<210> SEQ ID NO 20
<211> LENGTH: 10
<212> TYPE: PRT
<213> ORGANISM: Artificial Sequence
<220> FEATURE:
<223> OTHER INFORMATION: REAGENT
<220> FEATURE:
<221> NAME/KEY: misc_feature
<222> LOCATION: (2)..(3)

```
<223> OTHER INFORMATION: Xaa can be any naturally occurring amino acid
<220> FEATURE:
<221> NAME/KEY: VARIANT
<222> LOCATION: (5)..(5)
<223> OTHER INFORMATION: Xaa can be Alanine or Proline
<220> FEATURE:
<221> NAME/KEY: misc_feature
<222> LOCATION: (8)..(10)
<223> OTHER INFORMATION: Xaa can be any naturally occurring amino acid

<400> SEQUENCE: 20

Arg Xaa Xaa Arg Xaa Pro Arg Xaa Xaa Xaa
1               5                   10


<210> SEQ ID NO 21
<211> LENGTH: 6
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(6)

<400> SEQUENCE: 21

Cys Arg Gly Asp Lys Gly
1               5


<210> SEQ ID NO 22
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 22

Cys Arg Gly Asp Lys
1               5


<210> SEQ ID NO 23
<211> LENGTH: 4
<212> TYPE: PRT
<213> ORGANISM: Artificial Sequence
<220> FEATURE:
<223> OTHER INFORMATION: REAGENT
<220> FEATURE:
<221> NAME/KEY: VARIANT
<222> LOCATION: (1)..(1)
<223> OTHER INFORMATION: Xaa can be Arginine or Lysine
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: Xaa can be Arginine or Lysine

<400> SEQUENCE: 23

Xaa Xaa Xaa Xaa
1


<210> SEQ ID NO 24
<211> LENGTH: 3
<212> TYPE: PRT
<213> ORGANISM: Artificial Sequence
<220> FEATURE:
<223> OTHER INFORMATION: REAGENT
```

```
<220> FEATURE:
<221> NAME/KEY: VARIANT
<222> LOCATION: (1)..(1)
<223> OTHER INFORMATION: Xaa can be Arginine, Lysine, or any nucleotide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: VARIANT
<222> LOCATION: (3)..(3)
<223> OTHER INFORMATION: Xaa can be Arginine or Lysine

<400> SEQUENCE: 24

Xaa Xaa Xaa
1


<210> SEQ ID NO 25
<211> LENGTH: 4
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(4)

<400> SEQUENCE: 25

Arg Xaa Xaa Arg
1


<210> SEQ ID NO 26
<211> LENGTH: 4
<212> TYPE: PRT
<213> ORGANISM: Artificial Sequence
<220> FEATURE:
<223> OTHER INFORMATION: REAGENT
<220> FEATURE:
<221> NAME/KEY: VARIANT
<222> LOCATION: (1)..(1)
<223> OTHER INFORMATION: Xaa can be Arginine or Lysine
<220> FEATURE:
<221> NAME/KEY: misc_feature
<222> LOCATION: (2)..(3)
<223> OTHER INFORMATION: Xaa can be any naturally occurring amino acid

<400> SEQUENCE: 26

Xaa Xaa Xaa Arg
1


<210> SEQ ID NO 27
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 27

Arg Gly Glu Arg Pro Pro Arg
1               5


<210> SEQ ID NO 28
<211> LENGTH: 7
<212> TYPE: PRT
<213> ORGANISM: Artificial Sequence
<220> FEATURE:
<223> OTHER INFORMATION: REAGENT
<220> FEATURE:
```

<221> NAME/KEY: UNSURE
<222> LOCATION: (1)..(7)

<400> SEQUENCE: 28

Arg Val Thr Arg Pro Pro Arg
1               5

<210> SEQ ID NO 29

<400> SEQUENCE: 29

000

<210> SEQ ID NO 30
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)

<400> SEQUENCE: 30

Cys Arg Cys Asp Lys Pro Arg Arg
1               5

<210> SEQ ID NO 31
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 31

Ala Thr Trp Leu Pro Pro Arg
1               5

<210> SEQ ID NO 32
<211> LENGTH: 4
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(4)

<400> SEQUENCE: 32

Thr Lys Pro Arg
1

<210> SEQ ID NO 33
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 33

Thr Lys Pro Pro Arg
1               5

<210> SEQ ID NO 34
<211> LENGTH: 14
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(14)

<400> SEQUENCE: 34

Arg Pro Ala Arg Ser Gly Arg Ser Ala Gly Gly Ser Val Ala
1 5 10

<210> SEQ ID NO 35
<211> LENGTH: 14
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(14)

<400> SEQUENCE: 35

Leu Asn Ile Thr His Arg Thr Arg Arg Ser Thr Ser Asp Asn
1 5 10

<210> SEQ ID NO 36
<211> LENGTH: 15
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(15)

<400> SEQUENCE: 36

Ser Val Ala Ser Ser Arg Arg His Lys Arg Phe Ala Gly Val Val
1 5 10 15

<210> SEQ ID NO 37
<211> LENGTH: 14
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(14)

<400> SEQUENCE: 37

Lys Gln Glu Gly Ser Arg Thr Arg Arg Ser Val Leu Ile Pro
1 5 10

<210> SEQ ID NO 38
<211> LENGTH: 14
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(13)

<400> SEQUENCE: 38

Pro Ala Thr Asn Asn Arg Ala Arg Arg Glu Leu Pro Arg Phe
1 5 10

<210> SEQ ID NO 39
<211> LENGTH: 15
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(15)

<400> SEQUENCE: 39

```
Pro Gln Arg Glu Arg Arg Arg Lys Lys Arg Gly Leu Phe Gly Ala
1               5                   10                  15
```

<210> SEQ ID NO 40
<211> LENGTH: 14
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(14)

<400> SEQUENCE: 40

```
Arg Arg Val Val Gln Arg Glu Lys Arg Ala Val Gly Ile Gly
1               5                   10
```

<210> SEQ ID NO 41
<211> LENGTH: 14
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(14)

<400> SEQUENCE: 41

```
Leu Ile Thr Gly Gly Arg Arg Thr Arg Arg Glu Ala Ile Val
1               5                   10
```

<210> SEQ ID NO 42
<211> LENGTH: 15
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(15)

<400> SEQUENCE: 42

```
Pro Ser Ser Gly Ser Arg Arg His Lys Arg Phe Ala Gly Ile Ala
1               5                   10                  15
```

<210> SEQ ID NO 43
<211> LENGTH: 14
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(14)

<400> SEQUENCE: 43

```
Cys Asp Ser Ala Gly Arg Ser Arg Arg Ser Arg Arg Ala Ile
```

1 5 10

<210> SEQ ID NO 44
<211> LENGTH: 13
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(13)

<400> SEQUENCE: 44

Ala Ala Val Leu Arg Arg Arg Arg Arg Asp Ala Gly Asn
1 5 10

<210> SEQ ID NO 45
<211> LENGTH: 14
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(14)

<400> SEQUENCE: 45

Gln Ile Glu Asn Pro Arg Gln Ser Arg Phe Val Leu Gly Ala
1 5 10

<210> SEQ ID NO 46
<211> LENGTH: 14
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(14)

<400> SEQUENCE: 46

Pro Pro Pro Ala Thr Arg Arg Arg Arg Ala Val Pro Ile Ala
1 5 10

<210> SEQ ID NO 47
<211> LENGTH: 14
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(14)

<400> SEQUENCE: 47

Pro Ser Pro Thr Asn Arg Ser Lys Arg Asn Leu Lys Met Glu
1 5 10

<210> SEQ ID NO 48
<211> LENGTH: 12
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(12)

<400> SEQUENCE: 48

```
Thr Cys Ala Ala Ala Ala Gly Ala Ala Ala Cys Cys
1               5                   10


<210> SEQ ID NO 49
<211> LENGTH: 12
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(12)

<400> SEQUENCE: 49

Gly Cys Thr Ala Ala Ala Gly Cys Thr Gly Cys Thr
1               5                   10


<210> SEQ ID NO 50
<211> LENGTH: 4
<212> TYPE: PRT
<213> ORGANISM: Artificial Sequence
<220> FEATURE:
<223> OTHER INFORMATION: REAGENT
<220> FEATURE:
<221> NAME/KEY: VARIANT
<222> LOCATION: (1)..(1)
<223> OTHER INFORMATION: Xaa can be Arginine or Lysine or Histidine
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: Xaa can be Arginine or Lysine or Histidine

<400> SEQUENCE: 50

Xaa Xaa Xaa Xaa
1


<210> SEQ ID NO 51
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: VARIANT
<222> LOCATION: (1)..(1)
<223> OTHER INFORMATION: Xaa can be Arginine or Lysine or Histidine
<220> FEATURE:
<221> NAME/KEY: misc_feature
<222> LOCATION: (2)..(3)
<223> OTHER INFORMATION: Xaa can be any naturally occurring amino acid

<400> SEQUENCE: 51

Xaa Xaa Xaa Lys Gly
1               5


<210> SEQ ID NO 52
<211> LENGTH: 9
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(9)

<400> SEQUENCE: 52

Cys Ser Val Ile Gln Arg Ser Pro Arg
```

1 5

<210> SEQ ID NO 53
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 53

Cys Ala Pro Arg Thr Pro Arg
1 5

<210> SEQ ID NO 54
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 54

Pro Ile Pro Ala Arg
1 5

<210> SEQ ID NO 55
<211> LENGTH: 3
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(3)

<400> SEQUENCE: 55

Cys Pro Arg
1

<210> SEQ ID NO 56
<211> LENGTH: 6
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(6)

<400> SEQUENCE: 56

Cys Ile Lys Thr Ala Arg
1 5

<210> SEQ ID NO 57
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 57

Cys Leu Gln Pro Arg
1 5

<210> SEQ ID NO 58
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 58

Cys Ser Gly Ile Arg
1 5

<210> SEQ ID NO 59
<211> LENGTH: 6
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(6)

<400> SEQUENCE: 59

Cys Val Arg Ser Pro Arg
1 5

<210> SEQ ID NO 60
<211> LENGTH: 6
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(6)

<400> SEQUENCE: 60

Cys Arg Thr Val Val Arg
1 5

<210> SEQ ID NO 61
<211> LENGTH: 9
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(9)

<400> SEQUENCE: 61

Cys Asn His Gly Asn Arg Gln Gln Cys
1 5

<210> SEQ ID NO 62
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 62

Val Val Glu Arg Val Arg Arg
1 5

<210> SEQ ID NO 63
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 63

Asp Lys Asp Lys Pro Leu Arg
1 5

<210> SEQ ID NO 64
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 64

Gly Thr Trp Lys Gln Ala Arg
1 5

<210> SEQ ID NO 65
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 65

Ala Val Arg Arg Ser Ala Arg
1 5

<210> SEQ ID NO 66
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 66

Ala Lys Gly Arg Ser Pro Arg
1 5

<210> SEQ ID NO 67
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 67

Ala Arg Val Arg Gly Tyr Arg
1 5

<210> SEQ ID NO 68
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 68

Arg Gly Val Arg Gly Phe Arg
1 5

<210> SEQ ID NO 69
<211> LENGTH: 4
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(4)

<400> SEQUENCE: 69

Arg Thr Gln Arg
1

<210> SEQ ID NO 70
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 70

Ser Ile Arg Arg Pro Pro Arg
1 5

<210> SEQ ID NO 71
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 71

Arg Ser Arg Thr Gln Ser Arg
1 5

<210> SEQ ID NO 72
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 72

Arg Pro Val Arg Thr Ser Arg
1 5

<210> SEQ ID NO 73
<211> LENGTH: 1
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(1)

<400> SEQUENCE: 73

Arg
1

<210> SEQ ID NO 74
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 74

Arg Leu Ser Arg Asn Pro Arg
1 5

<210> SEQ ID NO 75
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 75

Arg Pro Thr Arg Met Pro Arg
1 5

<210> SEQ ID NO 76
<211> LENGTH: 4
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(4)

<400> SEQUENCE: 76

Arg Gly Val Arg
1

<210> SEQ ID NO 77
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE

<222> LOCATION: (1)..(7)

<400> SEQUENCE: 77

Arg Ile Arg Arg Thr Asp Arg
1               5

<210> SEQ ID NO 78
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 78

Arg Leu Gln Arg Val His Arg
1               5

<210> SEQ ID NO 79
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 79

Arg Pro Ala Arg Pro Ala Arg
1               5

<210> SEQ ID NO 80
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 80

Arg Gly Glu Arg Pro Pro Arg
1               5

<210> SEQ ID NO 81
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 81

Arg Val Thr Arg Pro Pro Arg
1               5

<210> SEQ ID NO 82
<211> LENGTH: 5
<212> TYPE: PRT
<213> ORGANISM: Artificial Sequence
<220> FEATURE:
<223> OTHER INFORMATION: REAGENT
<220> FEATURE:

<221> NAME/KEY: UNSURE
<222> LOCATION: (1)..(5)

<400> SEQUENCE: 82

Cys Arg Pro Val Arg
1 5

<210> SEQ ID NO 83
<211> LENGTH: 6
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(6)

<400> SEQUENCE: 83

Cys Ser Lys Thr Ala Arg
1 5

<210> SEQ ID NO 84
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 84

Cys Ser Leu Arg Thr Pro Lys
1 5

<210> SEQ ID NO 85
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 85

Cys Arg Lys Lys Arg
1 5

<210> SEQ ID NO 86
<211> LENGTH: 4
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(4)

<400> SEQUENCE: 86

Cys Arg Arg Arg
1

<210> SEQ ID NO 87
<211> LENGTH: 4
<212> TYPE: PRT
<213> ORGANISM: Artificial Sequence
<220> FEATURE:
<223> OTHER INFORMATION: REAGENT

```
<220> FEATURE:
<221> NAME/KEY: UNSURE
<222> LOCATION: (1)..(4)

<400> SEQUENCE: 87

Cys Arg Lys Arg
1


<210> SEQ ID NO 88
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 88

Cys Arg Pro Arg Arg
1               5


<210> SEQ ID NO 89
<211> LENGTH: 6
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(6)

<400> SEQUENCE: 89

Cys Pro Lys Arg Asp Arg
1               5


<210> SEQ ID NO 90
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: unsure
<222> LOCATION: (1)..(7)

<400> SEQUENCE: 90

Cys Arg Glu Lys Pro Glu Arg
1               5


<210> SEQ ID NO 91
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 91

Cys Met Pro Lys Arg Glu Arg
1               5


<210> SEQ ID NO 92
<211> LENGTH: 7
<212> TYPE: PRT
<213> ORGANISM: Artificial Sequence
<220> FEATURE:
```

<223> OTHER INFORMATION: REAGENT
<220> FEATURE:
<221> NAME/KEY: UNSURE
<222> LOCATION: (1)..(7)

<400> SEQUENCE: 92

Gly Gly Thr Arg Pro Val Arg
1 5

<210> SEQ ID NO 93
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 93

Arg Ala Val Arg Ser Pro Arg
1 5

<210> SEQ ID NO 94
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 94

His Thr His Arg Leu Pro Arg
1 5

<210> SEQ ID NO 95
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 95

Val Lys Gly Pro Ala Arg Arg
1 5

<210> SEQ ID NO 96
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 96

Ile Pro Val Arg Ser Leu Arg
1 5

<210> SEQ ID NO 97
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 97

Leu Arg Lys Tyr Ser Thr Arg
1               5

<210> SEQ ID NO 98
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 98

Asp Arg Gly Ala Arg
1               5

<210> SEQ ID NO 99
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 99

Asp Arg Leu Arg His Ala Arg
1               5

<210> SEQ ID NO 100
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 100

Gly Met Gly Arg Lys Phe Arg
1               5

<210> SEQ ID NO 101
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 101

Gly Arg His Ser Glu Val Arg
1               5

<210> SEQ ID NO 102
<211> LENGTH: 7
<212> TYPE: PRT

<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 102

Arg Thr Val Arg Ala Ala Arg
1               5

<210> SEQ ID NO 103
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 103

Arg Gly Ala Arg Arg
1               5

<210> SEQ ID NO 104
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 104

Arg Ser Gln Arg Ser Ala Arg
1               5

<210> SEQ ID NO 105
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 105

Arg Glu Lys Arg Val Thr Arg
1               5

<210> SEQ ID NO 106
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 106

Arg Pro Gly Arg Ser Arg Arg
1               5

<210> SEQ ID NO 107
<211> LENGTH: 7

<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 107

Arg Arg Pro Arg Pro Ala Arg
1 5

<210> SEQ ID NO 108
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 108

Arg Phe Val Arg Gln Ser Thr
1 5

<210> SEQ ID NO 109
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 109

Arg Ser Gly Arg Ala Met Arg
1 5

<210> SEQ ID NO 110
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 110

Arg Gly Pro Arg Val Ser Arg
1 5

<210> SEQ ID NO 111
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 111

Arg Thr Val Arg Asn Ser Arg
1 5

<210> SEQ ID NO 112

<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 112

Arg Pro Ala Arg Pro Ala Lys
1 5

<210> SEQ ID NO 113
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 113

Arg Pro Ala Arg Pro Ala Ala
1 5

<210> SEQ ID NO 114
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 114

Arg Pro Ala Lys Pro Ala Arg
1 5

<210> SEQ ID NO 115
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 115

Ala Pro Ala Arg Pro Ala Arg
1 5

<210> SEQ ID NO 116
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 116

Ala Pro Ala Ala Pro Ala Arg
1 5

<210> SEQ ID NO 117
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 117

Ala Pro Ala Arg Pro Ala Ala
1               5

<210> SEQ ID NO 118
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 118

Arg Pro Ala Ala Pro Ala Ala
1               5

<210> SEQ ID NO 119
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)

<400> SEQUENCE: 119

Arg Pro Ala Arg Pro Ala Arg Lys
1               5

<210> SEQ ID NO 120
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)

<400> SEQUENCE: 120

Arg Pro Ala Arg Pro Ala Arg Asn
1               5

<210> SEQ ID NO 121
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)

<400> SEQUENCE: 121

Arg Pro Ala Arg Pro Ala Arg Ile
1               5

<210> SEQ ID NO 122
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)

<400> SEQUENCE: 122

Arg Pro Ala Arg Pro Ala Arg Pro
1               5

<210> SEQ ID NO 123
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)

<400> SEQUENCE: 123

Arg Pro Ala Arg Pro Ala Arg Ser
1               5

<210> SEQ ID NO 124
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 124

Arg Gly Glu Arg Pro Pro Arg
1               5

<210> SEQ ID NO 125
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 125

Arg Val Thr Arg Pro Pro Arg
1               5

<210> SEQ ID NO 126
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)

<400> SEQUENCE: 126

Cys Arg Cys Asp Lys Pro Arg Arg
1               5

<210> SEQ ID NO 127
<211> LENGTH: 9
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(9)

<400> SEQUENCE: 127

Cys Arg Cys Asp Lys Pro Arg Arg Ala
1               5

<210> SEQ ID NO 128
<211> LENGTH: 4
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(4)

<400> SEQUENCE: 128

Thr Lys Pro Arg
1

<210> SEQ ID NO 129
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 129

Thr Lys Pro Pro Arg
1               5

<210> SEQ ID NO 130
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 130

Ala Thr Trp Leu Pro Pro Arg
1               5

<210> SEQ ID NO 131
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 131

Asp Asp Asp Asp Lys 1 5

<210> SEQ ID NO 132
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 132

Arg Gly Ala Arg Asp Ile Arg
1 5

<210> SEQ ID NO 133
<211> LENGTH: 5
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(5)

<400> SEQUENCE: 133

Arg Val Ser Arg Arg
1 5

<210> SEQ ID NO 134
<211> LENGTH: 2
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(2)

<400> SEQUENCE: 134

Arg Met
1

<210> SEQ ID NO 135
<211> LENGTH: 10
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(10)

<400> SEQUENCE: 135

Arg Val Arg Arg Pro Ala Arg Thr Ser Phe
1 5 10

<210> SEQ ID NO 136
<211> LENGTH: 12
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(12)

<400> SEQUENCE: 136

Arg Lys Phe Arg Arg Pro Pro Arg Arg Val Leu Ala
1 5 10

<210> SEQ ID NO 137
<211> LENGTH: 11
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(11)

<400> SEQUENCE: 137

Arg Thr Met Thr Arg Pro Ala Arg Ala Ser Val
1 5 10

<210> SEQ ID NO 138
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 138

Arg Glu Val Arg Pro Pro Arg
1 5

<210> SEQ ID NO 139
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 139

Arg His Leu Arg Pro Ala Arg
1 5

<210> SEQ ID NO 140
<211> LENGTH: 10
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(10)

<400> SEQUENCE: 140

Arg Val Lys Arg Pro Pro Arg Ala Glu Arg
1 5 10

<210> SEQ ID NO 141
<211> LENGTH: 10
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(10)

<400> SEQUENCE: 141

```
Arg Pro Gly Arg Pro Pro Arg Phe Ser Ala
1               5                   10


<210> SEQ ID NO 142
<211> LENGTH: 10
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(10)

<400> SEQUENCE: 142

Arg Ala Gln Arg Pro Ala Arg Asp His Arg
1               5                   10


<210> SEQ ID NO 143
<211> LENGTH: 1
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(1)

<400> SEQUENCE: 143

Arg
1


<210> SEQ ID NO 144
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 144

Arg Ala Pro Arg Pro Ala Arg
1               5


<210> SEQ ID NO 145
<211> LENGTH: 10
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(10)

<400> SEQUENCE: 145

Arg Glu Arg Arg Pro Ala Arg Glu Thr Thr
1               5                   10


<210> SEQ ID NO 146
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)
```

<400> SEQUENCE: 146

Arg Gly Leu Arg Pro Ala Arg
1 5

<210> SEQ ID NO 147
<211> LENGTH: 10
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(10)

<400> SEQUENCE: 147

Arg Val Tyr Arg Pro Ala Arg Asn Leu Arg
1 5 10

<210> SEQ ID NO 148
<211> LENGTH: 10
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(10)

<400> SEQUENCE: 148

Arg Val Gly Arg Pro Ala Arg Ser Arg Ser
1 5 10

<210> SEQ ID NO 149
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 149

Arg Ile Thr Arg Pro Ala Arg
1 5

<210> SEQ ID NO 150
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 150

Arg Asp Arg Arg Pro Pro Arg
1 5

<210> SEQ ID NO 151
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 151

Arg Phe Gly Arg Pro Pro Arg
1 5

<210> SEQ ID NO 152
<211> LENGTH: 10
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(10)

<400> SEQUENCE: 152

Arg Gly Thr Arg Pro Ala Arg Trp Asp Arg
1 5 10

<210> SEQ ID NO 153
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 153

Arg Gly Val Arg Pro Pro Arg
1 5

<210> SEQ ID NO 154
<211> LENGTH: 10
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(10)

<400> SEQUENCE: 154

Arg Gly Val Arg Pro Ala Arg Ser Ile His
1 5 10

<210> SEQ ID NO 155
<211> LENGTH: 9
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(9)

<400> SEQUENCE: 155

Cys Gly Gly Gly Gly Gly Gly Gly Cys
1 5

<210> SEQ ID NO 156
<211> LENGTH: 9
<212> TYPE: PRT
<213> ORGANISM: Artificial Sequence
<220> FEATURE:
<223> OTHER INFORMATION: REAGENT
<220> FEATURE:
<221> NAME/KEY: UNSURE

<222> LOCATION: (1)..(9)

<400> SEQUENCE: 156

Cys Arg Gly Asp Lys Gly Pro Asp Cys
1               5

<210> SEQ ID NO 157
<211> LENGTH: 9
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(9)

<400> SEQUENCE: 157

Cys Arg Gly Asp Lys Gly Pro Asp Ala
1               5

<210> SEQ ID NO 158
<211> LENGTH: 9
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(9)

<400> SEQUENCE: 158

Cys Arg Gly Asp Lys Gly Pro Asp Gly
1               5

<210> SEQ ID NO 159
<211> LENGTH: 8
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(8)

<400> SEQUENCE: 159

Cys Arg Gly Asp Lys Gly Pro Asp
1               5

<210> SEQ ID NO 160
<211> LENGTH: 7
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(7)

<400> SEQUENCE: 160

Cys Arg Gly Asp Lys Gly Pro
1               5

<210> SEQ ID NO 161
<211> LENGTH: 4
<212> TYPE: PRT
<213> ORGANISM: Artificial Sequence
<220> FEATURE:
<223> OTHER INFORMATION: REAGENT
<220> FEATURE:

<221> NAME/KEY: UNSURE
<222> LOCATION: (1)..(4)

<400> SEQUENCE: 161

Cys Arg Gly Asp
1

<210> SEQ ID NO 162
<211> LENGTH: 3
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(3)

<400> SEQUENCE: 162

Cys Arg Gly
1

<210> SEQ ID NO 163
<211> LENGTH: 2
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(2)

<400> SEQUENCE: 163

Cys Arg
1

<210> SEQ ID NO 164
<211> LENGTH: 4
<212> TYPE: PRT
<213> ORGANISM: Artificial Sequence
<220> FEATURE:
<223> OTHER INFORMATION: REAGENT
<220> FEATURE:
<221> NAME/KEY: UNSURE
<222> LOCATION: (1)..(4)

<400> SEQUENCE: 164

Arg Pro Ala Arg
1

<210> SEQ ID NO 165
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 165

Lys Asp Lys Lys
1

<210> SEQ ID NO 166
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 166

Lys Phe Lys Lys
1

<210> SEQ ID NO 167
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 167

Lys Lys Lys Lys
1

<210> SEQ ID NO 168
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 168

Lys Leu Arg Lys
1

<210> SEQ ID NO 169
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 169

Lys Pro Pro Arg
1

<210> SEQ ID NO 170
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 170

Lys Arg Ser Arg
1

<210> SEQ ID NO 171
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 171

Lys Val Ile Arg
1

<210> SEQ ID NO 172
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 172

Lys Val Arg Lys

1

<210> SEQ ID NO 173
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 173

Lys Trp Lys Lys
1

<210> SEQ ID NO 174
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 174

Arg Leu Ala Lys
1

<210> SEQ ID NO 175
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 175

Arg Leu Ile Lys
1

<210> SEQ ID NO 176
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 176

Arg Arg Ala Arg
1

<210> SEQ ID NO 177
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 177

Arg Arg Glu Arg
1

<210> SEQ ID NO 178
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 178

Arg Arg Leu Lys
1

<210> SEQ ID NO 179
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 179

Arg Arg Asn Arg
1

<210> SEQ ID NO 180
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 180

Arg Arg Arg Arg
1

<210> SEQ ID NO 181
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 181

Arg Arg Val Arg
1

<210> SEQ ID NO 182
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 182

Arg Trp Arg Arg
1

<210> SEQ ID NO 183
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 183

Arg Arg Thr Lys
1

<210> SEQ ID NO 184
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 184

Arg Arg Pro Lys
1

<210> SEQ ID NO 185
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 185

Lys Gln Arg Arg
1

<210> SEQ ID NO 186
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 186

Lys Arg Ala Arg
1

<210> SEQ ID NO 187
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 187

Lys Arg Gly Arg
1

<210> SEQ ID NO 188
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 188

Arg Ser Phe Lys
1

<210> SEQ ID NO 189
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 189

Lys Lys Pro Arg
1

<210> SEQ ID NO 190
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 190

Arg Val Arg Arg
1

-continued

```
<210> SEQ ID NO 191
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 191

Lys Arg Thr Arg
1
```

METHODS AND COMPOSITIONS RELATED TO PEPTIDES AND PROTEINS WITH C-TERMINAL ELEMENTS

CROSS-REFERENCE TO RELATED APPLICATIONS

This application is a continuation of pending prior U.S. application Ser. No. 12/390,061, filed Feb. 20, 2009, which claims benefit of U.S. Provisional Application No. 61/030,409, filed Feb. 21, 2008. Application Ser. No. 12/390,061, filed Feb. 20, 2009, and Application No. 61/030,409, filed Feb. 21, 2008, are hereby incorporated herein by reference in their entirety.

STATEMENT REGARDING FEDERALLY SPONSORED RESEARCH

This invention was made with government support under CA119335, CA030199, CA104898, CA119414, CA124427, CA115410 and DK076050 awarded by the National Institutes of Health. The government has certain rights in the invention.

REFERENCE TO SEQUENCE LISTING

The Sequence Listing submitted as a text file named "SBMRI_35.8403_ST25.txt," created on Nov. 25, 2024, and having a size of 40,695 bytes is hereby incorporated by reference pursuant to 37 C.F.R. § 1.52(e)(5).

FIELD OF THE INVENTION

The present invention relates generally to the fields of molecular medicine, more specifically, to cell and tissue-penetrating peptides.

BACKGROUND OF THE INVENTION

Peptides that are internalized into cells are commonly referred to as cell-penetrating peptides. There are two main classes of such peptides: hydrophobic and cationic (Zorko and Langel, 2005). The cationic peptides, which are commonly used to introduce nucleic acids, proteins into cells, include the prototypic cell-penetrating peptides, Tat, and penetratin (Meade and Dowdy, 2007; Derossi et al., 1998). A herpes virus protein, VP22, is capable of both entering and exiting cells and carrying a payload with it (Elliott and O'Hare, 1997; Brewis et al., 2003). A major limitation of these peptides as delivery vehicles is that they are not selective; they enter into all cells. An activatable delivery system can be used which is more specific for one cell type or tissue.

Cell-penetrating delivery vehicles are important in a number of ways. First, internalization can improve targeting because internalization of the peptide and its payload into cells makes the homing more effective (Christian et al., 2003; Laakkonen et al., 2004; Weissleder at al., 1995). Second, cell-penetrating targeting elements can take payloads into the cytoplasm, which is critical, for example, in the delivery of nucleic acid-based therapeutics. Third, cell-penetrating properties, combined with exiting capabilities, can enhance extravasation and tissue spread.

Tissue penetration is a serious limitation in the delivery of compositions to cells. Comparison of the distribution of fluorescein-labeled peptides to that of iron oxide particles coated with the same peptide shows that the particles remain close to the tumor blood vessels, whereas the fluorescent peptide reaches all areas of the tumor. The frequently cited "leakiness" of tumor vessels does not appear to substantially mitigate this problem. Moreover, anti-angiogenic treatments that cause "normalization" of tumor vasculature (Jain, 2005), creating a need to target tumors whose vasculature is not leaky. Thus, it is important to find new ways of improving the passage of diverse compositions into the extravascular space. A number of proteins are known to translocate through the endothelium of blood vessels, including the blood-brain barrier. A prime example is transferrin, which is carried across the blood-brain barrier by the transferrin receptor. This system has been used to bring other payloads into the brain (Li et al., 2002; Fenart and Cecchelli, 2003). Peptide signals for endothelial transcytosis that can mediate translocation of compositions from the circulation into tissues is useful.

Thus, there is a need for new therapeutic strategies for selectively targeting various types of cells, and for internalizing proteins and peptides into those cells and penetration of tissue by proteins and peptides. The present invention satisfies this need by providing peptides that can be selectively targeted, and selectively internalized, by various types of cells and/or can penetrate tissue. Related advantages also are provided.

BRIEF SUMMARY OF THE INVENTION

Disclosed are CendR elements and proteins and peptides comprising CendR elements. Also disclosed are CendR conjugates comprising a cargo composition covalently coupled or non-covalently associated with a protein or peptide comprising a CendR element. Also disclosed are CendR conjugates comprising a cargo composition covalently coupled or non-covalently associated with a protein or peptide comprising a selected amino acid sequence, wherein the amino acid sequence comprises a CendR element. The cargo composition can be coupled or associated with the protein or peptide on the N terminal side of the CendR element.

Also disclosed are activatable CendR elements and proteins and peptides comprising activatable CendR elements. Also disclosed are activatable CendR conjugates comprising a cargo composition covalently coupled or non-covalently associated with a protein or peptide comprising an activatable CendR element. Also disclosed are activatable CendR conjugates comprising a cargo composition covalently coupled or non-covalently associated with a protein or peptide comprising a selected amino acid sequence, wherein the amino acid sequence comprises an activatable CendR element. The cargo composition can be coupled or associated with the protein or peptide on the N terminal side of the activatable CendR element.

Also disclosed are CendR conjugates made by the method comprising causing a cargo composition to be covalently coupled or non-covalently associated with a protein or peptide comprising a CendR element, wherein the cargo composition is coupled or associated with the protein or peptide on the N terminal side of the CendR element. Also disclosed are CendR conjugates made by the method comprising causing a cargo composition to be covalently coupled or non-covalently associated with a protein or peptide comprising a selected amino acid sequence, wherein the amino acid sequence comprises a C-terminal element, wherein the cargo composition is coupled or associated with the protein or peptide on the N terminal side of the CendR element. Also disclosed are CendR conjugates made by the method comprising (a) selecting an amino acid sequence for internalization into a cell and/or penetration of tissue, wherein the amino acid sequence comprises a C-terminal element, and (b) causing a cargo composition to be covalently coupled or non-covalently associated with a protein or peptide comprising the selected amino acid sequence, wherein the cargo composition is coupled or associated with the protein or peptide on the N terminal side of the CendR element. The CendR conjugate can comprise the protein or peptide and the coupled or associated cargo composition.

Also disclosed are activatable CendR elements made by the method comprising causing a blocking group to be covalently coupled to a CendR element, wherein a bond coupling the blocking group and the CendR element is cleavable. Also disclosed are activatable CendR element made by the method comprising causing a blocking group to be covalently coupled to an amino acid sequence, wherein the amino acid sequence comprises a CendR element, wherein a bond coupling the blocking group and the CendR element is cleavable. Also disclosed are activatable CendR element made by the method comprising (a) selecting an amino acid sequence for internalization into a cell and/or penetration of tissue, wherein the amino acid sequence comprises a CendR element, and (b) causing a blocking group to be covalently coupled to the CendR element, wherein a bond coupling the blocking group and the CendR element is cleavable. The blocking group covalently coupled to the CendR element reduces or prevents internalization into a cell and/or penetration of tissue. The blocking group covalently coupled to the CendR element can reduce or prevent internalization into a cell and/or penetration of tissue compared to the same CendR element with no blocking group. The activatable CendR element can comprise the selected amino acid sequence and the blocking group.

The protein or peptide can be internalized into a cell and/or can penetrate tissue when the CendR element is present in the protein or peptide but not when the CendR element is not present in the protein or peptide. The protein or peptide can be internalized into a cell and/or can penetrate tissue when the selected amino acid sequence is present in the protein or peptide but not when the selected amino acid is not present in the protein or peptide. The CendR element can be internalized into a cell and/or can penetrate tissue without being associated with the cargo composition. The selected amino acid sequence can be internalized into a cell and/or can penetrate tissue without being associated with the cargo composition. The CendR element can be the only functional internalization element in the protein or peptide, the CendR element can be the only functional tissue penetration element in the protein or peptide, or both. The selected amino acid sequence can be the only functional internalization element in the protein or peptide, the selected amino acid sequence can be the only functional tissue penetration element in the protein or peptide, or both. The CendR element can be the only functional internalization element in the CendR conjugate, the CendR element can be the only functional tissue penetration element in the CendR conjugate, or both. The selected amino acid sequence can be the only functional internalization element in the CendR conjugate, the selected amino acid sequence can be the only functional tissue penetration element in the CendR conjugate, or both.

The CendR element can be an activatable CendR element. The CendR element can be a protease-activatable CendR element. The protein or peptide can be circular (cyclic) or can contain a loop. The CendR element can be at the C-terminal end of the protein or peptide. The CendR element can comprise a terminal carboxyl group. A blocking group can be coupled to the terminal carboxyl group. The bond coupling the blocking group and the terminal carboxyl group can be selected to be cleavable by a protease present in proximity to the cell of interest. The blocking group can be coupled to the C-terminal amino acid of the CendR element. The blocking group can be coupled to an amino acid of the CendR element other than the C-terminal amino acid of the CendR element.

A cargo composition can be covalently coupled or non-covalently associated with a protein or peptide comprising a selected amino acid sequence, wherein the amino acid sequence can comprise a CendR element. The cargo composition can be coupled or associated with the protein or peptide, for example, on the N terminal side of the CendR element. The cargo composition can be, for example, a nanoparticle, or a molecule, or complex of molecules with therapeutic or diagnostic applications. Therapeutic cargo compositions that can be targeted with CendR elements include but are not limited to a nanoparticle, a molecule, a complex of molecules, an anti-angiogenic agent, a pro-angiogenic agent, a cancer chemotherapeutic agent, a cytotoxic agent, a pro-cell survival agent, a cell differentiating agent, a neuroprotective agent, an immunomodulatory agent, an anti-inflammatory agent, an anti-arthritic agent, an anti-viral agent, or a combination of these. Diagnostic cargo compositions that can be targeted with CendR elements include but are not limited to a nanoparticle, a molecule, a complex of molecules, a MRI imaging agent, a radioimaging agent, an optical imaging agent, a molecular tag (such as biotin), a fluorophore, an epitope tag (that can, for example, be detected using a specific molecular assay), or a combination of these. The cargo composition can comprise a homing sequence. The cargo composition can selectively home to a tumor or other target tissue. The cargo composition can selectively home to the vasculature of tumor or other target tissue.

Also disclosed are methods of forming a CendR conjugate, the method comprising causing a cargo composition to be covalently coupled or non-covalently associated with a protein or peptide comprising a CendR element, wherein the cargo composition is coupled or associated with the protein or peptide on the N terminal side of the CendR element. Also disclosed are methods of forming a CendR conjugate, the method comprising causing a cargo composition to be covalently coupled or non-covalently associated with a protein or peptide comprising a selected amino acid sequence, wherein the amino acid sequence comprises a CendR element, wherein the cargo composition is coupled or associated with the protein or peptide on the N terminal side of the CendR element. Also disclosed are methods of forming a CendR conjugate, the method comprising (a) selecting an amino acid sequence for internalization into a cell and/or penetration of tissue, wherein the amino acid sequence comprises a CendR element, and (b) causing a cargo composition to be covalently coupled or non-covalently associated with a protein or peptide comprising the selected amino acid sequence, wherein the cargo composition is coupled or associated with the protein or peptide on the N terminal side of the CendR element. The CendR conjugate can comprise the protein or peptide and the coupled or associated cargo composition.

Also disclosed are methods of delivering a cargo composition into a cell, the method comprising exposing the cell to a CendR conjugate, wherein the CendR element comprises a cargo composition covalently coupled or non-covalently associated with a CendR element, wherein the CendR conjugate can then enter the cell, thereby delivering the cargo composition into the cell. Also disclosed are methods of delivering a cargo composition into a cell, the method comprising exposing the cell to a CendR conjugate, wherein the CendR element comprises a cargo composition covalently coupled or non-covalently associated with a protein or peptide comprising a CendR element, wherein the CendR conjugate can then enter the cell, thereby delivering the cargo composition into the cell. Also disclosed are methods of delivering a cargo composition into a cell, the method comprising (a) coupling a CendR element to the cargo composition thus forming a CendR conjugate; and (b) exposing the cell to the CendR conjugate, wherein the CendR conjugate can then enter the cell, thereby delivering the cargo composition into the cell.

Also disclosed are methods of identifying a cell that can internalize a CendR element, the method comprising (a) exposing a cell to a CendR element, and (b) determining if the CendR element was internalized. Also disclosed are methods of identifying a cancer cell as a candidate for CendR-based therapy, the method comprising (a) exposing the cancer cell to a CendR element, and (b) determining if the CendR element was internalized by the cancer cell, wherein an internalized CendR element identifies the cancer cell as being a candidate for CendR-based therapy. The cell can be in an assay. The CendR element can be coupled to a protein or peptide. The CendR element can be an activatable CendR element. The activatable CendR element can be activated before exposure to the cell. The activatable CendR element can be a protease-activatable CendR element. The protein or peptide can be circular. The CendR element can be at the C-terminal end of the protein or peptide.

Also disclosed are methods of identifying a tissue that can be penetrated by a CendR element, the method comprising (a) exposing a tissue to a CendR element, and (b) determining if the CendR element penetrated the tissue. Also disclosed are methods of identifying a tumor as a candidate for CendR-based therapy, the method comprising (a) exposing a cell from the tumor to a CendR element, and (b) determining if the CendR element was internalized by the cell, wherein an internalized CendR element identifies the tumor as being a candidate for CendR-based therapy. Also disclosed are methods of identifying a tumor as a candidate for CendR-based therapy, the method comprising (a) exposing the tumor to a CendR element, and (b) determining if the CendR element penetrated the tumor, wherein a CendR element that penetrated identifies the tumor as being a candidate for CendR-based therapy. The tumor can be in an assay. The CendR element can be coupled to a protein or peptide. The CendR element can be an activatable CendR element. The activatable CendR element can be activated before exposure to the tumor. The activatable CendR element can be a protease-activatable CendR element. The protein or peptide can be circular. The CendR element can be at the C-terminal end of the protein or peptide.

Also disclosed are methods of producing an activatable CendR element that can be activated in proximity to a cell of interest, the method comprising forming an activatable CendR element wherein a blocking group is coupled to a CendR element via a cleavable bond, wherein the cleavable bond is cleavable by an enzyme present in proximity to the cell of interest. The cell can be in a subject. The enzyme that is present in proximity to the cell of interest can be identified. The enzyme that is present in proximity to the cell of interest can be identified prior to forming the activatable CendR element. The cleavable bond can be selected based on the enzyme that is present in proximity to the cell of interest. The cleavable bond can be selected prior to forming the activatable CendR element. The CendR element can comprise a terminal carboxyl group, wherein the blocking group is coupled to the terminal carboxyl group.

Also disclosed are methods of forming an activatable CendR element, the method comprising causing a blocking group to be covalently coupled to a CendR element, wherein a bond coupling the blocking group and the CendR element is cleavable. Also disclosed are methods of forming an activatable CendR element, the method comprising causing a blocking group to be covalently coupled to an amino acid sequence, wherein the amino acid sequence comprises a CendR element the CendR element, wherein a bond coupling the blocking group and the CendR element is cleavable. Also disclosed are methods of forming an activatable CendR element, the method comprising (a) selecting an amino acid sequence for internalization into a cell and/or penetration of tissue, wherein the amino acid sequence comprises a CendR element, and (b) causing a blocking group to be covalently coupled to the CendR element, wherein a bond coupling the blocking group and the CendR element is cleavable. The blocking group covalently coupled to the CendR element reduces or prevents internalization into a cell and/or penetration of tissue. The blocking group covalently coupled to the CendR element can reduce or prevent internalization into a cell and/or penetration of tissue compared to the same CendR element with no blocking group. The activatable CendR element can comprise the selected amino acid sequence and the blocking group. The cell can be in a subject. The enzyme that is present in proximity to the cell of interest can be identified. The enzyme that is present in proximity to the cell of interest can be identified prior to forming the activatable CendR element. The cleavable bond can be selected based on the enzyme that is present in proximity to the cell of interest. The cleavable bond can be selected prior to forming the activatable CendR element. The CendR element can comprise a terminal carboxyl group, wherein the blocking group is coupled to the terminal carboxyl group. A cargo composition can be covalently coupled or non-covalently associated with a protein or peptide comprising the selected amino acid sequence. The cargo composition can be coupled or associated with the protein or peptide on the N terminal side of the CendR element.

Disclosed herein is a method of forming a CendR conjugate, the method comprising selecting an amino acid sequence for internalization into a cell, wherein the amino acid sequence comprises a C-terminal element, and causing a cargo composition to be covalently coupled or non-covalently associated with a protein or peptide comprising the selected amino acid sequence, wherein the selected amino acid sequence is at the C-terminal end of the protein or peptide, wherein the CendR conjugate comprises the protein or peptide and the coupled or associated cargo composition.

Disclosed is a method of making a CendR conjugate comprising: (a) selecting an amino acid sequence for internalization into a cell, wherein the amino acid sequence comprises a C-terminal element, (b) causing a cargo composition to be covalently coupled or non-covalently associated with a protein or peptide comprising the selected amino acid sequence, wherein the selected amino acid sequence is at the C-terminal end of the protein or peptide, wherein the CendR conjugate comprises the protein or peptide and the coupled or associated cargo composition.

Also disclosed is a method of delivering a cargo composition into a cell, the method comprising: (a) coupling a CendR element to the cargo composition thus forming a CendR conjugate; and (b) exposing the cell to the CendR conjugate, wherein the CendR conjugate can then enter the cell, thereby delivering the cargo composition into the cell.

Also disclosed is a method of causing a cargo composition to penetrate tissue, the method comprising: (a) coupling a CendR element to the cargo composition, thus forming a CendR conjugate; and (b) exposing the tissue to the CendR conjugate, wherein the CendR conjugate can then enter and exit cells in the tissue, thereby causing the cargo composition to penetrate the tissue.

Further disclosed is a method of delivering a cargo composition into a cell, the method comprising: (a) coupling an activatable CendR element to the cargo composition thus forming a CendR conjugate; and (b) exposing the cell to the CendR conjugate, whereupon a cleaving agent activates the activatable CendR element of the CendR conjugate, wherein the CendR conjugate can then enter the cell, thereby delivering the cargo composition into the cell.

Further disclosed is a method of causing a cargo composition to penetrate tissue, the method comprising: (a) coupling an activatable CendR element to the cargo composition thus forming a CendR conjugate; and (b) exposing the tissue to the CendR conjugate, whereupon a cleaving agent activates the activatable CendR element of the CendR conjugate, wherein the CendR conjugate can then enter and exit cells in the tissue, thereby causing the cargo composition to penetrate the tissue.

Also disclosed is a method of identifying a cell that can internalize a CendR element, the method comprising: (a) exposing a cell to a CendR element; and (b) determining if the CendR element was internalized. The cell can be in an assay, for example. The CendR element can be coupled to a cargo composition, such as, for example, a protein or peptide, thereby forming a CendR conjugate.

Also disclosed is a method of identifying a cell that can internalize an activatable CendR element, the method comprising: (a) exposing a cell to an activatable CendR element; (b) determining if the activatable CendR element was internalized. The activatable CendR element can be unblocked before exposure to the cell, but does not need to be. This can be used to test the blocking ability of the blocker, for example. The activatable CendR element can also be a protease-activated CendR element.

Also disclosed is a method of identifying a cancer cell as a candidate for CendR-based therapy, the method comprising: (a) exposing the cancer cell to a CendR element; and (b) determining if the CendR element was internalized by the cancer cell, wherein an internalized CendR element identifies the cancer cell as being a candidate for CendR-based therapy. The cell can be in an assay, or can be in a subject, for example. The CendR element can be coupled to a cargo composition, such as, for example, a protein or peptide, thereby forming a CendR conjugate.

Also disclosed is a method of identifying a tumor as a candidate for CendR-based therapy, the method comprising: (a) exposing tissue from the tumor to a CendR element; and (b) determining if the CendR element passed through the tissue or was internalized by cells in the tissue, wherein a passed-through or internalized CendR element identifies the tumor as being a candidate for CendR-based therapy.

Also disclosed is a method of producing an activatable CendR element that can be activated in proximity to a cell of interest, the method comprising forming an activatable CendR element wherein a blocking group is coupled to a CendR element via a cleavable bond, wherein the cleavable bond is cleavable by an enzyme present in proximity to the cell of interest. This can further comprise, prior to forming the activatable CendR element, identifying the enzyme that is present in proximity to the cell of interest. This can further comprise, prior to forming the activatable CendR element, selecting the cleavable bond based on the enzyme that is present in proximity to the cell of interest.

Also disclosed is a method of forming an activatable CendR element, the method comprising: (a) selecting an amino acid sequence for internalization into a cell, wherein the amino acid sequence comprises a C-terminal element, wherein the C-terminal element comprises a terminal carboxyl group, and (b) causing a blocking group to be covalently coupled to the terminal carboxyl group of the selected amino acid sequence, wherein the bond coupling the blocking group and the terminal carboxyl group is cleavable, wherein the activatable CendR element comprises the selected amino acid sequence and the blocking group. This can further comprise, prior to step (b), selecting the bond coupling the blocking group and the terminal carboxyl group to be cleavable by a protease present in proximity to the cell of interest.

Further disclosed is an activatable CendR element made by the method comprising (a) selecting an amino acid sequence for internalization into a cell, wherein the amino acid sequence comprises a C-terminal element, wherein the C-terminal element comprises a terminal carboxyl group, and (b) causing a blocking group to be covalently coupled to the terminal carboxyl group of the selected amino acid sequence, wherein the bond coupling the blocking group and the terminal carboxyl group is cleavable, wherein the activatable CendR element comprises the selected amino acid sequence and the blocking group. The method can further comprise, prior to step (b), selecting the bond coupling the blocking group and the terminal carboxyl group to be cleavable by a protease present in proximity to the cell of interest.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 1A, 1B and 1C show the identification of internalizing peptides. FIG. 1A: For T7 phage display, peptides were expressed as C-terminal fusion with the major capsid protein GP10. FIG. 1B: 3 rounds of ex vivo selection of four different libraries (CX7C, X7, RXXRXXX (SEQ ID NO: 19) and RXXR(A/P)PRXXX (SEQ ID NO: 20)) were performed on PPC1 cells, resulting in phage pools homing 500-2,500 fold over control phage displaying 7 consecutive glycine residues (G7). FIG. 1C: Sequencing of random 20 phage clones per library revealed a dominant presence of peptides terminating with C-terminal arginine residue, independent of the initial library configuration and the temperature used during the interaction of the phage with the cells. The sequences correspond to SEQ ID NOs: 52-61, 132, 72-75, 133, 76, 134, 77-78, 135-144 and 62-71 from the top left of the table to the bottom right for the section corresponding to 4° C. The sequences correspond to SEQ ID Nos 82-91, 102-111, 145-154 and 92-101 from the top left of the table to the bottom right for the section corresponding to 37° C.+acid wash.

FIGS. 2A and 2B show that T7 phage displaying a C-terminal arginine binds to and is internalized by PPC1 cells. FIG. 2A: Binding of T7 phage to prostate cancer cells depends on the display of a C-terminal arginine on the phage particles. PPC1 cells were incubated with T7 bacteriophage displaying derivatives of the G7 (upper graph) or RPARPAR peptide (SEQ ID NO: 2) (lower graph) at 4° C., and the bound phage was quantified by plaque assay. Binding is expressed in fold over of the non-binding G7 control phage. FIG. 2B: Phage displaying C-terminal arginine is internalized into cultured PPC1 cells (arrow, nuclear internalization; arrowhead, cytoplasmic internalization). A panel of T7 phage clones were incubated at 37° C. with PPC1 cells grown on collagen-coated coverslips, stained with anti T7 antibody and imaged by confocal microscopy.

FIG. 8A: Truncated versions of iRGD phage were made and tested for internalization into PPC1 human prostate cancer cells. Phage bearing CRGDKG (SEQ ID NO: 21), CRGDK (SEQ ID NO: 22), CR (SEQ ID NO: 163) have a higher ability to internalize into PPC1 cells compared to the native iRGD phage. Sequences are, from left to right, SEQ ID NO: 155, SEQ ID NO: 4, SEQ ID NO: 157, SEQ ID NO: 158, SEQ ID NO: 159, SEQ ID NO: 160, SEQ ID NO: 21, SEQ ID NO: 22, SEQ ID NO: 161, SEQ ID NO: 162, SEQ ID NO: 163. FIG. 8B: PPC1 cells were pre-incubated with or without various concentrations of UV-inactivated phage bearing iRGD, CRGDK (SEQ ID NO: 22), CR (SEQ ID NO: 163), or RPAR (SEQ ID NO: 164), followed by further incubation with live CRGDK phage or a control phage (NC5). Note that CRGDK (SEQ ID NO: 22) phage internalization was inhibited by RPAR phage in a dose-dependent fashion indicating that CRGDK (SEQ ID NO: 22) acts as a CendR.

FIGS. 10A and 10B show the identification of CendR peptides using phage display. A panel of peptide libraries (CX7C, X7 and RXXRXXX (SEQ ID NO:19)) was used for ex vivo selection on cell suspensions derived from PPC-1 orthotopic xenograft tumors. (FIG. 10A) After three rounds of selection, phage pools bound to the tumor cells in suspensions 500-1,300 fold over the control polyglycine heptapeptide (G7) phage. (FIG. 10B) Representative peptide sequences recovered after three rounds of selection of phage. Peptides ending with C-terminal arginine comprised 97% of all phage inserts sequenced. The sequences correspond to SEQ ID NOs: 52-81 from the top left of the table to the bottom right for the section corresponding to 4° C. The sequences correspond to SEQ ID NOs: 82-111 from the top left of the table to the bottom right for the section corresponding to 37° C.+acid wash.

FIG. 11A: Interaction of G6R and RPARPAR (SEQ ID NO:2) phage with the PPC-1 cells. Cells were incubated with phage at 4° C. to assess surface binding ("bound") or at 37° C. followed by a wash at low pH to assess phage uptake ("internalized"). RPARPAR (SEQ ID NO:2)-functionalized qdots inhibited both the binding and internalization of RPARPAR phage, whereas G7 qdots had no effect. G6R phage was not internalized; its binding to PPC-1 cells was blocked by the excess of RPARPAR (SEQ ID NO:2) qdots. Binding is expressed as fold control phage displaying polyglycine heptapeptide (G7). FIG. 11B: Binding RPARPAR (SEQ ID NO: 2) derivative phage to the PPC-1 cells at 4° C. The data are representative of 4 independent binding experiments. From left to right the sequences corresponds to SEQ ID NOs: 112-125, except the first and ninth sequence which is SEQ ID NO:2 and SEQ ID NO:3 respectively. Statistical analysis was performed by Student's t-test (FIG. 11A). n=3; error bars indicate s.d.; single asterisk, p<0.05; double asterisk, p<0.01. Scale bars: 20 μm. FIG. 11C (panels c-g) Confocal microscopy of PPC-1 cells incubated for 2 hours at 37° C. with peptide-displaying phage (bright colored dots, c-e) or peptide-coated qdots (bright colored dots, f, g): RPARPAR (SEQ ID NO:2) T7 (c), G6R T7 (d), RPARPARA (SEQ ID NO:2) T7 (e), RPARPAR (SEQ ID NO:2) q-dots (f), and RPARPAR-$NH_2$ (SEQ ID NO:2) qdots (g). In microphotographs, arrowheads point at surface-bound phage and q-dots; arrows point at internalized particles.

FIGS. 12A and 12B show the cellular binding and uptake of RPARPAR (SEQ ID NO: 2), RGERPPR (SEQ ID NO:27) and RVTRPPR (SEQ ID NO:28) peptides. FIG. 12A: shared pathway. Phage displaying all three tandem RXXR (SEQ ID NO:25) peptides bound to the PPC-1 cells at 4° C. at a similar extent. The binding was inhibited by preincubating the cells with RPARPAR (SEQ ID NO:2)-functionalized qdots. Qdots coated with heptaglycine control peptide (G7) did not have an effect on the phage binding. Statistical analysis was performed by Student's t-test (c). n=3; error bars indicate s.d.; single asterisk, p<0.05; double asterisk, p<0.01. FIG. 12B (panels b-i): Confocal immunofluorescence assessment of phage immunoreactivity (bright colored dots) in PPC-1 cells cultured for 1 hour in the presence of $10^9$ pfu of the following phage: (b) RPARPAR (SEQ ID NO:2), (c) RGERPPR (SEQ ID NO:27), (d) RVTRPPR (SEQ ID NO:28), (e) control G7, (f) RPARPAR (SEQ ID NO: 2) phage in the presence of 20 μM free RPARPAR (SEQ ID NO:2) peptide, (g) RPARPAR (SEQ ID NO:2) phage in the presence of 200 μM free RPARPAR (SEQ ID NO: 2) peptide, (h) RPARPAR (SEQ ID NO:2) phage in the presence of 2 mM free RPARPAR (SEQ ID NO:2) peptide, (i) RGERRPR (SEQ ID NO:27) phage in the presence of 200 μM free RPARPAR (SEQ ID NO:2) peptide. Egg-shaped ovals represent nuclear counterstaining with DAPI. Scale bars: 20 μm.

FIG. 15A: Binding of RPARPAR (SEQ ID NO:2) phage to the cultured cells at 4° C. in vitro. FIG. 15B: Binding of RPARPAR (SEQ ID NO:2) phage to primary cell suspensions of mouse organs at 4° C. ex vivo. FIGS. 15C and 15D: Tissue distribution of intravenously injected RPARPAR (SEQ ID NO:2) phage after 20 minutes of circulation time. FIG. 15C: Phage was quantified by titration, tissue binding is expressed as fold G7 phage. Statistical analysis was performed by Student's t-test (c). n=3; error bars indicate s.d.; double asterisk, p<0.01, triple asterisk, p<0.001. FIG. 15D (panels d and e): Immunofluorescence localization of T7 phage (light coloring) in lung sections of mice injected intravenously with RPARPAR (SEQ ID NO:2) (d) or G7 (e) phage. Widespread immunoreactivity is present in the lungs of mice injected with RPARPAR (SEQ ID NO:2) (arrowheads in d) but not G7 (with occasional labeling seen in vessels, arrows in e). Scale bar: 50 μm.

FIG. 16A: At 4° C., phage binding to cultured PPC-1 cell suspension plateaus at 20 minutes. For the time course study, cell suspension of cultured PPC-1 cells was incubated with $10^9$ pfu of phage followed by one-step separation of cells from unbound phage by centrifugation on silicone oil cushion (1.03 g/ml) and titration. FIG. 16B (panels b, c): Internalization of RPARPAR (SEQ ID NO:2) functionalized qdots by live PPC-1 cells at 37° C. (b) After 15 minutes of addition of qdots, labeling (light colored specks) is seen along the plasma membrane. (c) At 1 hour, most of the q-dots are internalized. Nuclei were stained with intravital nuclear stain Hoechst 342. n=3; error bars indicate s.d. Scale bars: 20 μm.

FIG. 17A: Effect of endocytosis inhibitors on RPARPAR (SEQ ID NO:2) phage internalization. Phage was incubated with PPC-1 cells in the presence of the indicated inhibitors for 90 minutes at 37° C. followed by acid wash and titration to quantify the internalized phage. Statistical analysis performed by ANOVA showed that none of the inhibitors significantly inhibited the internalization. n=3; error bars indicate s.d. FIG. 17B: Confocal imaging of PPC-1 cells incubated for 60 minutes in the presence of $10^9$ pfu of RPARPAR (SEQ ID NO:2) phage and double stained for T7 phage and subcellular compartment markers (LAMP-1, caveolin-1, calnexin, EEA-1). Nuclei were stained with DAPI. FIG. 17C: Confocal imaging of PPC-1 cells incubated for 180 minutes in the presence of $10^9$ pfu of RPARPAR (SEQ ID NO:2) phage and 10 μg/ml of cholera toxin B subunit. Phage was detected by Alexa-546 labeled secondary antibody and cholera toxin subunit B was labeled with Alexa-488 dye. Colocalization is represented by the bright spots (arrows) just outside of the nucleus. Nuclei were stained with DAPI. Scale bars: 10 μm.

FIGS. 18A-18C show the identification and validation of NRP-1 as the CendR receptor. FIG. 18A: Affinity chromatography of proteins interacting with RPARPAR (SEQ ID NO: 2) peptide. PPC-1 tumor tissue was extracted with a 200 mM glucopyranoside buffer, and the extract was incubated with RPARPAR-coated (SEQ ID NO:2) beads, followed by extensive washes, and elution with 2 mM free RPARPAR (SEQ ID NO:2) peptide. Note appearance of a 130 kDa band, identified by mass spectroscopy as NRP-1, starting in the fraction 3 of the eluate. Upper panel—a silver stained gel, lower panel—an immunoblot with anti-NRP-1 antibody. FIG. 18B: Binding of RPARPAR (SEQ ID NO:2) phage to M21 melanoma cells transiently transfected with wild-type NRP-1 (NRP-1), triple mutant NS346A-E348A-T349A NRP-1 (Mutant NRP-1), or parental pcDNA3.1plasmid (Vector), and to non-transfected M21 cells. FIG. 18C: (c, d), Confocal immunofluorescence images of NRP-1 and RPARPAR (SEQ ID NO:2) T7 phage in PPC-1 cells incubated with phage at 37° C. for 40 minutes (c) and 3 hours (d). The phage and NRP-1 co-localize extensively, but there appears to be a progressive decrease in the overlap (arrowheads in c and d) and appearance of structures positive for the phage only (arrows, d). (e) Immunostaining and confocal imaging of RPARPAR (SEQ ID NO:2) phage and NRP-1 in M21 cells transiently transfected with NRP-1. RPARPAR (SEQ ID NO:2) phage was incubated with cells cultured on fibronectin-coated coverslips for 3 hours at 37° C. Only NRP-1-expressing cells bind and internalize the phage (arrows), whereas negative cells (not visible) do not. (f) RPARPARA (SEQ ID NO:3) phage is not internalized into NRP-1-positive M21 cells. Statistical analysis was performed with ANOVA (b); n=3; error bars indicate s.d. Scale bars: 10 μm.

FIG. 19A: Known NRP-1 ligands cause phage binding to the PPC-1 cells. Phage displaying peptide ligands known to interact with b1 subunit of NRP-1 (table in a) bind to the cells to a similar extent as the RPARPAR (SEQ ID NO:2), whereas VEGF-C7 with added C-terminal alanine (VEGF-C7-A) is inactive. In the table from top to bottom the sequences correspond to SEQ ID NOs: 126-130. FIG. 19B (panels b-g): Confocal immunofluorescence assessment of phage immunoreactivity in PPC-1 cells cultured for 1 hour in the presence of $10^9$ pfu of the indicated phage. Arrows, internalized phage; arrowheads, plasma membrane-associated phage. Nuclei were stained with DAPI. Insets: competition of the phage binding by 0.5 mM free RPARPAR (SEQ ID NO:2) peptide (added to the cells 10 minutes prior to adding the phage). Scale bar: 20 μm.

FIG. 20A: The design of a uPA-activatable CendR peptide (uCendR). A uPA consensus cleavage site SGRSA (amino acids 5-9 of SEQ ID NO:34) (Ke, S. H. et al. (1997) was combined with an overlapping CendR element. In the intact peptide, the CendR element is inactive as it is not exposed at the C-terminus. Cleavage by uPA leads to C-terminal exposure of the CendR element (uCendR-X), cell binding and internalization. FIG. 20B: Binding to PPC-1 cells of phage displaying the uCendR peptide and a peptide corresponding to post-cleavage product (uCendR-X) to the PPC-1 cells. Prior to adding the phage to the cells, it was treated with 50 iu of uPA, 25 μg of crystalline trypsin, 50 iu of thrombin, or 25 μg of collagenase type I. FIG. 20C (panels c-e) Fluorescent microscopy of PPC-1 cells incubated with uPA-CendR-qdots. Untreated uCendR qdots are not internalized (c), whereas uPA treatment triggers internalization of the q-dots (d, arrowheads). Amiloride inhibited uptake (e). Statistical analysis was performed with ANOVA (b); n=3; error bars indicate s.d.; triple asterisk, p<0.001. Scale bars: 20 μm.

DETAILED DESCRIPTION OF THE INVENTION

Figure 2B:
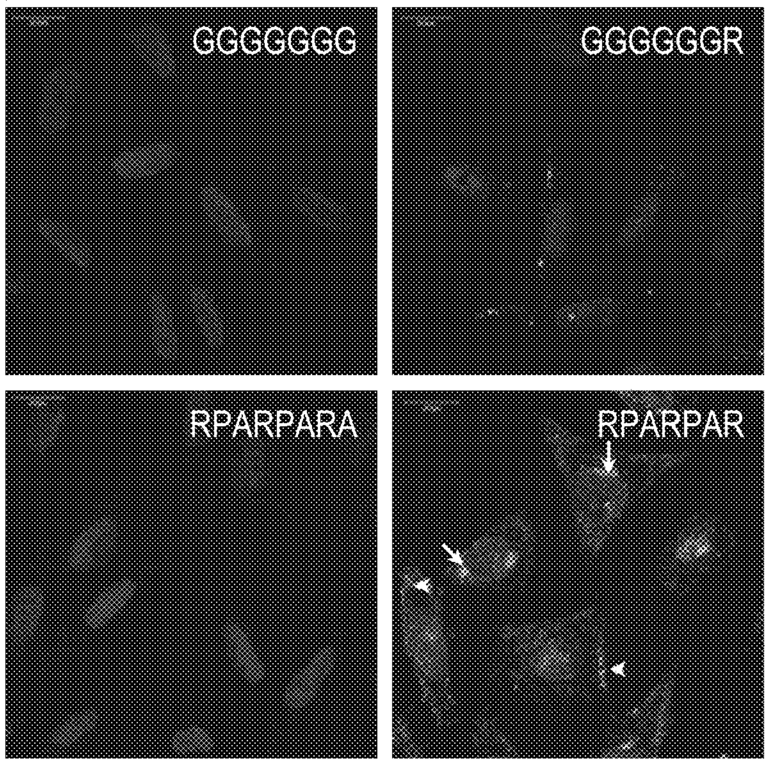

The disclosed method and compositions can be understood more readily by reference to the following detailed description of particular embodiments and the Example included therein and to the Figures and their previous and following description.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

B. General

Figure 9:
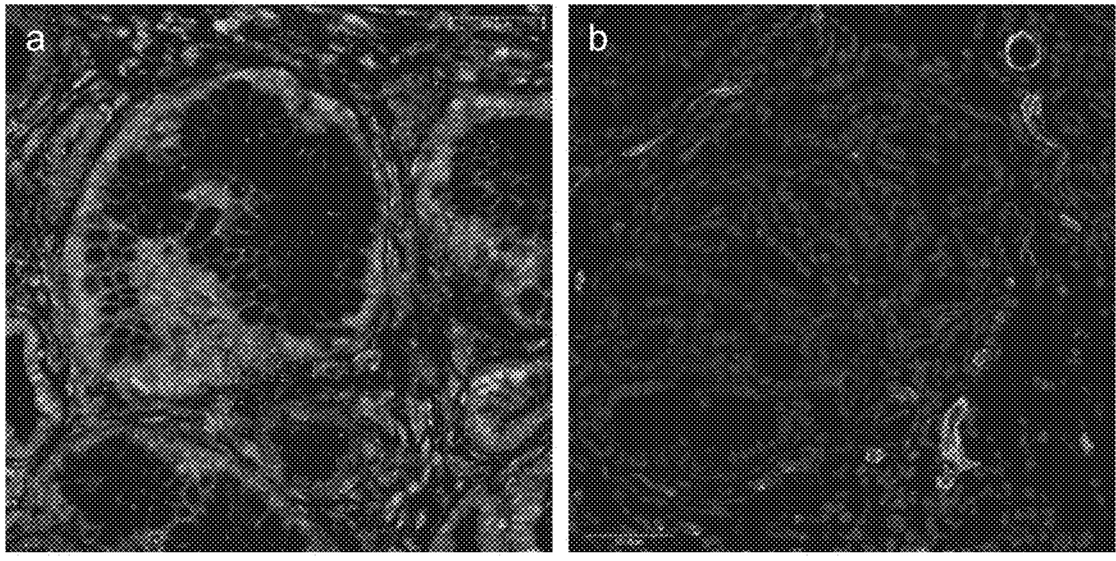
FIG. 9 shows that iRGD is capable of spreading into tumor tissues. iRGD phage (a) and its control, KGD phage (b) were injected into transgenic mice bearing spontaneous pancreatic ductal adenocarcinoma, and were allowed to circulate for 15 min. The mice were than perfused with PBS containing 1% BSA, and the tumors were harvested. Cryosections of the tumors were stained with an anti-T7 phage antibody, an anti CD31 antibody, and DAPI. Note that iRGD phage is extensively taken up by the tumor cells forming the pancreatic tumor ducts, while KGD phage stays inside of some blood vessels and almost no signal is observed in the tumor ducts, showing that iRGD phage is capable of extravasating and spreading into the tumor tissue. Staining is denoted by the bright coloring in both panels of FIG. 9.

Disclosed herein is a new technological platform that enables intracellular delivery, exit and tissue penetration of compositions. The delivery can be general and can be targeted to cells or tissues of interest, such as tumors. Internalization of compositions (including nanoparticles, drugs, detectable markers, and other compounds) and their payload into target cells and penetration into target tissue can increase the efficiency of the targeting, but cell type-specific internalization and tissue type-specific penetration has not previously been achievable. In addition, the ability of compositions to penetrate into the extravascular space is a major factor limiting the targeting efficacy of compositions in vivo. A simple peptide motif, with a C-terminal element as a defining feature, has been identified that signals highly efficient internalization of phage and free peptides into cells (FIG. 9 is an example). This internalization phenomenon has been named the "C-end rule" or "CendR". Proteolysis that uncovers a C-terminal element can serve as a switch that triggers the internalization signal. Various compositions can be internalized through this mechanism. For example, homing peptide-mediated accumulation can occur at a target site with cell type-specific proteolysis that exposes a C-terminal element which allows for highly specific homing systems with target-triggered internalization. The CendR pathway can also be used for exit of compositions of interest from cells and their spread into tissue. The C-terminal element can cause translocation through vascular walls (and can be spread into tumor tissue from an intravenous injection, for example), and can also extend to other barriers, such as mucous membranes and the blood-brain barrier. As used herein, "tissue penetration" and "penetration of tissue" refer to passage into or through a tissue beyond or through the outer or a first layer of cells or through a tissue membrane. Such passage or penetration through tissue (which can also be referred to as extravasation and tissue penetration) can be a function of both cell internalization and exit functions. Throughout this application, when the term "tissue penetration" is used, it is understood that such penetration can also extend to other barriers and membranes found throughout the body, such as the blood brain barrier.

Unlike the known cell-penetrating peptides, the disclosed internalizing element is position-dependent—it is inactive when present in positions other than the C-terminus of the peptide. The latent peptide can be activated by cleavage by, for example, the appropriate proteolytic enzyme to expose, for example, a C-terminal arginine, lysine, or lysine-glycine. Throughout the application, when the term "CendR element" or "C-terminal element" is used, it is used to describe a C-terminal arginine, a C-terminal lysine, or a C-terminal lysine-glycine pair, where glycine is at the furthest C-terminal position. In other words, in the case where a lysine is on the C terminus end, the CendR element can remain functional with a glycine on the C terminus side of the lysine. However, it is not necessary to have glycine on the end in order for the lysine residue to be functional as a C-terminal element, so that lysine can be present without glycine and still be functional. The converse is not true, however, in that glycine cannot function as a C-terminal element without the presence of lysine adjacent to it. Arginine does not require either lysine or glycine to function as a C-terminal element, as long as it remains in the furthest C-terminal position. Such CendR elements can be referred to as type 1 CendR elements.

The term "CendR element" or "C-terminal element" can also be used to describe a C-terminal histidine and amino acid sequences having the sequence $X_1X_2X_3X_4$, where $X_1$ can be R, K or H, where $X_4$ can be R, K, H, or KG, and where $X_2$ and $X_3$ can each be, independently, any amino acid. Such CendR elements can be referred to as type 2 CendR elements. The $X_2$ and $X_3$ amino acids can be selected for specific purposes. For example, $X_2$, $X_3$, or both can be chosen to form all or a portion of a protease recognition sequence. This would be useful, for example, to specify or enable cleavage of a peptide having the CendR element as a latent or cryptic CendR element that is activated by cleavage following the $X_4$ amino acid. Examples of such amino acid choices are shown in Tables 1 and 4. The $X_1$, $X_2$ and $X_3$ amino acids can also be selected, for example, to recruit additional proteins to NRP-1 molecules at the cell surface. This can be applied, for example, to modulate the selectivity and internalization and/or tissue penetration potency of CendR elements (and the conjugates, proteins, and peptides containing CendR elements). Optionally, certain amino acids can also be excluded from use for $X_2$, $X_3$, or both. For example, if desired, G and D can be excluded from simultaneous use as $X_2$ and $X_3$, respectively. Some type 2 CendR elements can also be described as R/K/HXXR/K/H (SEQ ID NO:50) and R/K/HXXKG (SEQ ID NO: 51).

Examples of CendR elements include XXR/K/H, XXR/K, XXR/H, XXK/H, XXR, XXK, XXH, XXKG, RXXR/K/H, RXXR/K, RXXR/H, RXXK/H, RXXR, RXXK, RXXH, RXXKG, KXXR/K/H, KXXR/K, KXXR/H, KXXK/H, KXXR, KXXK, KXXH, KXXKG, HXXR/K/H, HXXR/K, HXXR/H, HXXK/H, HXXR, HXXK, HXXH, HXXKG, R/K/HXXR, R/KXXR, R/HXXR, K/HXXR, RXXR, KXXR, HXXR, R/K/HXXK, R/KXXK, R/HXXK, K/HXXK, RXXK, KXXK, HXXK, R/K/HXXH, R/KXXH, R/HXXH, K/HXXH, RXXH, KXXH, HXXH, R/K/HXXKG, R/KXXKG, R/HXXKG, K/HXXKG, RXXKG, KXXKG, and HXXKG.

This protease-controllable internalization system can be useful in engineering compositions with functions such as cell type-specific and/or tissue type-specific uptake and the ability to spread the compositions in tissues. In addition, this rule can be relevant for a multitude of biological processes, including viral infection and phagocytosis. As viruses can naturally use the CendR pathway for infecting the cells, the CendR peptides and/or conjugates can be useful for interfering with the process of viral infection.

In one example, the CendR peptides can be used in nanomedicine. One of the main goals of nanomedicine is to design devices that surpass simple drugs by performing multiple functions in diagnosing, monitoring, and treating disease. New technologies can be applied to solve some of the main problems in the medical uses of multifunctional nanoparticles. A major goal of medical nanotechnology is to develop nanodevices capable of monitoring disease in tissues, including the interior of cells. Such a device can involve a nanoparticle that, having sampled the interior of a cell, returns to report back on the findings. This requires an ability to exit cells. A number of cytoplasmic proteins that lack a signal sequence for secretion are nonetheless secreted from the cell. A prime example of a cellular protein that behaves in this manner is basic FGF (Backhaus et al., 2004). The VP22 protein also exits cells in an unconventional manner. Endowing nanoparticles with exit signals for non-targeted cells can reduce non-specific toxicity of the particles. Tissue-penetrating phage libraries can be used to identify molecular signals that promote nanoparticle exit from cells.

1. CendR Elements and their Uses

Disclosed herein is a method of forming a CendR conjugate, the method comprising selecting an amino acid sequence for internalization into a cell and/or penetration of tissue, wherein the amino acid sequence comprises a C-terminal element, and causing a cargo composition to be covalently coupled or non-covalently associated with a protein or peptide comprising the selected amino acid sequence, wherein the selected amino acid sequence is at the C-terminal end of the protein or peptide, wherein the CendR conjugate comprises the protein or peptide and the coupled or associated cargo composition.

As defined herein, a C-terminal element is either an arginine, a lysine, or a lysine-glycine (for a type 1 CendR element), or a histidine or an amino acid sequence having the sequence $X_1X_2X_3X_4$, where $X_1$ can be R, K or H, where $X_4$ can be R, K, H, or KG, and where $X_2$ and $X_3$ can each be, independently, any amino acid (for a type 2 CendR element).

As used herein, “selecting an amino acid sequence for internalization into a cell” refers to selecting, identifying designing or otherwise categorizing an amino acid sequence with the specific intention of obtaining entry into a cell of a protein or peptide that is comprised of the amino acid sequence. Thus, for example, selecting an amino acid sequence for some purpose or capability other than obtaining entry into a cell of a protein or peptide that is comprised of the amino acid sequence and in the absence of an intention of obtaining entry into a cell of a protein or peptide that is comprised of the amino acid sequence does not constitute “selecting an amino acid sequence for internalization into a cell.” Selecting an amino acid sequence for some purpose or capability as well as for obtaining entry into a cell of a protein or peptide that is comprised of the amino acid sequence does constitute “selecting an amino acid sequence for internalization into a cell.” Thus, the presence of additional goals or purposes does not alter that selection of an amino acid sequence at least with the specific intention of obtaining entry into a cell of a protein or peptide that is comprised of the amino acid sequence constitutes “selecting an amino acid sequence for internalization into a cell.”

As used herein, “selecting an amino acid sequence for penetration of tissue” refers to selecting, identifying designing or otherwise categorizing an amino acid sequence with the specific intention of obtaining entry into tissue (that is, tissue penetration) of a protein or peptide that is comprised of the amino acid sequence. Thus, for example, selecting an amino acid sequence for some purpose or capability other than obtaining entry into tissue of a protein or peptide that is comprised of the amino acid sequence and in the absence of an intention of obtaining entry into tissue of a protein or peptide that is comprised of the amino acid sequence does not constitute “selecting an amino acid sequence for penetration of tissue.” Selecting an amino acid sequence for some purpose or capability as well as for obtaining entry into tissue of a protein or peptide that is comprised of the amino acid sequence does constitute “selecting an amino acid sequence for penetration of tissue.” Thus, the presence of additional goals or purposes does not alter that selection of an amino acid sequence at least with the specific intention of obtaining entry into tissue of a protein or peptide that is comprised of the amino acid sequence constitutes “selecting an amino acid sequence for penetration of tissue.”

As used herein, “selecting an amino acid sequence for internalization into a cell and/or penetration of tissue” refers to selecting, identifying designing or otherwise categorizing an amino acid sequence with the specific intention of obtaining entry into either or both a cell and tissue of a protein or peptide that is comprised of the amino acid sequence. Thus, for example, selecting an amino acid sequence for some purpose or capability other than obtaining entry into a cell, tissue, or both of a protein or peptide that is comprised of the amino acid sequence and in the absence of an intention of obtaining entry into a cell, tissue, or both of a protein or peptide that is comprised of the amino acid sequence does not constitute “selecting an amino acid sequence for internalization into a cell and/or penetration of tissue.” Selecting an amino acid sequence for some purpose or capability as well as for obtaining entry into either or both a cell and tissue of a protein or peptide that is comprised of the amino acid sequence does constitute “selecting an amino acid sequence for internalization into a cell and/or penetration of tissue.” Thus, the presence of additional goals or purposes does not alter that selection of an amino acid sequence at least with the specific intention of obtaining entry into a cell, tissue, or both of a protein or peptide that is comprised of the amino acid sequence constitutes “selecting an amino acid sequence for internalization into a cell and/or penetration of tissue.”

As used herein, “causing a cargo composition to be covalently coupled or non-covalently associated” with something else refers to any action that results in a cargo composition that is not covalently coupled or non-covalently associated with the something else becoming or coming into the state of being covalently coupled or non-covalently associated with the something else. As an example, covalently coupling a cargo composition to another cargo composition constitutes “causing a cargo composition to be covalently coupled or non-covalently associated” with the other cargo composition. As another example, a cargo composition that starts as a nonexistent concept and then is synthesized as part of a composition that includes the thing to which the cargo composition is to be coupled or associated constitutes “causing a cargo composition to be covalently coupled or non-covalently associated” with the thing. For example, synthesis of a peptide that includes both an amino acid sequence of interest and an amino acid sequence comprising a C-terminal element constitutes causing a cargo composition (the amino acid sequence of interest) to be covalently coupled or non-covalently associated with the amino acid sequence comprising a C-terminal element. However, and in general, synthesis of a protein or peptide that naturally includes both the amino acid sequence of interest and an amino acid sequence comprising a C-terminal element can be excluded as a process of "causing a cargo composition to be covalently coupled or non-covalently associated" with the amino acid sequence comprising a C-terminal element.

As used herein, "CendR element" refers to an amino acid sequence having a C-terminal arginine, lysine, or lysine-glycine sequence (for a type 1 CendR element), or a C-terminal histidine or a C-terminal amino acid sequence having the sequence $X_1X_2X_3X_4$, where $X_1$ can be R, K or H, where $X_4$ can be R, K, H, or KG, and where $X_2$ and $X_3$ can each be, independently, any amino acid (for a type 2 CendR element). Some type 2 CendR elements can also be described as R/K/HXXR/K/H (SEQ ID NO:50) and R/K/HXXKG (SEQ ID NO: 51). The $X_1$, $X_2$ and $X_3$ amino acids can also be selected to recruit additional proteins to NRP-1 molecules at the cell surface. This can be applied, for example, to modulate the selectivity and internalization and/or tissue penetration potency of CendR elements (and the conjugates, proteins, and peptides containing CendR elements). A CendR element can, for example, comprise a protein or peptide comprising an amino acid sequence having a C-terminal element, comprise a protein or peptide consisting of an amino acid sequence having a C-terminal element, or consist of an amino acid sequence having a C-terminal element. Optionally, certain amino acids can also be excluded from use for $X_2$, $X_3$, or both in CendR elements of the form $X_1X_2X_3X_4$. For example, if desired, G and D can be excluded from simultaneous use as $X_2$ and $X_3$, respectively.

Examples of CendR elements include XXR/K/H, XXR/K, XXR/H, XXK/H, XXR, XXK, XXH, XXKG, RXXR/K/H, RXXR/K, RXXR/H, RXXK/H, RXXR, RXXK, RXXH, RXXKG, KXXR/K/H, KXXR/K, KXXR/H, KXXK/H, KXXR, KXXK, KXXH, KXXKG, HXXR/K/H, HXXR/K, HXXR/H, HXXK/H, HXXR, HXXK, HXXH, HXXKG, R/K/HXXR, R/KXXR, R/HXXR, K/HXXR, RXXR, KXXR, HXXR, R/K/HXXK, R/KXXK, R/HXXK, K/HXXK, RXXK, KXXK, HXXK, R/K/HXXH, R/KXXH, R/HXXH, K/HXXH, RXXH, KXXH, HXXH, R/K/HXXKG, R/KXXKG, R/HXXKG, K/HXXKG, RXXKG, KXXKG, and HXXKG.

A CendR element that can be internalized into a cell can be referred to as an internalization CendR element. A CendR element that can penetrate tissue can be referred to as a penetrating CendR element. A CendR element that can be internalized into a cell and that can penetrate tissue can be referred to as an internalization and penetrating CendR element. Unless the context clearly indicates otherwise, reference to "CendR element" refers to any of these, either individually, collectively, or in any combination.

As used herein, "CendR conjugate" refers to a cargo composition associated with a protein or peptide comprising an amino acid sequence that comprises a CendR element where the amino acid sequence is at the C-terminal end of the protein or peptide.

As used herein, "activatable CendR element" refers to a CendR element having a molecule, moiety, nanoparticle, compound or other composition covalently coupled to the CendR element, such as to the terminal carboxyl group of the C-terminal element, where the molecule, moiety, nanoparticle, compound or other composition can block internalization and/or tissue penetration of the CendR conjugate and where the molecule, moiety, nanoparticle, compound or other composition can be removed (to expose the terminal carboxy group, for example). For example, the activatable CendR element can be on the C-terminal end of the peptide, and can prevent the CendR element from being internalized and/or from penetrating tissue. The molecule, nanoparticle, moiety, compound or other composition covalently coupled to the CendR element can be referred to as the "blocking group." For example, the blocking group can be coupled to the terminal carboxyl group of the C-terminal arginine or lysine or other C-terminal amino acid of the CendR element, to the C-terminal amino acid of the CendR element, or to an amino acid of the CendR element other than the C-terminal amino acid. The blocking group can also be coupled, or associated with a part of a CendR conjugate other than the CendR element so long as it can prevent the CendR element from being internalized and/or from penetrating tissue.

An activatable CendR element can be blocked from internalization into a cell, from tissue penetration, or both. Generally, an activatable CendR element will be blocked from both internalization into a cell and penetration of tissue. Such activatable CendR elements can be referred to as activatable internalization and penetrating CendR elements. However, some activatable CendR elements could be blocked only from tissue penetration or only from internalization into a cell. Such activatable CendR elements can be referred to as activatable internalization CendR elements (for CendR elements that are blocked only from internalization into a cell) or as activatable internalization and penetrating CendR elements (for CendR elements that are blocked only from penetration of tissue). Generally, internalization CendR elements that are activatable will be activatable internalization CendR elements. Similarly, penetrating CendR elements that are activatable generally will be activatable penetrating CendR elements. Internalization and penetrating CendR elements that are activatable will be activatable internalization and penetrating CendR elements. Removal of the blocking group will allow the CendR element to be internalized into a cell, penetrate tissue, or both.

A "protease-activatable CendR element" (or "protease-activated CendR element") refers to an activatable CendR element where the blocking group is coupled to the CendR element via a peptide bond and where the peptide bond can be cleaved by a protease. Cleavage of this peptide bond in a protease-activatable CendR element makes the CendR element capable of internalization into a cell and/or of tissue penetration. In one example, the blocking group can be coupled to the CendR element via a cleavable or labile bond. The cleavable bond can be cleaved by, for example, an enzyme or a chemical compound. Cleavage or 'labilization' bond in an activatable CendR element makes the CendR element capable of internalization into a cell and/or of tissue penetration. Such cleavage or 'labilization' can be referred to as activation of the CendR element. A protease-activatable CendR element is a form of activatable CendR element. The $X_2$ and $X_3$ amino acids of a CendR element of the form $X_1X_2X_3X_4$ can be selected for specific purposes. For example, $X_2$, $X_3$, or both can be chosen to form all or a portion of a protease recognition sequence. This would be useful, for example, to specify or enable cleavage of a peptide having the CendR element as a latent or cryptic CendR element that is activated by cleavage following the $X_4$ amino acid. Examples of such amino acid choices are shown in Tables 1 and 4. A useful class of CendR elements can consist of unblocked CendR elements and activatable CendR elements, which class excludes blocked CendR elements that are not activatable.

Useful proteases include enzymes that cleave on the C terminal side of basic residues (the C terminal residues of CendR elements can be basic residues) and enzymes that recognize sequence on the C terminal side of their cleavage site (thus allowing free choice of the C terminal sequence of the cleavage product). Examples of useful proteases include, for example, serine proteases (including, for example, plasmin and pasminogen activators), proprotein convertases (see, for example, Duckert et al., Prediction of proprotein convertase cleavage sites Protein engineering Design and Selection 17(1):107-112 (2004)), furins, and carboxypeptidases. Serine proteases are particularly useful for CendR elements and CendR conjugates targeted to cancer cells and tumors. Examples of enzymes that cleave on the C terminal side of basic residues include Arg-C protease (which cleaves on the C terminal side of arginine residues; Keil, Specificity of Proteolysis (Springer-Verlag, Berlin-Heidelberg-New York) (1992)), clostripain (which cleaves on the C terminal side of arginine residues; Keil, 1992), enterokinase (which cleaves after the sequence-Asp-Asp-Asp-Asp-Lys-; SEQ ID NO: 131), Factor Xa (which cleaves after the sequence-Gly-Arg-; Fujikawa et al., Activation of bovine factor X (Stuart factor): conversion of factor Xa alpha to factor Xa beta, Proc. Natl. Acad. Sci. 72:3359-3363 (1975)), Lys-C(which cleaves on the C terminal side of lysine residues; Keil, 1992), thrombin (which cleaves on the C terminal side of arginine residues; Keil, 1992), trypsin (which cleaves on the C terminal side of arginine and lysine residues; Keil, 1992), serine proteases, proprotein convertases (such as PC1, PC2, PC3, PC4, PC5, PC6, PC7, PC8, furin, Pace, PACE4, Site 1 protease, SIP, SKI, NARC-1, PCSK1, PCSK2, PCSK3, PCSK4, PCSK5, PCSK6, PCSK7, PCSK8, and PCSK9), plasmin, and plasminogen activators. Examples of enzymes that recognize sequence on the C terminal side of their cleavage site include Asp-N endopeptidase (which cleaves on the N terminal side of aspartic acid; Keil, 1992) and carboxypeptidases such as carboxypeptidase A (which cleaves C-terminal residues except proline, lysine and arginine).

Examples of proteases are also described in Hook, Proteolytic and cellular mechanisms in prohormone and proprotein processing, RG Landes Company, Austin, Texas, USA (1998); Hooper et al., Biochem. J. 321:265-279 (1997); Werb, Cell 91:439-442 (1997); Wolfsberg et al., J. Cell Biol. 131:275-278 (1995); Murakami and Etlinger, Biochem. Biophys. Res. Comm. 146:1249-1259 (1987); Berg et al., Biochem. J. 307:313-326 (1995); Smyth and Trapani, Immunology Today 16:202-206 (1995); Talanian et al., J. Biol. Chem. 272:9677-9682 (1997); and Thornberry et al., J. Biol. Chem. 272:17907-17911 (1997).

TABLE 4

| Cleavage rules |
|---|
| Substrate Cleavage<br>↓<br>—P4—P3—P2—P1—P1'—P2'—P3'—P4'— |

The following enzymes can cleave when the respective compositions of the cleavage sites are found.

| Enzyme name | P4 | P3 | P2 | P1 | P1' | P2' |
|---|---|---|---|---|---|---|
| Arg-C proteinase | — | — | — | R | — | — |
| Asp-N endopeptidase | — | — | — | — | D | — |
| Clostripain (Clostridiopeptidase B) | — | — | — | R | — | — |
| Enterokinase | D or N | D or N | D or N | K | — | — |
| Factor Xa | A, F, G , I, L, T ,V or M | D or E | G | R | — | — |
| LysC | — | — | — | K | — | — |
| Thrombin | — | — | G | R | G | — |
| | A, F, G, I, L, T, V or M | A, F, G, I, L, T, V, W or A | P | R | not D or E | not DE |
| Trypsin | — | — | — | K or R | not P | — |
| (please note the | — | — | W | K | P | — |
| exceptions) | — | — | M | R | P | — |
| Enzyme name | P4 | P3 | P2 | P1 | P1' | P2' |

The exception rules: The above cleavage rules do not apply, i.e. no cleavage occurs, with the following compositions of the cleavage sites:

| Enzyme name | P4 | P3 | P2 | P1 | P1' | P2' | |
|---|---|---|---|---|---|---|---|
| Trypsin | — | — | C or D | K | D | — | |
| | | — | — | C | K | H or Y | — |
| | | — | — | C | R | K | — |
| | | — | — | R | R | H or R | — |

Some useful forms of activatable CendR elements can be, or can be in, circular proteins or peptides. The CendR element would be latent in such circular structures because the CendR element would not be at a free C-terminal end. Circular proteins and peptides can be formed in a variety of ways known in the art, such as by cysteine bonds, by covalent bonds, by reaction of active groups, and via linkers. Cysteine bonds are a useful way to circularize proteins and peptides. It should be understood that the circularizing linkage need not be at the C-terminal end of the CendR element. By placing the circularizing linkage away from the C-terminal end of the CendR element, the choice of circularizing bond and the choice of the cleavable bond of the latent CendR element each can be independently. For example, the circularizing linkage can be a cysteine bond while the cleavable bond of the latent CendR element can be a peptide bond (where the peptide bond can be, for example, at the cleavage site of a protease target).

The CendR element in a disclosed protein, peptide, amino acid sequence or CendR conjugate generally should be at a free C-terminal end or on the N-terminal side of the cleavage site in an activatable CendR element.

In some forms, the peptide or protein of the CendR conjugate can be internalized into a cell when the selected amino acid sequence (CendR element) is present in the peptide or protein, but not when the selected amino acid is not present in the peptide or protein. This can be used to detect whether a protein or peptide comprises a CendR element, for example. The CendR element can be internalized into a cell without being associated with anything other than its own sequence, for example. The CendR element can be the only functional internalization element in the protein or peptide or the CendR conjugate, or there can be one or more additional functional internalization elements. In some forms, the CendR conjugate can be internalized into a cell when the selected amino acid sequence (CendR element) is present in the CendR conjugate, but not when the selected amino acid is not present in the CendR conjugate.

Similarly, in some forms, the peptide or protein of the CendR conjugate can penetrate tissue when the selected amino acid sequence (CendR element) is present in the peptide or protein, but not when the selected amino acid is not present in the peptide or protein. This can be used to detect whether a protein or peptide comprises a CendR element, for example. The CendR element can penetrate tissue without being associated with anything other than its own sequence, for example. The CendR element can be the only functional tissue penetration element in the protein or peptide or the CendR conjugate, or there can be one or more additional functional tissue penetration elements. In some forms, the CendR conjugate can penetrate tissue when the selected amino acid sequence (CendR element) is present in the CendR conjugate, but not when the selected amino acid is not present in the CendR conjugate.

Similarly, in some forms, the peptide or protein of the CendR conjugate can be internalized into a cell and penetrate tissue when the selected amino acid sequence (CendR element) is present in the peptide or protein, but not when the selected amino acid is not present in the peptide or protein. This can be used to detect whether a protein or peptide comprises a CendR element, for example. The CendR element can be internalized into a cell and penetrate tissue without being associated with anything other than its own sequence, for example. The CendR element can be the only functional internalization and tissue penetration element in the protein or peptide or the CendR conjugate, or there can be one or more additional functional internalization and/or tissue penetration elements. In some forms, the CendR conjugate can be internalized into a cell and penetrate tissue when the selected amino acid sequence (CendR element) is present in the CendR conjugate, but not when the selected amino acid is not present in the CendR conjugate.

"Internalization" refers to passage through a plasma membrane or other biological barrier. "Penetration" refers to passage into and through a cell, tissue, or other biological barrier. Penetration generally involves and includes internalization. The disclosed CendR elements generally promote and allow both internalization (such as internalization into a cell) and penetration (such as tissue penetration). Reference to internalization or to penetration should be understood to refer to both internalization and penetration unless the context indicates otherwise (such as separate or distinct discussion and description of internalization into a cell and tissue penetration separately—the present paragraph is an example of such).

By "internalization into a cell" is meant that that CendR element is capable of penetrating the plasma membrane, thereby being internalized into the cell. This internalization can occur with, for example, 10, 20, 30, 40, 50, 60, 70, 80, 90, or 100% efficiency for a given CendR element and a given cell.

A CendR conjugate can be made, for example, by the method comprising: (a) selecting an amino acid sequence for internalization into a cell and/or tissue penetration, wherein the amino acid sequence comprises a C-terminal arginine or lysine (or another CendR element sequence), (b) causing a cargo composition to be covalently coupled or non-covalently associated with a protein or peptide comprising the selected amino acid sequence, wherein the selected amino acid sequence is at the C-terminal end of the protein or peptide, wherein the CendR conjugate comprises the protein or peptide and the coupled or associated cargo composition.

Also disclosed is a method of delivering a cargo composition into a cell, the method comprising: (a) coupling a CendR element to the cargo composition thus forming a CendR conjugate; and (b) exposing the cell to the CendR conjugate, wherein the CendR conjugate can then enter the cell, thereby delivering the cargo composition into the cell.

Also disclosed is a method of causing a cargo composition to penetrate, the method comprising: (a) coupling a CendR element to the cargo composition thus forming a CendR conjugate; and (b) exposing the tissue to the CendR conjugate, wherein the CendR conjugate can then enter and exit cells in the tissue, thereby causing the cargo composition to penetrate the tissue. Passage, or penetration, through tissue (which can also be referred to as extravasation and tissue penetration) can be a function of both cell internalization and exit functions. The disclosed CendR elements and CendR conjugates are capable of tissue penetration because they are capable of both internalization into and exit from cells.

Further disclosed is a method of delivering a cargo composition into a cell, the method comprising: (a) coupling an activatable CendR element to the cargo composition thus forming a CendR conjugate; and (b) exposing the cell to the CendR conjugate, whereupon a cleaving agent activates the activatable CendR element of the CendR conjugate, wherein the CendR conjugate can then enter the cell, thereby delivering the cargo composition into the cell.

Further disclosed is a method of causing a cargo composition to penetrate, the method comprising: (a) coupling an activatable CendR element to the cargo composition, thus forming a CendR conjugate; and (b) exposing the tissue to the CendR conjugate, whereupon a cleaving agent activates the activatable CendR element of the CendR conjugate, wherein the CendR conjugate can then enter and exit cells in the tissue, thereby causing the cargo composition to penetrate the tissue.

Also disclosed is a method of identifying a cell that can internalize a CendR element, the method comprising: (a) exposing a cell to a CendR element; and (b) determining if the CendR element was internalized. The cell can be in an assay, for example. The CendR element can coupled to a protein or peptide, thereby forming a CendR conjugate.

Also disclosed is a method of identifying a cell that can internalize an activatable CendR element, the method comprising: (a) exposing a cell to an activatable CendR element; (b) determining if the activatable CendR element was internalized. The activatable CendR element can be unblocked before exposure to the cell, but does not need to be. This can be used to test the blocking ability of the activatable element, for example. The activatable CendR element can also be a protease-activatable CendR element, which is activated in the presence of a protease that will cleave the activatable element.

Also disclosed is a method of identifying a cancer cell as a candidate for CendR-based therapy, the method comprising: (a) exposing the cancer cell to a CendR element; and (b)

determining if the CendR element was internalized by the cancer cell, wherein an internalized CendR element identifies the cancer cell as being a candidate for CendR-based therapy. The cell can be in an assay, or can be in a subject, for example. The CendR element can be coupled to a cargo composition, such as, for example, a protein or peptide or nanoparticle, thereby forming a CendR conjugate. As used herein, CendR-based therapy refers to treatment of a subject that involves a CendR element or CendR conjugate.

Also disclosed is a method of identifying a tumor as a candidate for CendR-based therapy, the method comprising: (a) exposing tissue from the tumor to a CendR element; and (b) determining if the CendR element passed through the tissue or was internalized by cells in the tissue, wherein a passed-through or internalized CendR element identifies the tumor as being a candidate for CendR-based therapy.

Also disclosed is a method of producing an activatable CendR element that can be activated in proximity to a cell of interest, the method comprising forming an activatable CendR element wherein a blocking group is coupled to a CendR element via a cleavable bond, wherein the cleavable bond is cleavable by an enzyme present in proximity to the cell of interest. This can further comprise, prior to forming the activatable CendR element, identifying the enzyme that is present in proximity to the cell of interest. This can further comprise, prior to forming the activatable CendR element, selecting the cleavable bond based on the enzyme that is present in proximity to the cell of interest.

Also disclosed is a method of forming an activatable CendR element, the method comprising: (a) selecting an amino acid sequence for internalization into a cell, wherein the amino acid sequence comprises a CendR element, wherein the CendR element (such as a C-terminal arginine, lysine, or lysine-glycine or another CendR element sequence) comprises a terminal carboxyl group, and (b) causing a blocking group to be covalently coupled to the terminal carboxyl group of the selected amino acid sequence, wherein the bond coupling the blocking group and the terminal carboxyl group is cleavable, wherein the activatable CendR element comprises the selected amino acid sequence and the blocking group. This can further comprise, prior to step (b), selecting the bond coupling the blocking group and the terminal carboxyl group to be cleavable by a protease present in proximity to the cell of interest.

Further disclosed is an activatable CendR element made by the method comprising (a) selecting an amino acid sequence for internalization into a cell, wherein the amino acid sequence comprises a CendR element, wherein the CendR element comprises a terminal carboxyl group, and (b) causing a blocking group to be covalently coupled to the terminal carboxyl group of the selected amino acid sequence, wherein the bond coupling the blocking group and the terminal carboxyl group is cleavable, wherein the activatable CendR element comprises the selected amino acid sequence and the blocking group. The method can further comprise, prior to step (b), selecting the bond coupling the blocking group and the terminal carboxyl group to be cleavable by a protease present in proximity to the cell/cell type/cells/tissue of interest.

Disclosed are CendR elements and proteins and peptides comprising CendR elements. Also disclosed are CendR conjugates comprising a cargo composition covalently coupled or non-covalently associated with a protein or peptide comprising a CendR element. Also disclosed are CendR conjugates comprising a cargo composition covalently coupled or non-covalently associated with a protein or peptide comprising a selected amino acid sequence, wherein the amino acid sequence comprises a CendR element. The cargo composition can be coupled or associated with the protein or peptide on the N terminal side of the CendR element.

Also disclosed are activatable CendR elements and proteins and peptides comprising activatable CendR elements. Also disclosed are activatable CendR conjugates comprising a cargo composition covalently coupled or non-covalently associated with a protein or peptide comprising an activatable CendR element. Also disclosed are activatable CendR conjugates comprising a cargo composition covalently coupled or non-covalently associated with a protein or peptide comprising a selected amino acid sequence, wherein the amino acid sequence comprises an activatable CendR element. The cargo composition can be coupled or associated with the protein or peptide on the N terminal side of the activatable CendR element.

Also disclosed are CendR conjugates made by the method comprising causing a cargo composition to be covalently coupled or non-covalently associated with a protein or peptide comprising a CendR element, wherein the cargo composition is coupled or associated with the protein or peptide on the N terminal side of the CendR element. Also disclosed are CendR conjugates made by the method comprising causing a cargo composition to be covalently coupled or non-covalently associated with a protein or peptide comprising a selected amino acid sequence, wherein the amino acid sequence comprises a C-terminal element, wherein the cargo composition is coupled or associated with the protein or peptide on the N terminal side of the CendR element. Also disclosed are CendR conjugates made by the method comprising (a) selecting an amino acid sequence for internalization into a cell and/or tissue penetration, wherein the amino acid sequence comprises a C-terminal element, and (b) causing a cargo composition to be covalently coupled or non-covalently associated with a protein or peptide comprising the selected amino acid sequence, wherein the cargo composition is coupled or associated with the protein or peptide on the N terminal side of the CendR element. The CendR conjugate can comprise the protein or peptide and the coupled or associated cargo composition.

Also disclosed are activatable CendR element made by the method comprising causing a blocking group to be covalently coupled to a CendR element, wherein a bond coupling the blocking group and the CendR element is cleavable. Also disclosed are activatable CendR element made by the method comprising causing a blocking group to be covalently coupled to an amino acid sequence, wherein the amino acid sequence comprises a CendR element, wherein a bond coupling the blocking group and the CendR element is cleavable. Also disclosed are activatable CendR element made by the method comprising (a) selecting an amino acid sequence for internalization into a cell and/or tissue penetration, wherein the amino acid sequence comprises a CendR element, and (b) causing a blocking group to be covalently coupled to the CendR element, wherein a bond coupling the blocking group and the CendR element is cleavable. The blocking group covalently coupled to the CendR element reduces or prevents internalization into a cell and/or tissue penetration. The blocking group covalently coupled to the CendR element can reduce or prevent internalization into a cell and/or tissue penetration compared to the same CendR element with no blocking group. The activatable CendR element can comprise the selected amino acid sequence and the blocking group.

The protein or peptide can be internalized into a cell and/or penetrate tissue when the CendR element is present in the protein or peptide but not when the CendR element is not present in the protein or peptide. The protein or peptide can be internalized into a cell and/or penetrate tissue when the selected amino acid sequence is present in the protein or peptide but not when the selected amino acid is not present in the protein or peptide. The CendR element can be internalized into a cell and/or penetrate tissue without being associated with the cargo composition. The selected amino acid sequence can be internalized into a cell and/or penetrate tissue without being associated with the cargo composition. The CendR element can be the only functional internalization element in the protein or peptide, the CendR element can be the only functional tissue penetration element in the protein or peptide, or both. The selected amino acid sequence can be the only functional internalization element in the protein or peptide, the selected amino acid sequence can be the only functional tissue penetration element in the protein or peptide, or both. The CendR element can be the only functional internalization element in the CendR conjugate, the CendR element can be the only functional tissue penetration element in the CendR conjugate, or both. The selected amino acid sequence can be the only functional internalization element in the CendR conjugate, the selected amino acid sequence can be the only functional tissue penetration element in the CendR conjugate, or both.

The CendR element can be an activatable CendR element. The CendR element can be a protease-activatable CendR element. The protein or peptide can be circular or can contain a loop. The CendR element can be at the C-terminal end of the protein or peptide. The CendR element can comprise a terminal carboxyl group. A blocking group can be coupled to the terminal carboxyl group. The bond coupling the blocking group and the terminal carboxyl group can be selected to be cleavable by a protease present in proximity to the cell of interest. The blocking group can be coupled to the C-terminal amino acid of the CendR element. The blocking group can be coupled to an amino acid of the CendR element other than the C-terminal amino acid of the CendR element.

A cargo composition can be covalently coupled or non-covalently associated with a protein or peptide comprising a selected amino acid sequence, wherein the amino acid sequence can comprise a CendR element. The cargo composition can be coupled or associated with the protein or peptide on the N terminal side of the CendR element. The cargo composition can be, for example, a nanoparticle, or a molecule, or complex of molecules with therapeutic or diagnostic applications. Therapeutic cargo compositions that can be targeted with CendR elements include but are not limited to a nanoparticle, a molecule, a complex of molecules, an anti-angiogenic agent, a pro-angiogenic agent, a cancer chemotherapeutic agent, a cytotoxic agent, a pro-cell survival agent, a cell differentiating agent, a neuroprotective agent, an immunomodulatory agent, an anti-inflammatory agent, an anti-arthritic agent, an anti-viral agent, or a combination of these. Diagnostic cargo compositions that can be targeted with CendR elements include but are not limited to a nanoparticle, a molecule, a complex of molecules, a MRI imaging agent, a radioimaging agent, an optical imaging agent, a molecular tag (such as biotin), a fluorophore, an epitope tag (that can, for example, be detected using a specific molecular assay), or a combination of these.

Also disclosed are methods of forming a CendR conjugate, the method comprising causing a cargo composition to be covalently coupled or non-covalently associated with a protein or peptide comprising a CendR element, wherein the cargo composition is coupled or associated with the protein or peptide on the N terminal side of the CendR element. Also disclosed are methods of forming a CendR conjugate, the method comprising causing a cargo composition to be covalently coupled or non-covalently associated with a protein or peptide comprising a selected amino acid sequence, wherein the amino acid sequence comprises a CendR element, wherein the cargo composition is coupled or associated with the protein or peptide on the N terminal side of the CendR element. Also disclosed are methods of forming a CendR conjugate, the method comprising (a) selecting an amino acid sequence for internalization into a cell and/or tissue penetration, wherein the amino acid sequence comprises a CendR element, and (b) causing a cargo composition to be covalently coupled or non-covalently associated with a protein or peptide comprising the selected amino acid sequence, wherein the cargo composition is coupled or associated with the protein or peptide on the N terminal side of the CendR element. The CendR conjugate can comprise the protein or peptide and the coupled or associated cargo composition.

Also disclosed are methods of delivering a cargo composition into a cell, the method comprising exposing the cell to a CendR conjugate, wherein the CendR element comprises a cargo composition covalently coupled or non-covalently associated with a CendR element, wherein the CendR conjugate can then enter the cell, thereby delivering the cargo composition into the cell. Also disclosed are methods of delivering a cargo composition into a cell, the method comprising exposing the cell to a CendR conjugate, wherein the CendR element comprises a cargo composition covalently coupled or non-covalently associated with a protein or peptide comprising a CendR element, wherein the CendR conjugate can then enter the cell, thereby delivering the cargo composition into the cell. Also disclosed are methods of delivering a cargo composition into a cell, the method comprising (a) coupling a CendR element to the cargo composition thus forming a CendR conjugate; and (b) exposing the cell to the CendR conjugate, wherein the CendR conjugate can then enter the cell, thereby delivering the cargo composition into the cell.

Also disclosed are methods of identifying a cell that can internalize a CendR element, the method comprising (a) exposing a cell to a CendR element, and (b) determining if the CendR element was internalized. Also disclosed are methods of identifying a cancer cell as a candidate for CendR-based therapy, the method comprising (a) exposing the cancer cell to a CendR element, and (b) determining if the CendR element was internalized by the cancer cell, wherein an internalized CendR element identifies the cancer cell as being a candidate for CendR-based therapy. The cell can be in an assay. The CendR element can be coupled to a protein or peptide. The CendR element can be an activatable CendR element. The activatable CendR element can be activated before exposure to the cell. The activatable CendR element can be a protease-activatable CendR element. The protein or peptide can be circular. The CendR element can be at the C-terminal end of the protein or peptide.

Also disclosed are methods of identifying a tissue that can be penetrated by a CendR element, the method comprising (a) exposing a tissue to a CendR element, and (b) determining if the CendR element penetrated the tissue. Iso disclosed are methods of identifying a tumor as a candidate for CendR-based therapy, the method comprising (a) exposing a cell from the tumor to a CendR element, and (b) determining if the CendR element was internalized by the cell, wherein an internalized CendR element identifies the tumor as being a candidate for CendR-based therapy. Also disclosed are methods of identifying a tumor as a candidate for CendR-based therapy, the method comprising (a) exposing the tumor to a CendR element, and (b) determining if the CendR element penetrated the tumor, wherein a CendR element that penetrated identifies the tumor as being a candidate for CendR-based therapy. The tumor can be in an assay. The CendR element can be coupled to a protein or peptide. The CendR element can be an activatable CendR element. The activatable CendR element can be activated before exposure to the tumor. The activatable CendR element can be a protease-activatable CendR element. The protein or peptide can be circular. The CendR element can be at the C-terminal end of the protein or peptide.

Also disclosed are methods of producing an activatable CendR element that can be activated in proximity to a cell of interest, the method comprising forming an activatable CendR element wherein a blocking group is coupled to a CendR element via a cleavable bond, wherein the cleavable bond is cleavable by an enzyme present in proximity to the cell of interest. The cell can be in a subject. The enzyme that is present in proximity to the cell of interest can be identified. The enzyme that is present in proximity to the cell of interest can be identified prior to forming the activatable CendR element. The cleavable bond can be selected based on the enzyme that is present in proximity to the cell of interest. The cleavable bond can be selected prior to forming the activatable CendR element. The CendR element can comprise a terminal carboxyl group, wherein the blocking group is coupled to the terminal carboxyl group.

Also disclosed are methods of forming an activatable CendR element, the method comprising causing a blocking group to be covalently coupled to a CendR element, wherein a bond coupling the blocking group and the CendR element is cleavable. Also disclosed are methods of forming an activatable CendR element, the method comprising causing a blocking group to be covalently coupled to an amino acid sequence, wherein the amino acid sequence comprises a CendR element the CendR element, wherein a bond coupling the blocking group and the CendR element is cleavable. Also disclosed are methods of forming an activatable CendR element, the method comprising (a) selecting an amino acid sequence for internalization into a cell and/or tissue penetration, wherein the amino acid sequence comprises a CendR element, and (b) causing a blocking group to be covalently coupled to the CendR element, wherein a bond coupling the blocking group and the CendR element is cleavable. The blocking group covalently coupled to the CendR element reduces or prevents internalization into a cell and/or tissue penetration. The blocking group covalently coupled to the CendR element can reduce or prevent internalization into a cell and/or tissue penetration compared to the same CendR element with no blocking group. The activatable CendR element can comprise the selected amino acid sequence and the blocking group. The cell can be in a subject. The enzyme that is present in proximity to the cell of interest can be identified. The enzyme that is present in proximity to the cell of interest can be identified prior to forming the activatable CendR element. The cleavable bond can be selected based on the enzyme that is present in proximity to the cell of interest. The cleavable bond can be selected prior to forming the activatable CendR element. The CendR element can comprise a terminal carboxyl group, wherein the blocking group is coupled to the terminal carboxyl group. A cargo composition can be covalently coupled or non-covalently associated with a protein or peptide comprising the selected amino acid sequence. The cargo composition can be coupled or associated with the protein or peptide on the N terminal side of the CendR element.

The CendR element can have a length of up to 10, 20, 30, 40, 50, 100, 150, 200, 250, 300, 400, 500, 1000 or 2000 residues. In particular embodiments, a CendR element can have a length of at least 1, 2, 3, 4, 5, 6, 7, 8, 9, 10, 15, 20, 25, 30, 40, 50, 60, 70, 80, 90, 100 or 200 residues. In further embodiments, a CendR element can have a length of 2 to 200 residues, 2 to 100 residues, 2 to 90 residues, 2 to 80 residues, 2 to 70 residues, 2 to 60 residues, 2 to 50 residues, 2 to 40 residues, 2 to 30 residues, 2 to 20 residues, 2 to 15 residues, 2 to 10 residues, 3 to 200 residues, 3 to 100 residues, 3 to 90 residues, 3 to 80 residues, 3 to 70 residues, 3 to 60 residues, 3 to 50 residues, 3 to 40 residues, 3 to 30 residues, 3 to 20 residues, 3 to 15 residues, 3 to 10 residues, 4 to 200 residues, 4 to 100 residues, 4 to 90 residues, 4 to 80 residues, 4 to 70 residues, 4 to 60 residues, 4 to 50 residues, 4 to 40 residues, 4 to 30 residues, 4 to 20 residues, 4 to 15 residues, 4 to 10 residues, 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues. As used herein, the term "residue" refers to an amino acid or amino acid analog.

The protein or peptide portion of a CendR conjugate can have a length of up to 50, 100, 150, 200, 250, 300, 400, 500, 1000 or 2000 residues. In particular embodiments, the protein or peptide portion of a CendR conjugate can have a length of at least 10, 20, 30, 40, 50, 60, 70, 80, 90, 100 or 200 residues. In further embodiments, the protein or peptide portion of a CendR conjugate can have a length of 2 to 200 residues, 2 to 100 residues, 2 to 90 residues, 2 to 80 residues, 2 to 70 residues, 2 to 60 residues, 2 to 50 residues, 2 to 40 residues, 2 to 30 residues, 2 to 20 residues, 2 to 15 residues, 2 to 10 residues, 3 to 200 residues, 3 to 100 residues, 3 to 90 residues, 3 to 80 residues, 3 to 70 residues, 3 to 60 residues, 3 to 50 residues, 3 to 40 residues, 3 to 30 residues, 3 to 20 residues, 3 to 15 residues, 3 to 10 residues, 4 to 200 residues, 4 to 100 residues, 4 to 90 residues, 4 to 80 residues, 4 to 70 residues, 4 to 60 residues, 4 to 50 residues, 4 to 40 residues, 4 to 30 residues, 4 to 20 residues, 4 to 15 residues, 4 to 10 residues, 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

The CendR conjugate can have a length of up to 50, 100, 150, 200, 250, 300, 400, 500, 1000 or 2000 residues. In particular embodiments, a CendR conjugate can have a length of at least 10, 20, 30, 40, 50, 60, 70, 80, 90, 100 or 200 residues. In further embodiments, a CendR conjugate can have a length of 5 to 200 residues, 5 to 100 residues, 5 to 90 residues, 5 to 80 residues, 5 to 70 residues, 5 to 60 residues, 5 to 50 residues, 5 to 40 residues, 5 to 30 residues, 5 to 20 residues, 5 to 15 residues, 5 to 10 residues, 10 to 200 residues, 10 to 100 residues, 10 to 90 residues, 10 to 80 residues, 10 to 70 residues, 10 to 60 residues, 10 to 50 residues, 10 to 40 residues, 10 to 30 residues, 10 to 20 residues, 20 to 200 residues, 20 to 100 residues, 20 to 90 residues, 20 to 80 residues, 20 to 70 residues, 20 to 60 residues, 20 to 50 residues, 20 to 40 residues or 20 to 30 residues.

It is understood that there are numerous amino acid and peptide analogs which can be incorporated into the disclosed CendR conjugates. For example, there are numerous D amino acids or amino acids which can be used. The opposite stereoisomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH═CH— (cis and trans), —$COCH_2$—, —CH(OH)$CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—CH $H_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH)$CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Disclosed are polyfunctional CendR conjugates which, in addition to the CendR element, contain, for example, a homing peptide fused to a second peptide having a separate function. Such polyfunctional conjugates have at least two functions conferred by different portions of the full-length molecule and can, for example, display anti-angiogenic activity or pro-apoptotic activity in addition to selective homing activity.

As used herein, the term "peptide" is used broadly to mean peptides, proteins, fragments of proteins and the like. The term "peptidomimetic," as used herein, means a peptide-like molecule that has the activity of the peptide upon which it is structurally based. Such peptidomimetics include chemically modified peptides, peptide-like molecules containing non-naturally occurring amino acids, and peptoids and have an activity such as that from which the peptidomimetic is derived (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861).

As disclosed herein, the term "cargo composition" refers to any composition of matter that can be used in conjunction with the CendR element. For example, a cargo composition can be a molecule, a conjugate, an association of molecules, a composition, a mixture. One of skill in the art can determine what cargo can be coupled to a CendR conjugate. The CendR conjugates disclosed herein can comprise the CendR element coupled to or associated with the cargo composition. Examples of cargo compositions include, but are not limited to, an anti-angiogenic agents, pro-angiogenic agents, cancer chemotherapeutic agents, cytotoxic agents, anti-inflammatory agents, anti-arthritic agents, polypeptides, nucleic acid molecules, small molecules, nanoparticles, microparticles, fluorophores, fluorescein, rhodamine, a radionuclide, indium-111, technetium-99, carbon-11, carbon-13, or a combination thereof. These cargo compositions associated with a CendR element in a CendR conjugates can be moieties. As used herein, the term "moiety" is used broadly to mean a physical, chemical, or biological material that generally imparts a biologically useful function to a linked cargo composition. A moiety can be any natural or nonnatural material including, without limitation, a biological material, such as a cell, phage or other virus; an organic chemical such as a small molecule; a nanoparticle, a radionuclide; a nucleic acid molecule or oligonucleotide; a polypeptide; or a peptide. For example, moieties that affect the target, such as moieties with therapeutic effect, or that facilitate detection, visualization or imaging of the target, such as fluorescent molecule or radionuclides.

Components of the disclosed CendR conjugates can be combined, linked and/or coupled in any suitable manner. For example, moieties and homing molecules can be associated covalently or non-covalently, directly or indirectly, with or without a linker moiety.

In some embodiments, a CendR conjugate can comprise a cancer chemotherapeutic agent. For example, the cargo composition of a CendR conjugate can be a cancer chemotherapeutic agent. As used herein, a "cancer chemotherapeutic agent" is a chemical agent that inhibits the proliferation, growth, life-span or metastatic activity of cancer cells. Such a cancer chemotherapeutic agent can be, without limitation, a taxane such as docetaxel; an anthracyclin such as doxorubicin; an alkylating agent; a vinca alkaloid; an anti-metabolite; a platinum agent such as cisplatin or carboplatin; a steroid such as methotrexate; an antibiotic such as adriamycin; a isofamide; or a selective estrogen receptor modulator; an antibody such as trastuzumab.

A CendR conjugate can comprise a therapeutic agent. For example, cargo composition of the CendR conjugate can be a therapeutic agent. Useful therapeutic agents can be, for example, a cytotoxic agent, which, as used herein, can be any molecule that directly or indirectly promotes cell death. Useful cytotoxic agents include, without limitation, small molecules, polypeptides, peptides, peptidomimetics, nucleic acid-molecules, cells and viruses. As non-limiting examples, useful cytotoxic agents include cytotoxic small molecules such as doxorubicin, docetaxel or trastuzumab; antimicrobial peptides such as those described further below; pro-apoptotic polypeptides such as caspases and toxins, for example, caspase-8; diphtheria toxin A chain, *Pseudomonas* exotoxin A, cholera toxin, ligand fusion toxins such as DAB389EGF, *Ricinus communis* toxin (ricin); and cytotoxic cells such as cytotoxic T cells. See, for example, Martin et al., Cancer Res. 60:3218-3224 (2000); Kreitman and Pastan, Blood 90:252-259 (1997); Allam et al., Cancer Res. 57:2615-2618 (1997); and Osborne and Coronado-Heinsohn, Cancer J. Sci. Am. 2:175 (1996). One skilled in the art understands that these and additional cytotoxic agents described herein or known in the art can be useful in the disclosed conjugates and methods.

In some forms, a therapeutic agent can be a therapeutic polypeptide. As used herein, a therapeutic polypeptide can be any polypeptide with a biologically useful function. Useful therapeutic polypeptides encompass, without limitation, cytokines, antibodies, cytotoxic polypeptides; pro-apoptotic polypeptides; and anti-angiogenic polypeptides. As non-limiting examples, useful therapeutic polypeptides can be a cytokine such as tumor necrosis factor-α (TNF-α), tumor necrosis factor-β (TNF-β), granulocyte macrophage colony stimulating factor (GM-CSF), granulocyte colony stimulating factor (G-CSF), interferon-α. (IFN-α); interferon. gamma. (IFN-γ), interleukin-1 (IL-1), interleukin-2 (IL-2), interleukin-3 (IL-3), interleukin-4 (IL-4), interleukin-6 (IL-6), interleukin-7 (IL-7), interleukin-10 (IL-10), interleukin-12 (IL-12), lymphotactin (LTN) or dendritic cell chemokine 1 (DC-CK1); an anti-HER2 antibody or fragment thereof; a cytotoxic polypeptide including a toxin or caspase, for example, diphtheria toxin A chain, *Pseudomonas* exotoxin A, cholera toxin, a ligand fusion toxin such as DAB389EGF or ricin; or an anti-angiogenic polypeptide such as angiostatin, endostatin, thrombospondin, platelet factor 4; anastellin; or one of those described further herein or known in the art. It is understood that these and other polypeptides with biological activity can be a "therapeutic polypeptide."

A therapeutic agent useful in the disclosed CendR conjugates can be an anti-angiogenic agent. As used herein, the term "anti-angiogenic agent" means a molecule that reduces or prevents angiogenesis, which is the growth and development of blood vessels. The conjugates can be used to treat or diagnose any disease, condition, or disorder associated with angiogenesis. For example, macular degeneration and diabetic vascular complications can be diagnosed and/or treated. A variety of anti-angiogenic agents can be prepared by routine methods. Such anti-angiogenic agents include, without limitation, small molecules; proteins such as dominant negative forms of angiogenic factors, transcription factors and antibodies; peptides; and nucleic acid molecules including ribozymes, antisense oligonucleotides, and nucleic acid molecules encoding, for example, dominant negative forms of angiogenic factors and receptors, transcription factors, and antibodies and antigen-binding fragments thereof. See, for example, Hagedorn and Bikfalvi, Crit. Rev. Oncol. Hematol. 34:89-110 (2000), and Kirsch et al., J. Neurooncol. 50:149-163 (2000).

Some other examples of useful therapeutic agents include nitrogen mustards, nitrosorueas, ethyleneimine, alkane sulfonates, tetrazine, platinum compounds, pyrimidine analogs, purine analogs, antimetabolites, folate analogs, anthracyclines, taxanes, vinca alkaloids, topoisomerase inhibitors and hormonal agents. Exemplary chemotherapy drugs are Actinomycin-D, Alkeran, Ara-C, Anastrozole, Asparaginase, BiCNU, Bicalutamide, Bleomycin, Busulfan, Capecitabine, Carboplatin, Carboplatinum, Carmustine, CCNU, Chlorambucil, Chlomaphazine, Cholophosphamide, Cisplatin, Cladribine, CPT-11, Cyclophosphamide, Cytarabine, Cytosine arabinoside, Cytoxan, Dacarbazine, Dactinomycin, Daunorubicin, Dexrazoxane, Docetaxel, Doxorubicin, DTIC, Epirubicin, Estramustine, Ethyleneimine, Etoposide, Floxuridine, Fludarabine, Fluorouracil, Flutamide, Fotemustine, Gemcitabine, Herceptin, Hexamethylamine, Hydroxyurea, Idarubicin, Ifosfamide, Irinotecan, Lomustine, Mechlorethamine, mechlorethamine oxide hydrochloride, Melphalan, Mercaptopurine, Methotrexate, Mitomycin, Mitotane, Mitoxantrone, Novembiehin, Oxaliplatin, Paclitaxel, Pamidronate, Pentostatin, Phenesterine, Plicamycin, Prednimustine, Procarbazine, Rituximab, Steroids, Streptozocin, STI-571, Streptozocin, Tamoxifen, Temozolomide, Teniposide, Tetrazine, Thioguanine, Thiotepa, Tomudex, Topotecan, Treosulphan, Trimetrexate, Trofosfamide, Vinblastine, Vincristine, Vindesine, Vinorelbine, VP-16, and Xeloda. Alkylating agents such as Thiotepa and; alkyl sulfonates such as Busulfan, Improsulfan and Piposulfan; aziridines such as Benzodopa, Carboquone, Meturedopa, and Uredopa; ethylenimines and methylamelamines including altretamine, triethylenemelamine, trietylenephosphoramide, triethylenethiophosphaoramide and trimethylolomelamine; nitroureas such as Cannustine, Chlorozotocin, Fotemustine, Lomustine, Nimustine, and Ranimustine; antibiotics such as Aclacinomysins, Actinomycin, Authramycin, Azaserine, Bleomycins, Cactinomycin, Calicheamicin, Carabicin, Caminomycin, Carzinophilin, Chromoinycins, Dactinomycin, Daunorubicin, Detorubicin, 6-diazo-5-oxo-L-norleucine, Doxorubicin, Epirubicin, Esorubicin, Idambicin, Marcellomycin, Mitomycins, mycophenolic acid, Nogalamycin, Olivomycins, Peplomycin, Potfiromycin, Puromycin, Quelamycin, Rodorubicin, Streptonigrin, Streptozocin, Tubercidin, Ubenimex, Zinostatin, and Zorubicin; anti-metabolites such as Methotrexate and 5-fluorouracil (5-FU); folic acid analogues such as Denopterin, Methotrexate, Pteropterin, and Trimetrexate; purine analogs such as Fludarabine, 6-mercaptopurine, Thiamiprine, and Thioguanine; pyrimidine analogs such as Ancitabine, Azacitidine, 6-azauridine, Carmofur, Cytarabine, Dideoxyuridine, Doxifluridine, Enocitabine, Floxuridine, and 5-FU; androgens such as Calusterone, Dromostanolone Propionate, Epitiostanol, Rnepitiostane, and Testolactone; anti-adrenals such as aminoglutethimide, Mitotane, and Trilostane; folic acid replenisher such as frolinic acid; aceglatone; aldophosphamide glycoside; aminolevulinic acid; Amsacrine; Bestrabucil; Bisantrene; Edatraxate; Defofamine; Demecolcine; Diaziquone; Elfornithine; elliptinium acetate; Etoglucid; gallium nitrate; hydroxyurea; Lentinan; Lonidamine; Mitoguazone; Mitoxantrone; Mopidamol; Nitracrine; Pentostatin; Phenamet; Pirarubicin; podophyllinic acid; 2-ethylhydrazide; Procarbazine; PSK®; Razoxane; Sizofrran; Spirogermanium; tenuazonic acid; triaziquone; 2,2',2"-trichlorotriethylamine; Urethan; Vindesine; Dacarbazine; Mannomustine; Mitobronitol; Mitolactol; Pipobroman;

Gacytosine; Arabinoside ("Ara-C"); cyclophosphamide; thiotEPa; taxoids, e.g., Paclitaxel (TAXOL®, Bristol-Myers Squibb Oncology, Princeton, N.J.) and Doxetaxel (TAXOTERE®, Rhone-Poulenc Rorer, Antony, France); Gemcitabine; 6-thioguanine; Mercaptopurine; Methotrexate; platinum analogs such as Cisplatin and Carboplatin; Vinblastine; platinum; etoposide (VP-16); Ifosfamide; Mitomycin C; Mitoxantrone; Vincristine; Vinorelbine; Navelbine; Novantrone; Teniposide; Daunomycin; Aminopterin; Xeloda; Ibandronate; CPT-11; topoisomerase inhibitor RFS 2000; difluoromethylornithine (DMFO); retinoic acid; Esperamicins; Capecitabine; and pharmaceutically acceptable salts, acids or derivatives of any of the above. Also included are anti-hormonal agents that act to regulate or inhibit hormone action on tumors such as anti-estrogens including for example Tamoxifen, Raloxifene, aromatase inhibiting 4(5)-imidazoles, 4 Hydroxytamoxifen, Trioxifene, Keoxifene, Onapristone, And Toremifene (Fareston); and anti-androgens such as Flutamide, Nilutamide, Bicalutamide, Leuprolide, and Goserelin; and pharmaceutically acceptable salts, acids or derivatives of any of the above.

The CendR conjugate can also comprise a detectable agent. Such a detectable agent can be the cargo composition of the CendR conjugate, can comprise a portion of the cargo composition of the CendR conjugate, or can be a separate component of the CendR conjugate from the molecule or moiety. A variety of detectable agents are useful in the disclosed methods. As used herein, the term "detectable agent" refers to any molecule which can be detected. Useful detectable agents include moieties that can be administered in vivo and subsequently detected. Detectable agents useful in the disclosed conjugates and imaging methods include yet are not limited to radiolabels and fluorescent molecules. The detectable agent can be, for example, any moiety that facilitates detection, either directly or indirectly, preferably by a non-invasive and/or in vivo visualization technique. For example, a detectable agent can be detectable by any known imaging techniques, including, for example, a radiological technique. Detectable agents can include, for example, a contrasting agent, e.g., where the contrasting agent is ionic or non-ionic. In some embodiments, for instance, the detectable agent comprises a tantalum compound and/or a barium compound, e.g., barium sulfate. In some embodiments, the detectable agent comprises iodine, such as radioactive iodine. In some embodiments, for instance, the detectable agent comprises an organic iodo acid, such as iodo carboxylic acid, triiodophenol, iodoform, and/or tetraiodoethylene. In some embodiments, the detectable agent comprises a non-radioactive detectable agent, e.g., a non-radioactive isotope. For example, Gd can be used as a non-radioactive detectable agent in certain embodiments. Detectable agents can also include radioactive isotopes, enzymes, fluorophores, and quantum dots (Qdot®). For example, the detection moiety can be an enzyme, biotin, metal, or epitope tag. Other known or newly discovered detectable markers are contemplated for use with the provided conjugates.

The disclosed CendR conjugates can be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. The materials can be in solution, suspension (for example, incorporated into microparticles, liposomes, or cells).

The CendR conjugates can be used therapeutically in combination with a pharmaceutically acceptable carrier. Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

A pharmaceutical preparation can include, as an active ingredient, a composition comprising at least one epitope of a target protein or polypeptide, the at least one epitope being capable of eliciting antibodies capable of binding to the stem region of hemagglutinin. Alternatively, a pharmaceutical composition can include, as an active ingredient, a composition comprising at least an immunological portion of an antibody being for binding at least one epitope of the stem region of hemagglutinin.

The preparation can be administered to a subject or organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to a subject or organism.

Herein the term "active ingredient" refers to the preparation accountable for the biological effect.

As used herein, the phrases "physiologically acceptable carrier" and "pharmaceutically acceptable carrier" which can be interchangeably used refer to a carrier or a diluent that does not cause significant irritation to a subject or organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in Remington's Pharmaceutical Sciences, Mack Publishing Co., Easton, Pa., latest edition, which is incorporated herein by reference.

Suitable routes of administration can, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections. Alternately, one can administer a preparation in a local rather than systemic manner.

Pharmaceutical compositions can be manufactured by processes well known in the art, e.g., by means of conventional mixing, dissolving, granulating, dragee-making, levigating, emulsifying, encapsulating, entrapping or lyophilizing processes.

Pharmaceutical compositions for use in the disclosed methods thus can be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients can be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents can be added, such as cross-linked polyvinyl pyrrolidone, agar, or alginic acid or a salt thereof such as sodium alginate.

Dragee cores are provided with suitable coatings. For this purpose, concentrated sugar solutions can be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments can be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules can contain the active ingredients in admixture with filler such as lactose, binders such as starches, lubricants such as talc or magnesium stearate and, optionally, stabilizers. In soft capsules, the active ingredients can be dissolved or suspended in suitable liquids, such as fatty oils, liquid paraffin, or liquid polyethylene glycols. In addition, stabilizers can be added. All formulations for oral administration should be in dosages suitable for the chosen route of administration.

For buccal administration, the compositions can take the form of tablets or lozenges formulated in conventional manner.

For administration by nasal inhalation, the active ingredients for use in the disclosed methods can be conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit can be determined by providing a valve to deliver a metered amount. Capsules and cartridges of, e.g., gelatin for use in a dispenser can be formulated containing a powder mix of the compound and a suitable powder base such as lactose or starch.

The preparations described herein can be formulated for parenteral administration, e.g., by bolus injection or continuous infusion. Formulations for injection can be presented in unit dosage form, e.g., in ampoules or in multidose containers with optionally, an added preservative. The compositions can be suspensions, solutions or emulsions in oily or aqueous vehicles, and can contain formulatory agents such as suspending, stabilizing and/or dispersing agents.

Pharmaceutical compositions for parenteral administration include aqueous solutions of the active preparation in water-soluble form. Additionally, suspensions of the active ingredients can be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions can contain substances, which increase the viscosity of the suspension, such as sodium carboxymethyl cellulose, sorbitol or dextran. Optionally, the suspension can also contain suitable stabilizers or agents which increase the solubility of the active ingredients to allow for the preparation of highly concentrated solutions.

Alternatively, the active ingredient can be in powder form for constitution with a suitable vehicle, e.g., sterile, pyrogen-free water based solution, before use.

The preparations can also be formulated in rectal compositions such as suppositories or retention enemas, using, e.g., conventional suppository bases such as cocoa butter or other glycerides.

Pharmaceutical compositions for use in the disclosed methods include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any preparation used in the disclosed methods, the therapeutically effective amount or dose can be estimated initially from in vitro and cell culture assays. For example, a dose can be formulated in animal models to achieve a desired circulating antibody concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl et al in The Pharmacological Basis of Therapeutics, Ch. 1 p. 1. (1975)).

Dosage amount and interval can be adjusted individually to provide plasma of antibodies which are sufficient to prevent or reduce viral entry (minimal effective concentration, MEC). The MEC will vary for each preparation, but can be estimated from in vitro data. Dosages necessary to achieve the MEC will depend on individual characteristics and route of administration. Binding assays can be used to determine plasma concentrations.

Dosage intervals can also be determined using the MEC value. Preparations should be administered using a regimen, which maintains plasma levels above the MEC for 10-90% of the time, preferable between 30-90% and most preferably 50-90%.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Fatty acids (i.e., lipids) that can be conjugated to the disclosed conjugates include those that allow the efficient incorporation of the peptide into liposomes. Generally, the fatty acid is a polar lipid. Thus, the fatty acid can be a phospholipid. The provided conjugates can comprise either natural or synthetic phospholipid. The phospholipids can be selected from phospholipids containing saturated or unsaturated mono or disubstituted fatty acids and combinations thereof. These phospholipids can be, for example, dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Alabaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided conjugates can comprise palmitoyl 16:0.

The cargo composition can be a microparticle or a nanoparticle, such as a nanosphere, nanoshell, nanoworm, heat generating nanoshell, and the like. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Nanoshells can be formed with, for example, a core of a dielectric or inert material such as silicon, coated with a material such as a highly conductive metal which can be excited using radiation such as near infrared light (approximately 800 to 1300 nm). Upon excitation, the nanoshells emit heat. The resulting hyperthermia can kill the surrounding cell(s) or tissue. The combined diameter of the shell and core of the nanoshells ranges from the tens to the hundreds of nanometers. Near infrared light is advantageous for its ability to penetrate tissue. Other types of radiation can also be used, depending on the selection of the nanoparticle coating and targeted cells. Examples include x-rays, magnetic fields, electric fields, and ultrasound. The particles can also be used to enhance imaging, especially using infrared diffuse photon imaging methods. Targeting molecules can be antibodies or fragments thereof, ligands for specific receptors, or other proteins specifically binding to the surface of the cells to be targeted.

The cargo composition can be covalently linked to or non-covalently associated with, for example, the disclosed protein, peptide, amino acid sequence, or CendR element. The cargo composition can be linked, for example, to the amino terminal end of the disclosed protein, peptide, amino acid sequence, or CendR element; to an internal amino acid of the disclosed protein, peptide, amino acid sequence, or CendR element; to the carboxy terminal end of the disclosed protein, peptide, amino acid sequence, or CendR element; to the protein, peptide, amino acid sequence on the N terminal side of the CendR element; via a linker to the disclosed protein, peptide, amino acid sequence, or CendR element; or a combination. The disclosed CendR conjugates can further comprise a linker connecting the cargo composition and disclosed protein, peptide, amino acid sequence, or CendR element. The disclosed protein, peptide, amino acid sequence, or CendR element can also be conjugated to a coating molecule such as bovine serum albumin (BSA) (see Tkachenko et al., (2003) J Am Chem Soc, 125, 4700-4701) that can be used to coat nanoparticles, nanoworms, nanoshells, and the like with the protein, peptide, amino acid sequence, or CendR element.

Protein crosslinkers that can be used to crosslink the cargo composition to the disclosed peptide are known in the art and are defined based on utility and structure and include DSS (Disuccinimidylsuberate), DSP (Dithiobis(succinimidylpropionate)), DTSSP (3,3'-Dithiobis(sulfosuccinimidylpropionate)), SULFO BSOCOES (Bis [2-(sulfosuccinimdooxycarbonyloxy)ethyl]sulfone), BSOCOES (Bis [2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis(sulfosuccinimidylsuccinate)), DPDPB (1,2-Di [3'-(2'-pyridyldithio) propionamido]butane), BSSS (Bis(sulfosuccinimdyl)suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy (6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy) sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

Disclosed are homing molecules coupled to a CendR element in order to selectively deliver the CendR element to a given cell, thereby forming a homing CendR conjugate. A variety of homing molecules can be used in the disclosed compositions, conjugates and methods. Such homing molecules include, without limitation, peptides as disclosed herein. The disclosed compounds, compositions, conjugates and methods can include or use the disclosed homing molecules in various forms, including peptides and peptidomimetics as disclosed. For convenience of expression, in many places herein the use or inclusion of peptides will be recited. It is understood that, in such cases, it is considered that homing molecules in various forms can also be used or included in the same or similar ways as is described in terms of peptides, and such use and inclusion is specifically contemplated and disclosed thereby.

The term "homing molecule" as used herein, means any molecule that selectively homes in vivo to tumors or other specific tissue in preference to normal tissue. Similarly, the term "homing peptide" or "homing peptidomimetic" means a peptide that selectively homes in vivo to regenerating tissue, wounds, or tumors in preference to normal tissue. It is understood that a homing molecule that selectively homes in vivo to regenerating tissue, wounds, or tumors or can exhibit preferential homing to regenerating tissue, wounds, or tumors.

By "selectively homes" is meant that, in vivo, the homing molecule binds preferentially to the target as compared to non-target. For example, the homing molecule can bind preferentially to tumors, as compared to non-tumors. Selective homing to, for example, tumor cells generally is characterized by at least a two-fold greater localization within tumor cells, as compared to several tissue types of non-tumor cells. A homing molecule can be characterized by 5-fold, 10-fold, 20-fold or more preferential localization to cancerous cells, as compared to-most or all non-cancerous cells. Thus, it is understood that, in some cases, a homing molecule homes, in part, to one or more normal organs in addition to homing to tumors. Selective homing can also be referred to as targeting.

Binding in the context of a homing molecule recognizing and/or binding to its target can refer to both covalent and non-covalent binding, for example where a homing molecule can bind, attach or otherwise couple to its target by covalent and/or non-covalent binding. Binding can be either high affinity or low affinity, preferably high affinity. Examples of binding forces that can be useful include, but are not limited to, covalent bonds, dipole interactions, electrostatic forces, hydrogen bonds, hydrophobic interactions, ionic bonds, and/or van der Waals forces. This binding can occur in addition to that binding which occurs with the CendR element.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, "subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject may to an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. In the context of endometriosis and endometriosis cells, it is understood that a subject is a subject that has or can have endometriosis and/or endometriosis cells.

EXAMPLES

The following example is put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Example 1: Delivery of Nanoparticles, Drugs, and Other Substances into and Out of Cells Phage display has been used to isolate a number of highly selective peptides for vascular targeting in vivo. Delivery of macromolecules and colloidal nanoparticles to cells is generally achieved by receptor targeting and/or using cell penetrating peptides.

1. Results

A panel of T7 bacteriophage-displayed peptide libraries was used to identify sequence motifs that lead to cellular uptake of the phage particles by PPC1 prostate carcinoma cells. T7 phage particles are composed of icosahedral nucleocapsid and tail fibers; displayed peptides are expressed as C-terminal fusions to major coat protein GP10, typically at density of 200-415 peptides/phage (FIG. 1A). Conventional T7 peptide libraries (random cyclic CX7C, and linear X7; X is a random residue) were used for the screening. New libraries were also designed to include an RXXR motif, which had been seen in other molecules, such as the iRGD peptide (RXXRXXX and RXXR(A/P)PRXXX (SEQ ID NO: 20) libraries). After 3 rounds of display, selected libraries bound to cell suspensions 500-2,500 fold over phage displaying a 7-glycine (G7) control peptide (FIG. 1B). Sequencing of random phage clones after three rounds of selection demonstrated that, independent of initial library configuration, all libraries converged to display C-terminal arginine residue (FIG. 1C). Phage displaying C-terminal arginine were detectable in cells after incubation at 37° C. and acid wash, indicating phage internalization to the cells. Immunostaining and confocal imaging of cells incubated with individual phage clones confirmed intracellular localization of the phage particles (FIG. 2B).

Figure 3:
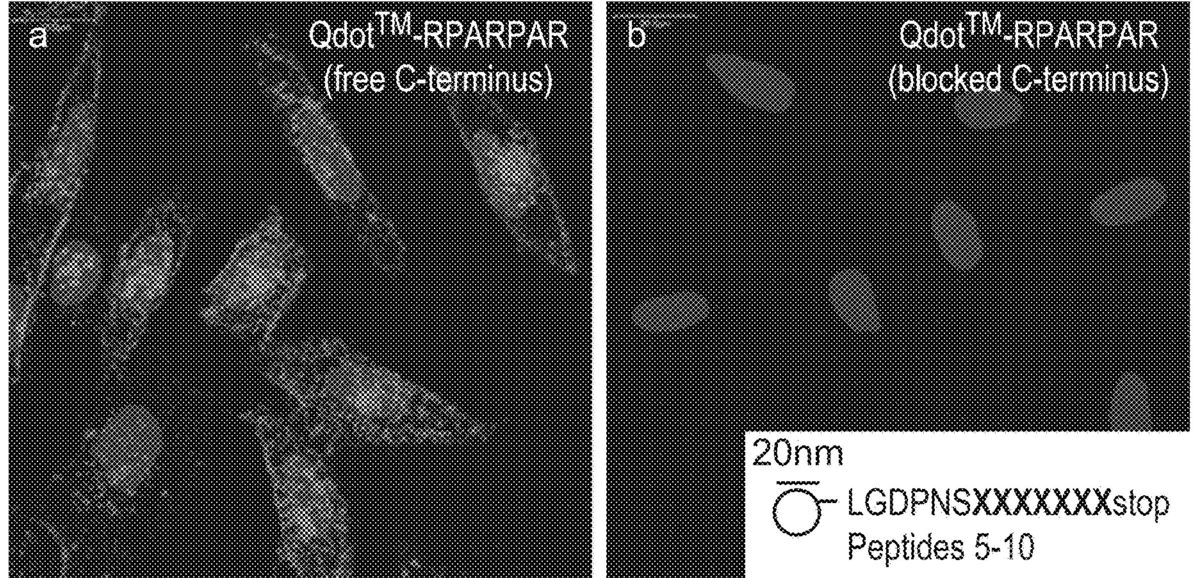
FIG. 3 shows that RPARPAR (SEQ ID NO: 2)-quantum dots are internalized by PPC1 cells. PPC1 prostate carcinoma cells cultured on collagen-coated coverslips were incubated with streptavidin quantum dots coated with biotinylated peptides, followed by fixation, counterstaining of cell nuclei with DAPI, and confocal imaging. Q-dots coated with RPARPAR peptide (SEQ ID NO: 2) with free C-terminus were robustly internalized (light colored dots) (a), whereas Q-dots coated with an amide-blocked C-terminus did not bind to the cells or get internalized (b). Inset: Schematic representation of Q-dots: the quantum dots used in this study have a diameter of about 20 nm and can be coated with 5-10 peptides per particle.

To understand the role of C-terminal arginine in phage internalization, two sets of phage displaying (1) GGGGGGR (SEQ ID NO:1) and other variants of the G7 control peptide, and (2) variants of one of the robust internalizing peptides, RPARPAR (SEQ ID NO: 2) were prepared. The binding of these phage to PPC1 cells (FIG. 2A) and several other human tumor cell lines in vitro and suspensions of cells prepared from normal mouse organs ex vivo was studied. These experiments demonstrated that C-terminal arginine is sufficient to trigger phage binding to a wide variety of cells. The RPARPAR (SEQ (ID NO: 2) phage showed stronger binding than the GGGGGGR (SEQ ID NO:1) phage. Consistent with universal cell binding, intravenously injected phage clones displaying C-terminal arginine exhibited enrichment in the first-met vascular beds, the heart and the lungs i. Display of C-Terminal Arginine Leads to Internalization of Synthetic Nanoparticles Next, the applicability of the C-end rule to synthetic nanoparticles was studied. Coating of the RPARPAR (SEQ ID NO:2) peptide onto quantum dots (Q-dots™, Invitrogen) triggered robust binding and internalization of the Q-dots by cultured PPC1 cells (FIG. 3, panel a). Blocking of the C-terminus of the RPARPAR (SEQ ID NO:2) peptide with amide abolished the binding and internalization of the Q-dots (FIG. 3, panel b). This is consistent with the notion that particle internalization uses both the guanido and carboxyl groups of the terminal arginine. The internalization of the RPARPAR-Q-dots (SEQ ID NO:2) was also inhibited by pre-incubation of the cells with an excess of RPARPAR-displaying phage (SEQ ID NO: 2), suggesting a saturable, receptor-mediated process.

The experiments described herein demonstrate that C-terminal display of an arginine residue represents a simple signal (CendR signal) that triggers robust phage (and more generally nanoparticle) uptake into cells.

ii. Activation of Latent Internalizing Compositions by Protease Cleavage

Figure 4:
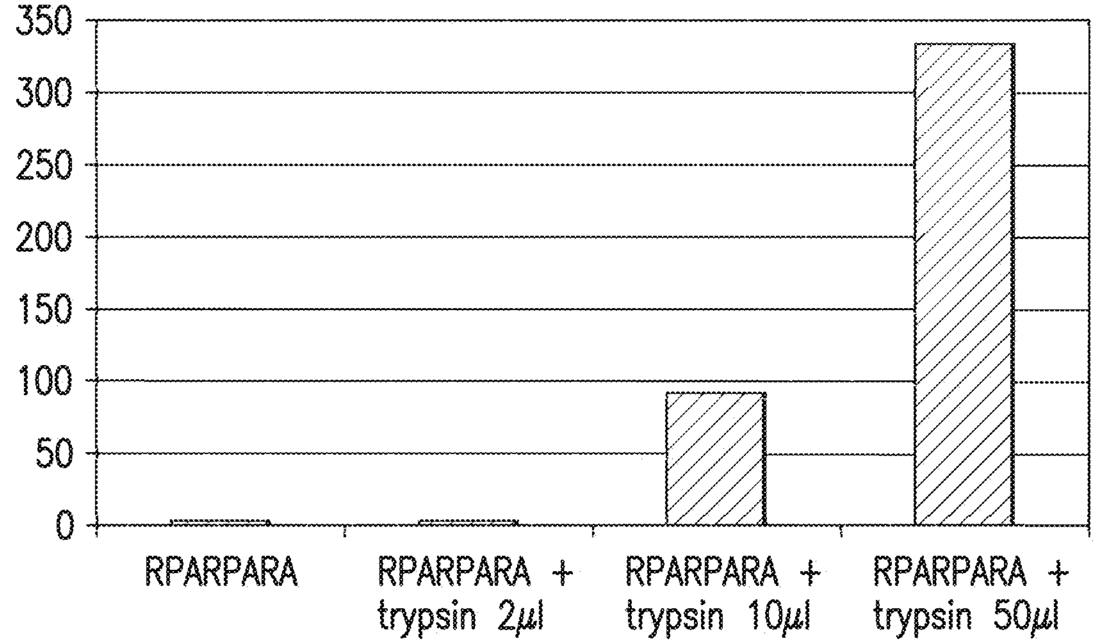
FIG. 4 shows that trypsin activates the binding of RPARPARA (SEQ ID NO: 3) phage to PPC1 cells. 5×10^8 phage particles were incubated with indicated volumes of 2.5% trypsin at 37° C. for 20 min, followed by incubation of the phage with 1×10^6 PPC1 cells at 4° C. for 3 hours. Binding is expressed as fold over non-binding G7 control phage (the internalization of which was not affected by the trypsin treatment).

The data show that the CendR defines a simple position-dependent element for uptake of various compositions. An interesting implication of the rule is that it can be used to design latent compositions, such as latent nanoparticles, that can be activated to internalizing nanoparticles by proteolytic cleavage. Many serine and cysteine proteases expose C-terminal elements (such as lysine, arginine, or lysine-glycine) and are potentially suitable for such cleavage-activation. Furthermore, extracellular proteases are often expressed in a highly regulated manner that can be specific to a cell type, tissue, or disease. This allows targeted proteolytic activation of nanoparticle uptake. Trypsin was used, a broad spectrum serine protease that cleaves exclusively on the C-terminal side of arginine and lysine residues, for proof-of-concept experiments on the protease switch idea. Phage displaying the RPARPARA (SEQ ID NO:3) peptide showed little cell binding (2.8 fold over G7-displaying phage) when incubated with PPC1 cells without trypsin treatment, but incubation of the phage with trypsin increased the binding more than 100 fold (FIG. 4).

iii. Tissue Selective Homing of Compositions and C-End Rule

Figure 5:
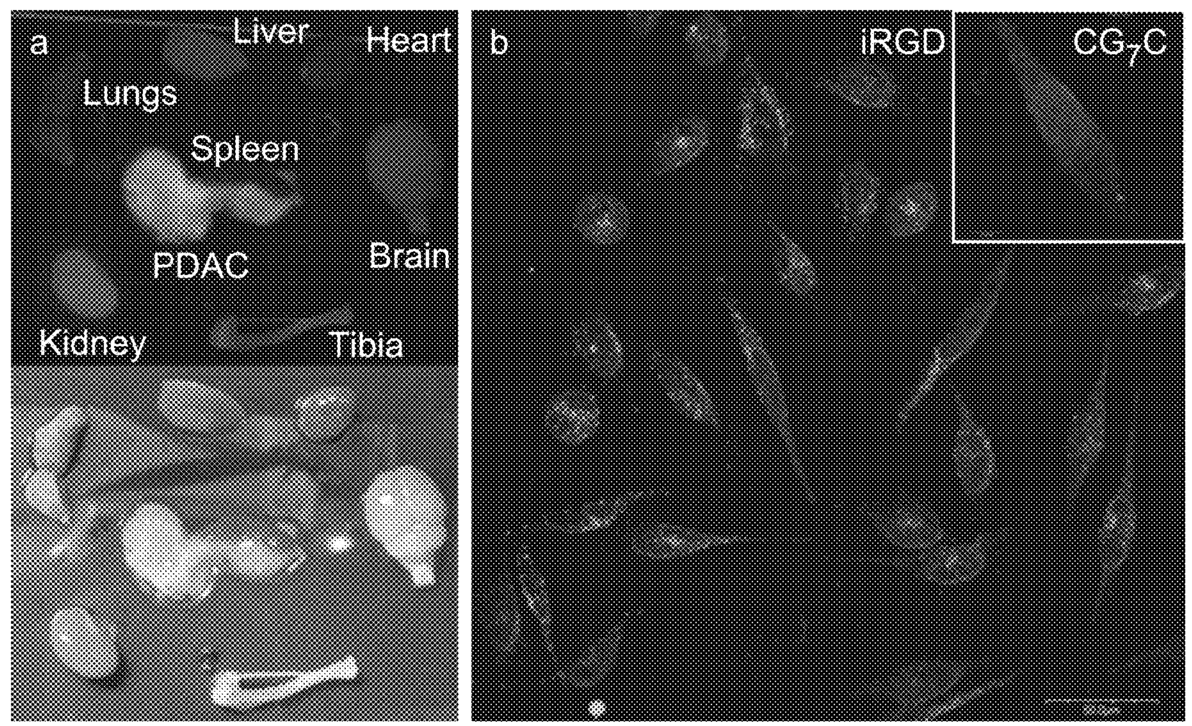
FIG. 5 shows tumor-homing and internalization of iRGD phage and iRGD peptide. a. iRGD peptide homes to pancreatic tumors. Approximately 200 μg of fluorescamine-labeled iRGD peptide was injected into a pancreatic ductal adenocarcinoma (PDAC) mouse through the tail vein, and was allowed to circulate for 4.5 hrs. The organs were harvested and observed under UV light (upper panel). The lower panel shows the corresponding bright field image. b. iRGD phage extensively internalize into human tumor cells. T7 phage displaying iRGD peptides (main panel) or $CG_7C$ control peptides (right upper window) were incubated with PPC1 cells cultured on collagen-I coated cover slips for 2 hours at 37° C., stained with anti T7 antibody and a plasma membrane marker, and imaged by a confocal microscope. Note that iRGD phage (light colored dots) internalizes extensively into the tumor cells, whereas the control phage does not.

A number of internalizing homing peptides previously identified contain an internal or C-terminal arginine (Laakkonen et al., 2002a; Hoffman et al., 2003; Zhang et al., 2005; Jarvinen and Ruoslahti, 2007). CendR can contribute to the cellular internalization of these homing peptides. Recently, a family of homing peptides that have strong in vivo selectivity to a number of tumor models was identified. One of these peptides, CRGDKGPDC (iRGD), SEQ ID NO:4, contains the integrin-binding RGD motif, but is unusual among the RGD peptides in that it is more strongly internalized into cells than any other RGD peptide, including the RGD-4C peptide previously used for tumor targeting (Arap et al, 1998). FIG. 5 shows an example of the strong tumor homing by the iRGD peptide.

Figure 6:
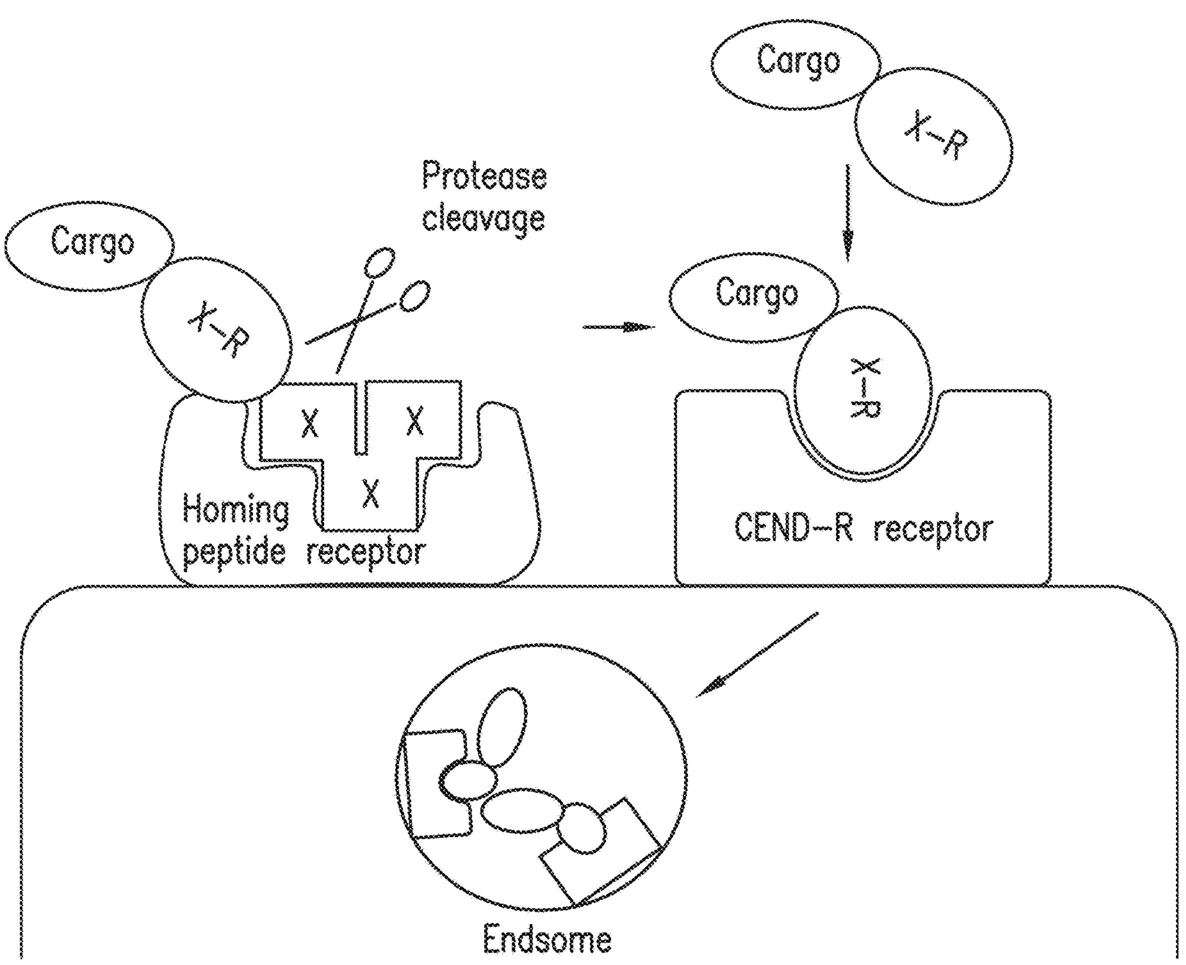
FIG. 6 shows CendR in specific intracellular delivery. A homing peptide that contains a latent CendR motif is brought to the surface of a target cell by binding to a specific receptor, such as an integrin, the peptide is subsequently cleaved by a specific cell-surface or pericellular protease to expose the CendR motif (C-terminal arginine), delivered to the ubiquitous CendR receptor, and endocytosed. A peptide with an exposed CendR motif interacts directly with the CendR receptor, and is internalized. The CendR pathway can enable highly specific intracellular delivery of diagnostic and therapeutic agents of all types, including nanoparticles.
Figure 8A:
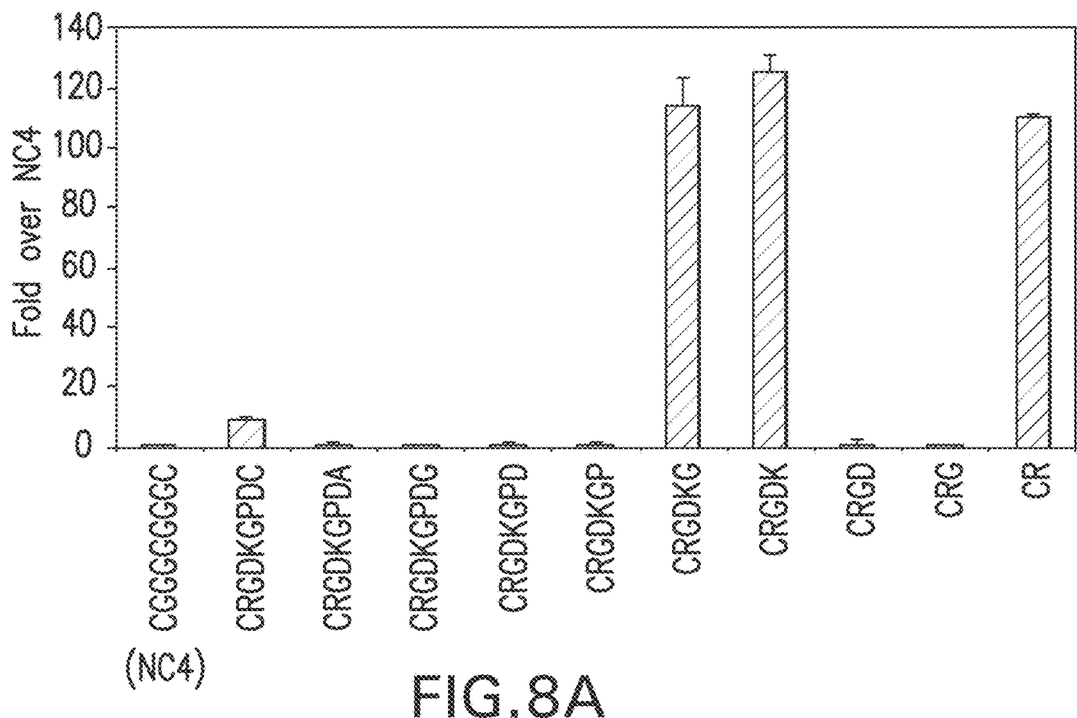
FIGS. 8A and 8B show that iRGD has a CendR element that has a C-terminal K (lysine) instead of C-terminal R (arginine), and that this CendR element behaves like other CendRs that have a C-terminal arginine. iRGD contains a CendR element.
Figure 8B:
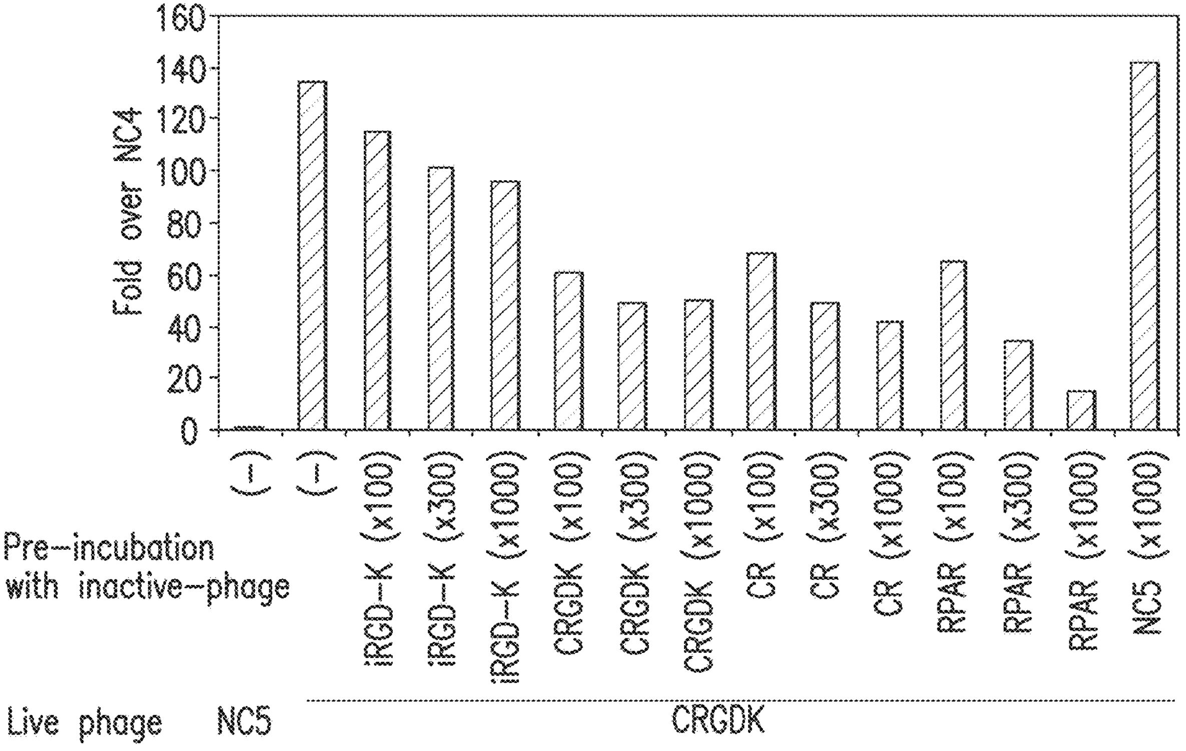

It appears that the key to the strong internalization is the RGDK sequence (the K can be substituted with an R, as shown in FIG. 8), which renders the peptide susceptible to a protease expressed in tumors. Selectivity and strong cellular internalization of iRGD peptide and iRGD-bearing particles can arise as a result of a combination of: (1) interaction with αv integrins on angiogenic endothelium and tumor cells, which results in a high concentration of the peptide in the tumor; (2) cleavage by to-be-defined tumor-derived extracellular protease(s) to expose a C-terminal arginine or lysine (the one in the RGD sequence); (3) subsequent activation of the CendR pathway leading to internalization of the particles that is more effective than the internalization pathway used by integrins. Results supporting this show that internalization of iRGD phage by cells of the phage displaying iRGD peptide is decreased by pre-incubation with UV-inactivated RPARPAR (SEQ ID NO:2) phage (and is unaffected by control G7 phage). FIG. 6 illustrates the concept.

2. Design and Methods i. Identifying Cell Surface Receptor(s) and Intracellular Proteins and Non-Proteins, and Elucidating Internalization Pathway for Nanoparticles Coated with Peptides that have C-Terminal Arginine.

The C-end rule is responsible for the binding and internalization of various compositions to multiple cell types. These processes can be inhibited by preincubation of cells with unlabeled particles displaying CendR element, consistent with dependence of uptake on specific cell surface receptor(s) and intracellular proteins and non-proteins (such as nucleic acids, lipids, and glycosaminoglycans). Identification and detailed understanding of the regulation of CendR receptor is an important prerequisite for rational application of the pathway for delivery. The internalizing receptor(s) for CendR peptides can be identified and characterized. The receptor/intracellular protein/non-protein is enriched by pulling down molecules that interact with the CendR peptides. Proteins co-purifying with CendR peptides are fractionated and subjected to mass spectroscopy analysis to identify the putative receptor(s) and other molecules.

A series of experiments are performed to validate the candidates as true receptor proteins. The interaction is confirmed by testing the purified putative receptor for the binding of CendR phage and colocalization of the CendR phage with the receptor in cultured cells. For functional analysis, expression levels of candidate CendR-receptor(s) are modulated and correlated with uptake of phage and quantum dots coated with a CendR peptide.

Colocalization studies using a panel of antibodies to markers of endocytotic compartments are used to determine the internalization pathways, and the sensitivity of CendR nanoparticle uptake to inhibitors of the various pathways is then tested.

Receptor identification and validation. To identify the CendR receptor, peptide pull down assays with extracts prepared from PPC1 prostate carcinoma cell line are carried out. $10\times10^6$ PPC1 cells are extracted with a buffer containing glucopyranoside (Sigma), $Ca^{2+}$ and $Mg^{2+}$, and a protease inhibitor cocktail for mammalian cells (Roche Biochemicals). The extract is incubated with agarose beads (Roche Biochemicals) that have been coupled to RPARPAR (SEQ ID NO:2) and control peptides (RPARPAR with blocked C-terminus and G7). All peptides will be synthesized by a peptide chemist associated with our laboratory. The peptides are purified by HPLC to greater than 95% purity and their structure is confirmed by mass spectrometry. After overnight incubation, the beads are thoroughly washed and separated on 4-20% polyacrylamide gel. After electrophoresis, the gel is silver stained and the protein bands specifically present in RPARPAR-pulldown samples will be excised and sent for MALDI-TOF analysis.

A variation of the pull-down assay can also be used, which includes the additional step of reversible cross-linking of the peptide to the receptor using dithio-bis(succinimidyl propionate) (DSP, Lomant's reagent). It is a cell permeant, homobifunctional, thiol-cleavable molecule, which is designed to link primary amino groups to one another in aqueous buffers at pH range 6.5 and 8.5. The resulting —S—S— bridge is cleaved by beta mercaptoethanol in gel loading buffer. A dedicated set of peptides that have additional amino-terminal cysteine is prepared for crosslinking-stabilized pull-down using DSP.

The procedure can be modified to make use of the expression of the receptor at the cell surface. In one variation, intact live cells are preincubated with the peptide-agarose beads, excess beads are washed away, and the cells are solubilized and the beads washed again. This limits the binding to cell surface proteins. Alternatively, the cells can be surface-biotinylated (Altin and Pagler, 1995), and the initial isolation can be carried out with peptide-agarose, and then biotin-containing proteins can be further isolated on streptavidin-agarose, prior to gel electrophoresis.

A cloning strategy for the CendR isolation can also be used. The cell lines routinely cultured (estimated to be about 30 different cell lines) can be tested for CendR peptide internalization. If a non-internalizing cell line is found, these cells are used to transfect a cDNA library of PPC1 cells and screen for transfectants that have acquired the ability to internalize quantum dots coated with a CendR peptide. Internalization-positive cells are identified and isolated by FACS. If no CendR-negative cell line is found, such a line is generated by treating the PCC1 cells with an intracellularly acting pro-apoptotic peptide. The first choice is the BH3 domain-derived pro-apoptotic peptide, which is known to suppress the activity of pro-survival molecules Bcl-2, Bcl-x (L), Bcl-w, Mcl-1 and A1 (Dharap and Minko, 2003). Surviving cells are selected for, until a cell line resistant to the treatment is obtained. This cell line is then tested for lack of CendR-quantum dot internalization. If the defect is not in the CendR step, alternating treatment with two independently acting proapoptotic compounds is used. The antibacterial peptide $_D$(KLAKLAK)$_2$ (SEQ ID NO:5) previously used for tumor targeting (e.g. Arap et al., 2002) is employed as the second compound in the alternative screening.

Candidate receptors identified by the above methods are validated using biochemical and cell-based assays. The purified putative receptor protein as bound to plastic wells and binding of phage displaying CendR (RPARPAR, SEQ ID NO:2) and control peptides (RPARPARA (SEQ ID NO:3) and G7) are analyzed in immunoassay format. If the interaction is confirmed, evaluation of the effect of receptor modulation on the CendR phage uptake is determined. A sub-line of prostate carcinoma cell line PPC1 with down-regulated receptor expression is formed by using stable transfection with pSilencer 2.0-U6 vector (Ambion) driving constitutive expression of siRNA (PPC1/R-). If a true CendR receptor is down-regulated, a suppressed CendR phage internalization is seen. As control for the specificity of the siRNA effect, siRNA insensitive expression constructs with alternative codon usage are generated. Rescue of CendR phage binding to PPC1/R-cells by transfecting these expression vectors can confirm that the effect of the siRNA knockdown is specific to the receptor and not due to involvement of other genes. The involvement of the CendR receptor or receptors identified in the internalization of some of the well-known cell-penetrating peptides are also tested (Tat, penetratin, pVec) to determine the generality of the CendR system.

Elucidation of internalization pathway. Confocal microscopy is used to study the localization of the internalized CendR nanoparticles and a panel of subcellular compartment markers. PPC1 cells are incubated with phage and quantum dots (Qdot™ 605 ITK-SA, Invitrogen) displaying RPARPAR (SEQ ID NO:2) peptide for various periods of time (10 min-3 hrs) and stain the cells with antibodies against markers for endosomes (anti-EEA1 pAb and anti-M6PR pAb; Abcam); lysosomes (anti-LAMP-1 pAb, caveoli (anti-caveolin1 pAb; Abcam), and clathrin (anti-clathrin mAb; Abcam). The cells are double stained for markers of the various internalization pathways and for T7 bacteriophage. Non-immune IgG serves as a control. For functional analysis, the effect of specific internalization pathway inhibitors on the uptake of the CendR and control particles are tested. Quantum dots are detected by fluorescence microscopy. The inhibitors employed are: low temperature (4° C.) as a general inhibitor for the endosomal pathway, filipin, cytochalasin D, and nystatin (Sigma-Aldrich) for caveolin-mediated uptake, chlorpromazine (Sigma-Aldrich) for clathrin-dependent endocytosis, amiloride (Sigma-Aldrich) for macropinocytosis, and chloroquine (Sigma-Aldrich) for lysosomal escape.

siRNA activity is a reliable and relevant measure of cytoplasmic delivery. An siRNA is synthesized for EGFP, coupled to the CendR peptide RPARPAR (SEQ ID NO:2), and test its effect on PPC1 cells that express both EGFP and DsRed. The control is plain siRNA. The treated cells are tested for EGFP and DsRed expression by fluorescence and immunoblotting. The siRNA is attached to the surface of nanoparticles, constructed as described below.

The receptor or receptors that mediate the cellular uptake of the CendR peptides are therefore identified. The particular endocytosis pathway used by these peptides is also identified, and whether cytoplasmic delivery is obtained is found.

ii. Applying Proteolytic Exposure of C-Terminal Arginine to Trigger Binding/Internalization of Latent Compositions In Vivo.

The requirement for C-terminal exposure of the CendR element makes it possible to construct latent (non-internalizing) nanoparticles that are activated by proteolytic cleavage. in vitro trypsin treatment converts a latent CendR peptide (RPARPARA, SEQ ID NO:3) into a potent internalization-triggering peptide. Here, the utility of proteolytically activated internalization of compositions in tumor delivery is explored.

The extracellular proteolysis machinery is a complex system of proteases with varying expression patterns, specificity and activity, and with each enzyme regulated by receptors, co-receptors and inhibitors. In a healthy adult, extracellular proteolysis is suppressed. A shift towards increased proteolysis takes place in pathological conditions that are associated with tissue remodeling and angiogenesis (e.g. tumor invasion and growth, neurodegenerative, vascular and inflammatory diseases). Many studies have established a link between tumorigenesis and activation of the extracellular serine protease system of plasmin and plasminogen activators. Of the two main plasminogen activators, urokinase type activator (uPA) and tissue type plasminogen activator (tPA), uPA is considered to be more important for pericellular proteolysis and tumor cell invasion. uPA is secreted from cells as proteolytically inactive single-chain pro-uPA, which is converted in the pericellular space into active two-chain uPA. In tumors, active uPA is present at the surface of invasive tumor cells, macrophages and angiogenic endothelial cells. uPA activity is precisely regulated by a set of functionally related molecules: high-affinity GPI-anchored cell surface receptor-uPAR (Blasi and Carmeliet, 2002), co-receptor-LDL receptor-related protein/2-macroglobulin receptor (Conese et al., 1995), serpin inhibitors-plasminogen activator inhibitors type 1-3 (Rijken, 1995). This system acts to confine uPA activity to the immediate pericellular space. The association of uPA activity with tumorigenesis and neovascularization, and its strong substrate selectivity, make it an attractive candidate for protease-activated targeting in vivo. Indeed, uPA-mediated activation of bacterial toxins has been successfully applied in experimental tumor therapy (Liu et al., 2001, Abi-Habib et al., 2004). uPA prefers arginine as P1 residue, and it can be suitable protease to catalyze C-terminal display of a masked CendR element. T7 phage displaying a CendR element is formed, followed by consensus uPA cleavage site, and its internalization is studied by uPA-expressing cells and sensitivity of the internalization to pharmacological inhibition of uPA activity. The controls include phage displaying a peptide with an alternative uPA substrate motif expected to lead to exposure of C-terminal lysine upon cleavage; this phage should not internalize. Two other proteases, furin and thrombin, both of which cleave proteins and peptides on the C-terminal side of a basic residue, potentially exposing a C-terminal arginine residue, are similarly tested for their ability to induce internalization. Once it has been demonstrated that the internalization of the uPA-CendR phage depends on uPA activity, the homing is studied in vivo in mice bearing uPA-expressing xenograft tumors and in placental tissue of pregnant mice (placental morphogenesis is a well-known model process of physiological uPA induction). Furin or thrombin can also be used for the in vivo studies.

iii. Construction of uPA-Sensitive CendR Phage and In Vitro Targeting Studies.

A panel of phage displaying C-terminally masked latent CendR peptides expected to be exposed by urokinase, furin or thrombin cleavage (Table 1). The uPA-sensitive motifs that are used have been successfully used to construct uPA-sensitive anthrax toxin variants (Liu et al., 2001). For motifs 1~4 in Table 1, cleavage of the substrate phage by indicated protease is expected to expose CendR element, leading to phage binding and internalization. In contrast, cleavage of motif 5 by uPA can expose a C-terminal lysine and not trigger internalization. In addition to substrate phage, control phage mimicking the post-cleavage status is constructed (Table 1, right column). Furin is ubiquitous in mammalian cells with subcellular localization in the trans-Golgi network, endosomes and plasma membrane; in the experiments it is expected the CendR pathway for furin-sensitive phage (phage 1 in Table 1) is universally activated and the phage to serve as a positive control. Thrombin is not present in cultured cells and addition of exogenous thrombin is used to trigger internalization of phage containing a thrombin-cleavable peptide in cell cultures (phage 2 in Table 1). In tumor tissues, cancer cells typically express uPAR, whereas stromal cells produce pro-uPA. Only few cell lines are known to produce both pro-uPA and uPAR. One example is the Lewis lung carcinoma cell line LL3, which produces both proteins. In vitro internalization of the substrate phage panel in the LL3 cells is studied. About $10^6$ LL3 cells will be co-incubated with $5\times10^8$ phage particles for 2 hrs at 37° C.; after extensive washes with DMEM containing 1% BSA the bound phage is rescued and quantified. As a control, uPA activity is inhibited by incubating the cells with the specific peptide inhibitor, upain-1 (CSWRGLENHRMC (SEQ ID NO: 6); 100 μM; Hansen et al., 2005), or with 1 mM amiloride hydrochloride (a less specific competitive inhibitor of uPA). These in vitro experiments can demonstrate the feasibility of uPA-mediated activation of CendR nanoparticles.

iv. In Vivo Homing of Protease-Sensitive CendR Phage.

In vivo homing of uPA sensitive CendR phage is studied using two targets: (1) implanted tumors (subcutaneous LL3 model and PC3 prostate carcinoma orthotopic xenograft model), and (2) mouse post-midgestation placenta (days 10-14 post coitum). LL3 and PC3 tumors are known to have a highly activated uPA system. In placenta, uPA is expressed both in trophoblast cells and in decidual endothelial cells. The placenta has several features that can facilitate targeting: the vasculature is normal, and the elevated interstitial pressure and EPR effect that are common in tumors, are absent. Nanoparticles (including bacteriophage) are rapidly cleared from the bloodstream by the reticuloendothelial system (the liver). If a long phage half-life is needed to see the proteolysis effect, a liver-avoiding mutant T7 phage is used. The mutations are in the tail fiber protein, and they render the phage unrecognizable by the liver, with consequent extended blood half-life. Such phage (Sokoloff et al., 2003) has been constructed and tested. uPA-sensitive CendR and control (G7) phage ($10^9$-$10^{11}$ pfu) are intravenously injected into mice, and after various periods of circulation (10 minutes to 2 hours), the animals are perfused with phosphate buffered saline (PBS) and tissue samples are collected. The tissues are homogenized, washed with DMEM containing 1% BSA, and phage quantity in target and control organs (typically brain, lung, heart, liver, spleen, kidney, and skeletal muscle) are evaluated by titrating live phage and by q-PCR assessment of phage DNA copy number. In addition, immunoperoxidase staining with rabbit polyclonal anti-T7 antibody is used to determine the tissue distribution of the phage. Several peptides that home in vivo to tumor extracellular matrix components, blood and lymphatic vessels, and tumor cells (Laakkonen et al., 2002a; Hoffmann et al., 2003; Brown and Ruoslahti, 2004; Pilch et al. 2006) have previously been characterized. Homing of uPA-sensitive CendR phage is qualitatively and quantitatively compared to phage displaying these previously identified homing peptides.

Tumors are known to have a tendency for increased blood clotting. Nanoparticles coated with a homing peptide, CREKA (SEQ ID NO:7), have been shown to bind to tumor vessels and cause blood clotting in them (Simberg et al., 2007). MDA-MB-435 tumor-bearing mice (used in original CREKA (SEQ ID NO:7) studies) are injected intravenously with CendR thrombin substrate phage (phage 2, Table 1) or control (G7) phage ($10^9$-$10^{11}$ pfu) and phage homing is studied as described for the uPA-sensitive phage above. Phage and thrombin immunoreactivities are studied using double immunohistochemistry with peroxidase and alkaline phosphatase as reporter enzymes. For enhanced clotting, thrombin-sensitive CendR phage and CREKA phage are coinjected, followed by quantification of homing and immunolocalization.

TABLE 1

Protease-cleavable and control phage used for in vitro and in vivo targeting studies. Cleavage sites in substrate phage are indicated by arrow. Proteolytically exposed C-terminal residues are in bold.

| | Substrate motif | Activating enzyme | Peptide sequence displayed in C-terminus of GP10 of T7 bacteriophage: Substrate phage | Peptide sequence displayed in C-terminus of GP10 of T7 bacteriophage: Mimic of post-cleavage substrate phage |
|---|---|---|---|---|
| 1. | Furin cleavage consensus | Furin | GGGRKK**R**↑STGGG- (SEQ ID NO: 8) Can be universally cleaved & internalized | GGGRKK**R**- (SEQ ID NO: 9) Can be universally internalized |
| 2. | Thrombin substrate | Thrombin | GGGLVP**R**↑GSGGG (SEQ ID NO: 10) Can be universally cleaved & internalized upon addition of thrombin to the cultured cells | GGGLVP**R** (SEQ ID NO: 11) Can be universally internalized |
| 3. | Plasminogen-derived sequence | uPA/tPA | GGGPCPG**R**↑VVGGG- (SEQ ID NO: 12) Can be cleaved & internalized by uPA/tPA-expressing cells | GGGPCPG**R**- (SEQ ID NO: 13) Can be universally internalized |
| 4. | uPA minimum optimal substrate | uPA | GGGPGSG**R**↑SAGGG- (SEQ ID NO: 14) Can be cleaved & internalized by uPA-expressing cells | GGGPGSG**R**- (SEQ ID NO: 15) Can be universally internalized |
| 5. | uPA alternative substrate | uPA | GGGPGSG**K**↑SAGGG- (SEQ ID NO: 16) Can be cleaved by uPA-expressing cells | GGGPGSG**K**- (SEQ ID NO: 17) Can be not internalized |

v. Screening for Novel Protease Cleavable, Cell Type and Tissue-Specific Peptides Internalized Via CendR Pathway The human protease repertoire, or degradome, consists of more than 460 proteases (Puente et al., 2003). The proteolytic activity profile is tissue type and disease-specific. In vivo profiling of systemically accessible endogenous proteases cannot be done using current techniques. The CendR element can be used for such a screen. Serine proteases comprise about ⅓ of known proteases and in many cases their cleavage exposes C-terminal arginine residue. Many cysteine proteases also prefer arginine as the P1 residue and can be suitable targets for a CendR screen. Several tissue and cell type specific proteases that are capable of exposing a C-terminal arginine upon cleavage are known. Urokinase/plasmin system is activated in migratory cells during development (e.g. trophoblast giant cells, neural crest cells) and in tumor invasion (Blasi and Carmeliet, 2002). Tissue kallikreins (a family of 15 closely related chymotrypsin-like proteases) is expressed in an organ and cell-type specific pattern; best known is the prostate specific expression of hK3/Prostate Specific Antigen. Substrate profiling shows that kallikreins hK4, hK5, hK6, hK10 prefer arginine as the P1 residue, with other important kallikreins such as hK3 also tolerating arginine at this position (Debele et al., 2006). Trypsinogens are physiologically expressed by the exocrine pancreas, but they are also ectopically expressed in many tumors and play a role in the activation of matrix metalloproteinases (Nyberg et al., 2006). Intriguingly, proteolytic cleavage of viral coat proteins by host protease(s) is an instrumental activating step for many viruses; in fact the expression pattern of an activating protease frequently determines viral tissue tropism (Klenk and Garten 1994). The viral coat protein is commonly cleaved at basic residues; this can represent nature's way of applying the CendR principle for intracellular delivery of viral particles. In addition to an endoprotease cleavage that directly exposes C-terminal arginine residues, one can envision CendR activation through a multistep trimming by carboxylpeptidases or a combination endoprotease and carboxylpeptidase processing. The need for simultaneous expression of more than one protease at or near the cell surface can generate a tremendous amount of tissue-specific variability and potential for selective targeting.

Figure 7:
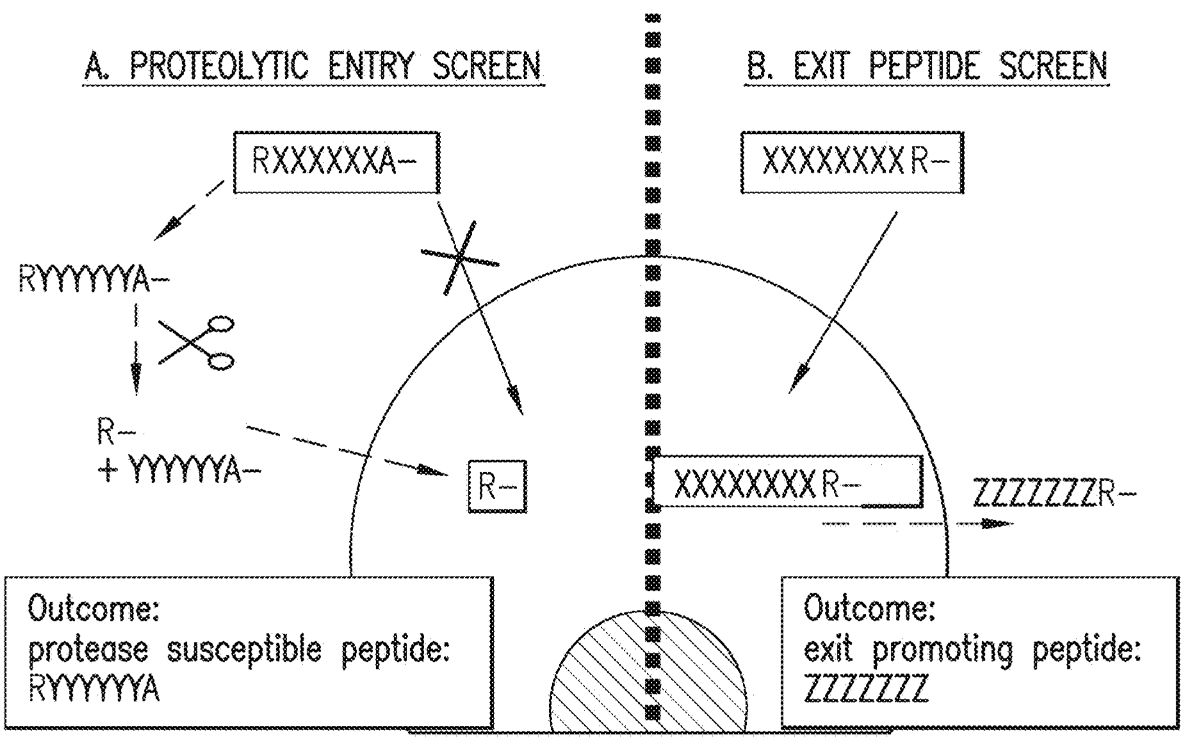
FIG. 7 shows a schematic representation of CendR screens for protease-activated entry and for exit signals. (A) For proteolytic entry screen CendR element (RPARPAR, SEQ ID NO: 2) is masked with random hexapeptide and C-terminal alanine residues. Phage found intracellularly has been proteolytically processed to expose CendR element. (B) To identify exit signals, a phage library with exposed CendR element preceded by random peptide is constructed. Default pathway for the phage is internalization, and only phage in which the random peptide encodes an exit signal are extracellular.

A novel in vivo phage screen can be used to exploit the potential of tissue-specific protease expression in targeting. Proteolytic exposure of peptides containing a suitable protease recognition element within the random library sequence can lead to cell internalization of the phage particles (FIG. 7). The internalization concentrates the phage at the target, providing the basis for selection of peptides that are specifically cleaved at the target. Both in vitro and in vivo screens are performed in this manner to discover new, tumor-specific CendR peptides.

Such peptides can be used to construct internalizing compositions that are specific for proteases or combinations of proteases in various types of tumors. Furthermore, the protease-based targeting can be combined with synaphic (docking-based) targeting to increase specificity and efficacy; a homing peptide that binds to a receptor at the target tissue is used to concentrate a chimeric peptide or the composition (such as a nanoparticle) decorated with two peptides at the target, where CendR-based proteolysis then cleaves the peptide and causes internalization. The combined effect can yield unprecedented targeting selectivity. The iRGD peptide described above can be an example of a peptide with such a combined specificity.

vi. Library Construction.

Two types of T7 phage libraries are constructed: (1) In one set of libraries, a single arginine residue is followed by a random peptide bait sequence). If the random sequence is intended to form a cyclic peptide, a cysteine residue is inserted on the N-terminal side of the arginine, and the random part has the structure $X_nC$). (2) In the second set of libraries, a known homing motif is followed by an arginine residue and random sequence. Proteolytic processing that exposes the arginine as the C-terminal residue causes internalization of the phage and accumulation at the target. In design #2, the known homing motif is intended to concentrate the phage in tumor tissue. One choice for the homing motif is the RGD-4C peptide. This peptide contains 4 cysteine residues within 9 residues and forms a tightly wound structure (Assa-Munt et al., 2001). It has been shown that RGD-4C homes to tumor vessels (Pasqualini et al., 1997; Arap et al., 1998), and because of its structure, it is relatively resistant to protease cleavage. That leaves the added random sequence to provide the protease substrate and internalization functions. Another choice is the CLT1 peptide; a tumor-homing peptide that recognizes clotted plasma proteins in tumor stroma (Pilch et al., 2006). This peptide has no arginine residues (the sequence is CGLIIQKNEC (SEQ ID NO:18), so again any internalization should be provided by the random sequence. DNA sequencing of a random set of 96 phage clones is used to assess library quality.

vii. Library Screening.

In vitro phage display screening is performed on cultured prostate carcinoma (PPC1, PC3) and breast carcinoma (MDA-MB-435) cells. The tumor cells ($10^6$ cells) are incubated with $10^{10}$ pfu of phage library at 37° C. for 2 hrs, followed by extensive washes with DMEM containing 1% BSA to remove unbound phage. Phage is amplified in *E. coli* BLT5403 cells and purified by PEG-8000 precipitation. Four rounds of selection are performed. To deal with possible inactivation of internalized phage, alternative rescue of phage is performed by PCR and back-cloning peptide-encoding inserts into T7 vector arms. This selection scheme results in enrichment of phage displaying peptides sensitive to extracellular proteases capable of activating CendR uptake. In vivo screening is performed by injecting $10^{10}$ phage intravenously to mice bearing xenograft tumors (from the cell lines listed above) and harvesting tissue after 10 min to 2 hrs (to allow proteases of different effectiveness time to act on the peptides). The phage is rescued and analyzed as described for the in vitro screens above. A combination of in vitro and in vivo screens are also used.

After the last selection round, 96 random phage clones from the pool are sequenced and any dominant peptide motifs is identified. The sequences that display a C-terminal arginine (due to the presence of a stop codon after the arginine residue) are discarded because their selection in the screening was likely caused by the already exposed C-terminal arginine. According to the results shown in FIG. 1C these phage represent one half- to two thirds of all the selected pools from the in vitro screens. This will likely be much less from the in vivo screens, as the phage with C-terminal arginine binds to other tissues before reaching the tumor. From among the remaining phage clones 3 clones representing each dominant motif are analyzed individually. In vitro testing measures cell binding and the sensitivity of the binding to low temperature and (2-macroglobulin (general protease inhibitors), 4-(2-aminoethyl)benzenesulfonyl fluoride (AEBSF, serine protease inhibitor, Roche Biochemicals), pepstatin A (aspartic protease inhibitor, Sigma), Z-Phe-Ala-FMK (cysteine protease inhibitor, Enzyme Systems Products), amastatin (aminopeptidase inhibitor, Sigma). These tests can demonstrate protease-dependent activation of the phage internalization, and define the type(s) of protease responsible for the activation. Additionally, the involvement of the CendR pathway in binding and internalization of selected peptides is identified. This is done using two approaches: (1) competition of phage binding and internalization by UV-inactivated CendR phage, and (2) Using PPC1 cells in which CendR receptor identified above has been knocked down using siRNA technology.

In addition to the phage studies, fluorescently labeled substrate peptides are prepared for resonance energy transfer (RET) studies. RET quenching occurs when there is overlap in the absorption and emission spectra of two fluorophores at a close proximity. The amount of quenching is dependent on the distance between the molecules as well as the extent of the spectral overlap. To evaluate peptide cleavage, peptides are labeled at different termini with known fluorophore/quencher pairs (e.g. DABCYL/EDANS or Abz/3-nitro-Tyr), peptides incubated with cells, and the shift in fluorescence intensity measured. The panel of protease inhibitors listed above for phage studies are used to identify the protease family responsible for cleavage.

The phage clones are also tested for tumor homing in vivo. Homing efficiency is gauged by titrating phage in tumors and in normal tissues. The presence of phage in tissues is analyzed using anti-T7 antibodies; this analysis gives information on the cell type the phage is associated with in tissues, and whether it is internalized into cells.

These screens can yield new, tumor-specific CendR sequences. Mixed sequences can also be found in which a homing peptide is embedded within a CendR sequence, or cooperates with one in a chimeric peptide. Peptides that bind to target tissue by such combined mechanism can be particularly good vehicles for selective intracellular delivery of compositions. The identification of protease cleavable substrates can also be used to identify proteases responsible for the cleavage. These proteases can prove functionally important for disease progression, and can be important druggable targets on their own.

viii. Isolating Peptides that Promote Exit of Compositions from the Cells and Peptides that Cause Nanoparticle Extravasation Efficient extravasation and tissue penetration of various compositions use both cell internalization and exit functions. Exit of compositions from cells may depend on hijacking of cellular secretory pathways. It is likely that there are multiple pathways that can be applied for exit; some of these pathways can be cell and tissue type-specific and can potentially provide an additional layer of selectivity to drug delivery. The C-end rule can be applied to screening for peptide sequences that can mediate exit from cells. To this end, T7 libraries displaying random peptides are created, followed by a CendR element with a C-terminal arginine (XCendR libraries). The C-terminal arginine causes indiscriminate cellular internalization of the phage. As only those phage displaying a peptide with exit function are capable of leaving the cells, a screen for an exit function is created. There are several possible ways to select for phage capable of exiting the cells. The most straightforward approach is to identify the phage that appears in the culture medium of cells after initial library binding and internalization, and washes to remove unbound phage. This system also allows one to select for phage that is capable of more than one entry/exit cycle. In this screen, the phage is allowed to bind to one pool of cells, followed by a mixed culture of these cells with another pool of the same cells bearing a sorting tag. The phage is recovered from the second pool of cells. This scheme is selective for peptides that are capable of repeated entry-exit cycles and thus acts as tissue penetration elements.

The possible existence of cell type-specific cellular exit signals is also explored. A variation of the screen described above for generic exit promoting peptides is used, except that selection is performed using two different cell lines. In a screen for exit element specific for cell line A, it is incubated with the XCendR-library, followed by co-culture with cell line B, extended culture and recovery of intracellular phage from cell line B. The peptides selected in this way are universally internalizing, however they are only capable of exiting cell line A, but not B. Cell type-specific exit peptides can provide additional selectivity for payload delivery. For example, peptides that trigger cargo exit from non-cancerous cells are used to achieve extravasation, tissue penetration and selective targeting of tumor cells.

Extravasation is the first step in tissue penetration of nanoparticles. It includes not only penetration of endothelial cells and pericytes, but also of dense extracellular matrix structures (basement membranes and collagen-rich matrixes). Phage bearing extravasation promoting peptide motifs are isolated by microdissection from target tissues of mice injected with XCendR libraries.

A T7 phage library (XCendR library) is constructed for identification of cellular exit-triggering peptides. C-terminal CendR peptide (RPARPAR, SEQ ID NO:2) is flanked on its N-terminal side by random heptamer library; phage displaying this library is internalized via the CendR pathway. On the other hand, phage displaying a peptide with exit function is capable of leaving the cells. Unless the entry/exit processes involve irreversible processing (e.g. proteolysis), the entry/exit cycle can repeat several times.

The experimental strategy to identify generic exit-promoting peptide sequences is outlined on FIG. 7, panel B. The library is first incubated at 4° C. with $5\times10^6$ PPC1 prostate carcinoma cells to bind the phage to the cell surface (incubation at 4° C. is used to avoid repeated cycles of internalization/exit of the phage, with possible risk of phage inactivation). During the first round of selection, the input phage number that is ca. 20 times the diversity of the library (typically $10^{10}$ plaque forming units) is used. After extensive washes with DMEM containing 1% BSA to remove unbound phage, the cells are incubated at 37° C. for various periods of time (to prevent cell death from becoming a factor, the time is kept as short as possible), and phage is rescued from the culture supernatant by infection of *E. coli* BLT5403 cells. This phage pool can contain phages that display an exit signal, and repeated screening can enrich those phage.

To isolate phage capable of another entry after having exited from one cell, the initial part of the screen is performed as described above, but after the binding step and wash, a 10× excess of PPC1 cells stably transfected with GFP is added, followed by incubation at 37° C. for 1 hr. After extensive washes, the GFP+ cells are isolated by FACS, and phage in these cells are rescued by infection of *E. coli* BLT5403 cells and/or by PCR-based back-cloning into T7 phage. During each round of selection, the number of phage recovered is evaluated by titrating infectious phage, and by qPCR of phage DNA. Phage bearing candidate exit motifs is evaluated individually using the same strategy as during the library selection. This approach selects for phage that is capable of more than one entry/exit cycle, and can lead to identification of peptide elements that allow cellular exit of nanoparticles.

Variations of the screening strategy described above are carried out to explore possible cell type-specific exit signals (FIG. 7, panel B). The exit signals of cell suspensions prepared from normal mouse organs (liver, kidney, prostate), normal human vascular endothelial cells isolated from umbilical cord (HUVEC; BD Bioscience), prostate cancer cell lines (PC3, Du145; both ATCC) and a breast carcinoma cell line (MDA-MB-435, ATCC) are explored. To identify cell type-specific exit peptides, $5\times10^6$ target cells are incubated at 4° C. with 20× the diversity of the XCendR library (typically $10^{10}$ plaque forming units), followed by extensive (4×) washes with DMEM containing 1% BSA to remove unbound phage. Then the target cells are co-cultured at 37° C. for 1 hr with a 10× excess of GFP-expressing PPC1 cells, which is known to have a high CendR pathway activity. During this step, PPC1 cells internalize the phage that exited from the initial target cells. After incubation, PPC1 cells are sorted out, acid washed (to remove surface-bound phage) and intracellular phage is rescued by infection and/or by PCR-based back cloning into T7 bacteriophage. The resulting phage should display peptides that enter/exit the target cells but are only capable of entering, not exiting, the PPC1 cells. Other combinations of different types of cells are tested in the same manner. The combination of endothelial cells and tumor cells will be a particular focus, as peptides that are capable of entering into and exiting endothelial cells, but can only enter, not exit, tumor cells would be particularly interesting as tumor-targeting peptides.

Finally, the XCendR library is screened in vivo to identify peptides that drive extravasation from blood vessels. Individual phage with HUVEC exit/CendR peptides for their ability to extravasate. As the library with exposed CendR peptide is expected to bind to all blood vessels in vivo, initial screens are performed and the technology is optimized using target organs that are first met by the phage after tail vein injection: the heart and the lungs. The phage is then injected into the left ventricle of the heart (Brown and Ruoslahti, 2004) to avoid preferential uptake by the heart and the lungs. For the in vivo extravasation screening, a highly concentrated library that has been purified using cesium chloride ultracentrifugation is used (it has been found that highly purified phage gives better screening results than unpurified or PEG8000-precipitated phage preparations). The library is injected at $10^{11}$ pfu/mouse in a total volume not exceeding 200 μl (to avoid pressure-induced vascular stress and damage). After circulation of phage for 3 hrs to allow extravasation and tissue penetration, tissues is snap-frozen and sectioned at 30 μm. Tissue sections are fixed with −20° C. methanol for 1 min, and counterstained. Vascular structures are eliminated using PALM microdissection system (Carl Zeiss GmbH, Germany). It has been determined that such treatment is compatible with phage survival. Tissue sections with eliminated vessels are solubilized in nonionic detergent (1% NP40 in LB bacterial growth medium) and phage is rescued. After several rounds of selection, candidate phage is selected for individual evaluation. Extravasation of individual phage is assessed using multiplex qPCR using Taqman probes and primers sets (BioRad IQ5 instrument) to quantify DNA copy number of both phage clones. As an internal control for the qPCR, G7 phage is co-injected with the audited phage. Distribution of candidate extravasating phage in target tissue phage is also studied by immunostaining with anti-T7 antibody.

After the library screening phase and identification/validation of phage displaying potential extravasating peptides, synthetic biotinylated peptides are prepared and conjugated to quantum dots (Qdot™ 605 ITK-SA, Invitrogen). Internalization/exit of quantum dots are evaluated in live cells in real time using a spinning disc confocal microscope. Quantum dots bearing cell type-specific exit (and CendR) elements are analyzed using the same imaging system; a mixed culture of cells bearing different fluorescent labels are used to study cell type-selective exit. A lentiviral expression system is used to express a panel of fluorescent proteins (GFP, YFP, DsRed, Venus) that can be rapidly introduced to cells to generate fluorescent sub-lines. For in vivo assessment, peptide-coated quantum dots are injected intravenously, organs are collected after 3 hrs of circulation, snap frozen and treated for immunofluorescence staining. Quantum dots are observed using a TRITC filter set, the same sections is also stained with a panel of cell type specific markers (CD31 for endothelial cells, epithelial membrane antigen/EMA for tumor cells, CD11b for macrophages, and podoplanin and LYVE-1 for lymphatic endothelial cells) and secondary antibody conjugated to Alexa488 dye (Invitrogen).

This strategy is designed to reveal unconventional cellular exit signals, which are known to exist. The peptide display screens can reveal peptides that are capable of utilizing these pathways to mediate exit from cells. It is a completely novel approach, and it can reveal signals that are extremely useful in causing extravasation and the transfer of various compositions from one cell to another.

ix. Demonstrating the Validity of the Protease-Triggered C-End Rule Approach by Devising an Experimental Therapy for Cancer The results detailed above show that two kinds of nanoparticles, bacteriophage and quantum dots, can be specifically delivered into the interior of cells by using C-end rule-based peptides for the delivery. Dextran-coated and pegylated 50 nm iron oxide nanoparticles are used as the scaffold to construct a multifunctional delivery vehicle. Others have used a similar scaffold for siRNA delivery (Medarova et al., 2007). A homing peptide provides the targeting and internalization function. The iRGD peptide is used as the targeting element on the nanoparticles because this peptide combines specific targeting to tumor vessels and tumor cells with internalization of the payload into the target cells. Other single or chimeric homing plus CendR element peptides can also be used. Similarly, any peptides that promote extravasation and spreading into tissues can be incorporated into the nanoparticles.

The targeting peptide additionally carries a near-infrared fluorophor for imaging. Optical imaging in mice is preferred because it is easier and cheaper in small animals than other imaging methods. However, the iron oxide core provides the option of using MRI, which is the method of choice in human patients. The payload is linked to the particle surface. siRNA can be used, which has enormous potential in the treatment of many diseases, including cancer, because it is possible to modulate so-called 'nondruggable' targets (Uprichard, S. L., 2005; Dykxhoorn et al., 2006). An endosomal escape function to the particles can also be used. A nuclear signal from cells that have been treated with fluorescein-labeled iRGD has been found.

A similar siRNA delivery vector has been constructed on a quantum dot scaffold (Derfus et al., 2007). Based on the fact that the iRGD peptide is extraordinarily effective in delivering phage and fluorescent peptide to tumors and direct comparison of the iRGD and F3 phage, the iRGD nanoparticles can show greatly enhanced homing and internalization activity.

Another choice is liposomes, which have also been used by others for siRNA delivery (e.g. Pirollo et al., 2007). Numerous other scaffold designs for siRNA delivery exist in the literature (e.g. Li and Huang, 2006; Bartlett et al., 2007). The particle scaffold is not important; the system is built on the efficacy and specificity of the homing/internalization/extravasation elements.

Various drug-dosing regimens are explored in vivo and the tumor burden over time is characterized. In vivo distribution of the particles over time is studied by optical imaging and by measuring tissue magnetization. The target for the siRNA suppression is a protein known as p32, gC1qR, or HABP (Grebrehiwet et al., 2002; Rubinstein et al., 2004). This protein is primarily a mitochondrial protein, but it is also expressed at the cell surface under some circumstances. p32 is the target of one of the tumor-homing peptides. The homing peptide, LyP-1, recognizes lymphatics and tumor cells in some, but not all tumors (Laakkonen et al., 2002a; 2004). It has been shown that a subpopulation of tumor macrophages also expresses p32 at high levels. Moreover, it has been shown that suppressing p32 expression with siRNA shifts tumor cell metabolism toward glycolysis, reduces cell growth and impairs tumorigenicity in vivo. By using this target, the efficacy of the particles in suppressing p32 expression in tumors is shown. As p32 is expressed at relatively high levels in the kidney and pancreas (part of its tumor specificity is derived from expression at the cells surface, which according to previous results is limited to tumors), it can also monitor the selectivity of the targeting by measuring p32 levels in these organs. The treatment studies can reveal whether p32 has potential in siRNA therapy of tumors.

Nanoparticle scaffold. Amino group-functionalized dextran-coated superparamagnetic iron oxide nanoparticles (50 nm nanomag-D-SPIO; Micromod Partikeltechnologie GmbH, Rostock, Germany) are used. "Nanoworms", elongated iron oxide particles, can be used rather than nanospheres. Nanoworms can ferry more payload to a target (Park et al., 2008). The synthesis of nanoworms is similar to the typical preparation of magnetic nanospheres (NS), involving reaction of Fe (II) and Fe (III) salts in the presence of dextran (Palmacci and Josephson, 1993). To achieve the worm-like morphology, the concentration of iron salts are made higher and a higher molecular weight of dextran (20 kDa) is used than in making spherical particles. The nanoworms are elongated, dextran-coated particles composed of a linear aggregate of 5~10 IO cores (50~80 nm). We Nanospheres, which are spherical, dextran-coated particles containing 1~2 IO cores (25~35 nm) can also be made. Liposomes, such as targeted liposomes (Simberg et al., 2007) can be used. Self-assembling micelles can also be used.

Coupling of PEG, peptides, and siRNA to nanoparticles. It has been found that the circulation half-life is highly dependent on the number of surface amine groups (functional group used for peptide conjugation), and the surface charge for both NW and NS (Park et al., 2007). As the number of surface amine groups and hence the net particle charge increases, the circulation time decreases, as has also been reported in the literature (Weissleder et al., 1995; Moghimi et al., 2001). Free surface amines can attract certain plasma proteins related to opsonization; maintenance of a surface charge (zeta potential) close to neutral seems to be important to achieve a long blood half-life. Attachment of PEG to aminated nanoparticles increases the circulation time, presumably by reducing the binding of plasma proteins involved in opsonization (Moghimi et al., 2001). The particles can have surface modifications for reticuloendothelial system avoidance (PEG), homing and internalization (iRGD peptide), endosome escape (pH-sensitive peptide; e.g. Pirello et al., 2007), a fluorophor, such as Cy7, and the siRNA payload, and possibly also an extravasation-promoting peptide. To accommodate all these functions on one particle, optimization studies are conducted to determine what proportion of the available linking sites at the surface of the particles any one of these elements should occupy to give the best combination of targeting/internalization and payload delivery. The possible advantages of coupling of these compounds in tandem, rather than individually, can also be explored. At one extreme, the homing/internalizing peptide, the endosomal exit peptide, the extravasating peptide, and the fluorophor can all be synthesized as one compound and coupled to the particles through the PEG moiety. The other extreme is coupling all of them individually. Particles that incorporate scrambled peptides and control siRNA are constructed and used as controls.

The iRGD peptide, and other recent, highly efficient homing peptides are cyclic peptides with a disulfide bond that is essential to peptide activity. Chemistries have been developed to solve this problem; selective side group protection is used to synthesize cyclic peptides with an extra cysteine that presents a free sulfhydryl group. These peptides have turned out to be stable with no detectable scrambling of the disulfide bond. A maleimide function can also be used as a coupling group. These chemistries are used to couple iRGD to the particles. The siRNA payload is coupled to the particles by using a disulfide bond. It was shown in an earlier study that siRNA attached to a nanoparticle by disulfide cross-linkers showed greater silencing efficiency than when attached by a nonreducible thioether linkage (Derfus et al., 2007). This is presumably because the siRNA is released from the particle in the reducing intracellular environment.

x. Nanoparticle Uptake and Activity In Vitro and In Vivo.

Binding and uptake by cultured cells are studied by fluorescence microscopy, using confocal microscopy to determine internalization and subcellular localization. The circulation time of intravenously injected nanoparticles is determined by measuring fluorescence in blood samples collected at various times and by SQUID (Superconducting Quantum Interference Device) magnetometry. SQUID provides a direct measure of the total number of magnetic IO nanoparticles in a sample (rather than the total iron content), and the measurements are relevant to MRI imaging applications. SQUID is also used to determine nanoparticle concentrations in tumors and other tissue samples. The effect of the siRNA is monitored by immunoblotting of the target protein, and of several non-target proteins to ascertain specificity of any suppression.

xi. Tumor Models and Analysis of Targeting.

The main tumor model is an orthotopic breast cancer xenograft model generated by implanting MDA-MB-435 human cancer cells into the mammary fat pad of female nude mice. This model was chosen because the iRGD peptide and several other homing peptides available as alternative targeting elements effectively home to this tumor (CREKA, LyP-1). Furthermore, this mode has been used extensively in peptide homing and tumor treatment studies (e.g. Laakkonen et al., 2004).

Starting with clinically relevant concentrations (0.7 mg-2.6 mg Fe/Kg of body weight), the siRNA-carrying nanoparticles are intravenously injected in a mouse through the tail vein and optical images of the live animal under anesthesia are taken at 1, 8 and 24 hours thereafter. Organs harvested at appropriate times after nanoparticle injections are imaged and subjected to SQUID analysis to quantify homing. The effect of the siRNA is determined by immunoblotting as described above. The multifunctional nanoparticles are demonstrated to selectively target tumors and deliver an active siRNA into them.

Tumor treatment study. MDA-MB-435 tumor-bearing mice (at 16-20 weeks of age) are treated with nanoparticles or other suitable compositions as disclosed herein are selected following the criteria discussed above. The mice (10 mice per group) receive weekly intravenous injections. The dose for the particles with the specific siRNA and control siRNA is determined, in which siRNA effect on the tumor and toxicity is monitored. The dose is determined relative to toxicity. The efficacy and toxicity of the targeted nanoparticles are studied in regimens that increase the frequency of administration from weekly to 2-3 times per week. It is possible that the thresholds for efficacy and toxicity are more favorable with an increase in frequency and a lower dose per injection (Kerbel and Kamen, 2004).

The size of the MDA-MB-435 tumors can be easily monitored by measuring the dimensions and by weighing the tumor mass at the end of the experiment. The mice are euthanized when their tumors reach a size that causes the mouse noticeable discomfort. The personnel at the animal facility make euthanasia decisions independent of the researchers involved in the study (Arap et al., 2002). This arrangement allows for the collection of survival data for comparison of the groups. The optical (and potentially MRI) imaging methods discussed above offer an alternative to measuring tumor size or using survival as the end point. The availability of imaging enhances and speeds up the ability to test variations in the design.

As an additional measure of efficacy, the lymphatic vessels and macrophages are qualified (the target cells that are p32-positive, in addition to the tumor cells). The lymphatic vessels are analyzed with anti-LYVE-1 and the macrophages with CD11b staining. It has been shown that the p32 positive cells express these lineage markers (Laakkonen et al., 2004; Fogal, Zhang, and Ruoslahti, Mitochondrial/Cell surface protein p32/gC1qR as a molecular target in tumor cells and tumor stroma. Cancer Res. 68:7210-7218 (2008)). The presence of tumor cells in the lymphatics are also assessed, and the spreading of the tumors along the lymphatics are macroscopically and histologically evaluated. A substantial reduction in lymphatic vessel number can be detectable (Laakkonen et al., 2004). The microscopic examination can also make possible assessment of necrosis in the tumors, as extensive necrosis can skew the tumor size measurements.

The information generated herein can advance the targeted nanoparticle technology to a point where compounds for clinical studies can be developed. The steps that lead to a diagnostic or therapeutic reagent include the following: (1) Determination of the ability of the homing peptides to bind to the human receptor and optimization of the peptides for binding to the human receptor molecule and for pharmacokinetic properties. (2) Development of targeted compositions for therapeutic application; the p32 siRNA proposed herein as a model compound can be used for human therapeutic use, and can also be adjusted to carry other payloads.

B. Example 2-C-End Rule: Neuropilin-1 Dependent Internalization of Peptides and Peptide-Coated Nanoparticles Exposing a C-Terminal Arginine Cell type selective internalization of payloads is important for many biological processes and for targeted delivery of drugs and imaging agents. It has been established that cellular internalization and tissue penetration of nanoparticles can be achieved by C-terminally exposed R/KXXR/K (SEQ ID NO:23) peptide motif. This phenomenon is called the C-end Rule (CendR). Peptides containing R/KXXR/K (SEQ ID NO:23) motif in positions other than C-terminus are not internalized; however, uptake of such latent CendR peptides can be triggered by proteolytic cleavage. CendR peptides enter into cells by a mechanism that involves a critical component called neuropilin-1, which is a multiligand receptor known for its roles in vascular and nervous system patterning. The CendR technology can be applied to develop protease-activated delivery systems specific for individual cell types or tissues. It can also interfere with pathological processes involving the CendR mechanism, such as entry of viruses and other micro-organisms, and their products into cells.

Selective targeting of diagnostic and therapeutic agents into diseased tissues, especially tumors, remains an important challenge. Stretches of cationic amino acids drive transduction of endogenous proteins and are important for viral infection and spread. Examples of such proteins include homeodomain transcription factors such as Antennapedia (Joliot, A., et al. 1991), the herpes simplex virus-1 protein VP22 (Elliott, G. et al. 1997), and the human immunodeficiency virus-1 transactivator TAT protein (Green, M. et al. 1988, Frankel, A. et al. 1988). Short cationic cell penetrating peptides (CPP) derived from these proteins retain their ability to internalize a wide range of cargoes: heterologous peptides and proteins, nucleic acids, and nanoparticles (Langel, Ülo, 2007). However, the CPP are not selective; they are taken up into nearly all types of cells. The lack of selectivity severely limits the use of CPP for clinical applications. Tissue-specific internalizing peptides that are capable of synaphic (docking-based) delivery are also known (Laakkonen, P. et al. 2002b, Porkka, K. et al. 2002, Hoffman, J. A. et al. 2003, Jarvinen, T. A. et al. 2007). The mechanisms of the cellular uptake are poorly understood for all CPP.

A proteolytic switch frequently modulates activity of proteins in biological processes (Esmon, C. T. 1993, Barrettw et al. 1998, Sternlicht, M. D. et al. 2001). Examples include blood coagulation and fibrinolysis, activation of growth factors and peptide hormones, cell death-survival decision making, and cell migration and adhesion. Intriguingly, viral entry into the cells and internalization of many bacterial toxins are regulated by proteolytic activation (Klenk, H. D. et al. 1994, Gordon, V. M. et al., 1995); the expression pattern of an activating protease is frequently a determining factor in the entry into the target cells.

Described herein is an internalization system that can be activated by a proteolytic switch. The system is based on an internalizing peptide motif, R/K/XXR/K (SEQ ID NO:24). This motif must be present at the C-terminus of a polypeptide chain to be active (hence the term C-end Rule or CendR). The internalizing receptor was identified as neuropilin-1 (NRP-1). It is also shown that when embedded in a protein or peptide sequence, the cryptic R/K/XXR/K (SEQ ID NO:24) motif can be exposed by a protease, triggering cellular uptake. The findings highlight a cell penetration switch that can be used for targeted drug delivery and that can be operative in a multitude of biological processes such as viral infection. Sugahara, K. N. et al. (2008) describe a composite peptide that encompasses both a tissue-specific targeting element and a cryptic CendR element. The targeting element concentrates the peptide at the target, where a tissue protease exposes its CendR element, facilitating internalization and tissue penetration.

1. Results i. Identification of a C-terminal Internalization Element

C-terminal display of peptide libraries were used on the surface of the T7 phage (Hoffman, J. A. et al., 2004) to identify peptides that trigger cellular internalization of nanoparticles to the cells derived from PPC-1 human prostate carcinoma xenograft tumors. The peptide libraries used for selection were linear X7 library, cyclic CX7C, as well as constrained RXXRXXX (SEQ ID NO:19) library designed to include the RXXR (SEQ ID NO: 25) motif, which were also present in some internalizing homing peptides (X, random amino acid; C, cysteine; R, arginine, FIG. 10). After 3 rounds of selection, the selected phage pools bound to PPC-1 cells 500-1,300 fold over the control phage displaying a 7-glycine (G7) control peptide (FIG. 10A). Sequencing of random phage isolates demonstrated that, independent of initial library configuration, all libraries had converged to display a C-terminal arginine, in most cases in the (R/K) XXR (SEQ ID NO:26) context (FIG. 10B). The T7 phage was sensitive to acidic conditions and acid wash of cells in glycine buffer (pH 2.5) which leads to release and inactivation of extracellular phage. Phage displaying (R/K) XXR (SEQ ID NO:26) motif were recovered after the cells had been incubated at 37° C. and washed with the acidic buffer, indicating internalization. One peptide indicated that a lysine residue at the C-terminus could also produce an active peptide.

Figure 11A:
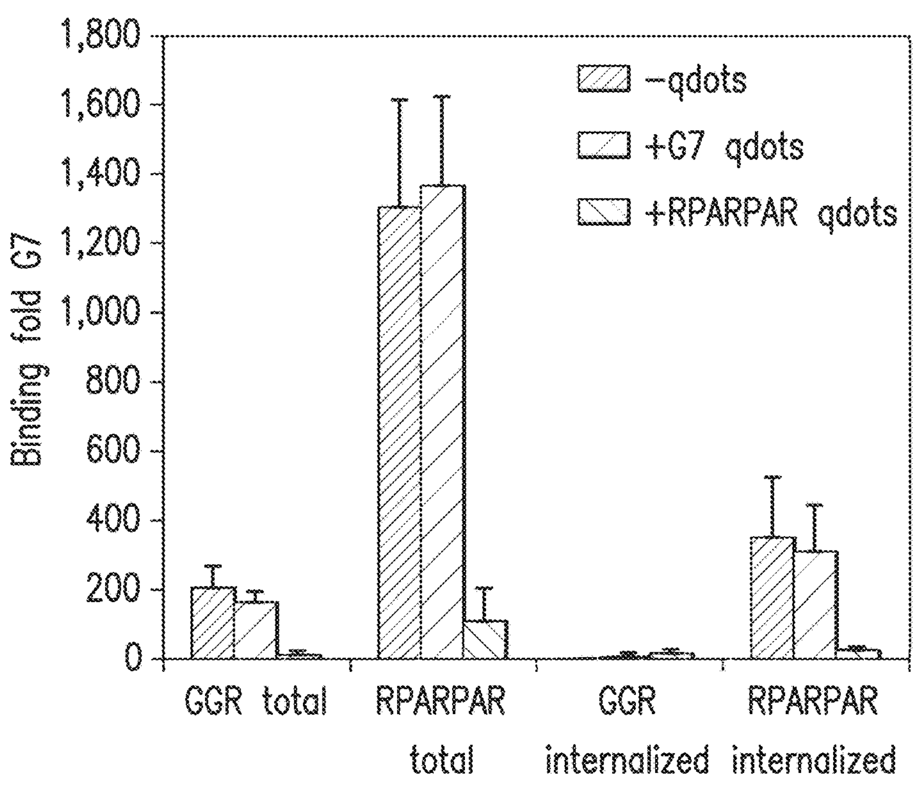
FIGS. 11A-11C show the structural features of CendR internalization.
Figure 11B:
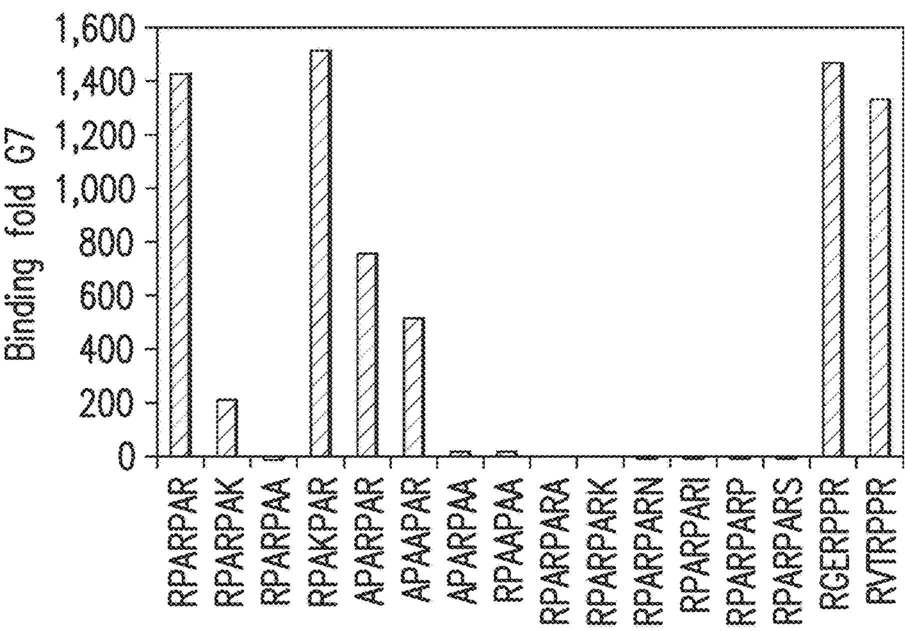
Figure 11C:
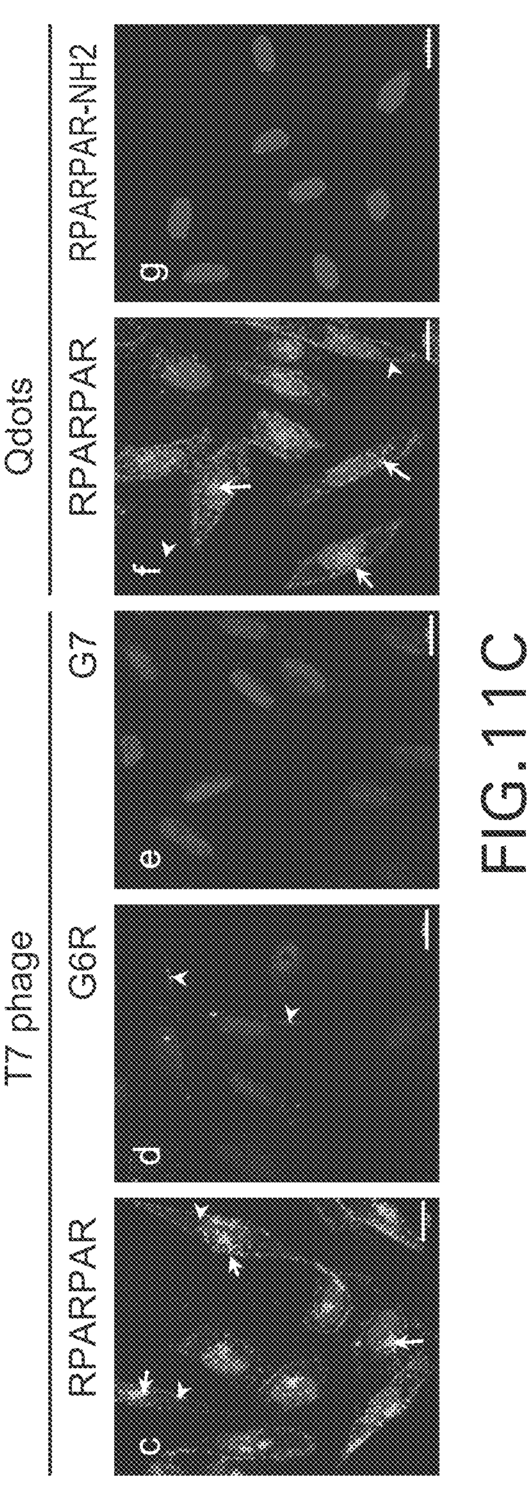
Figure 12B:
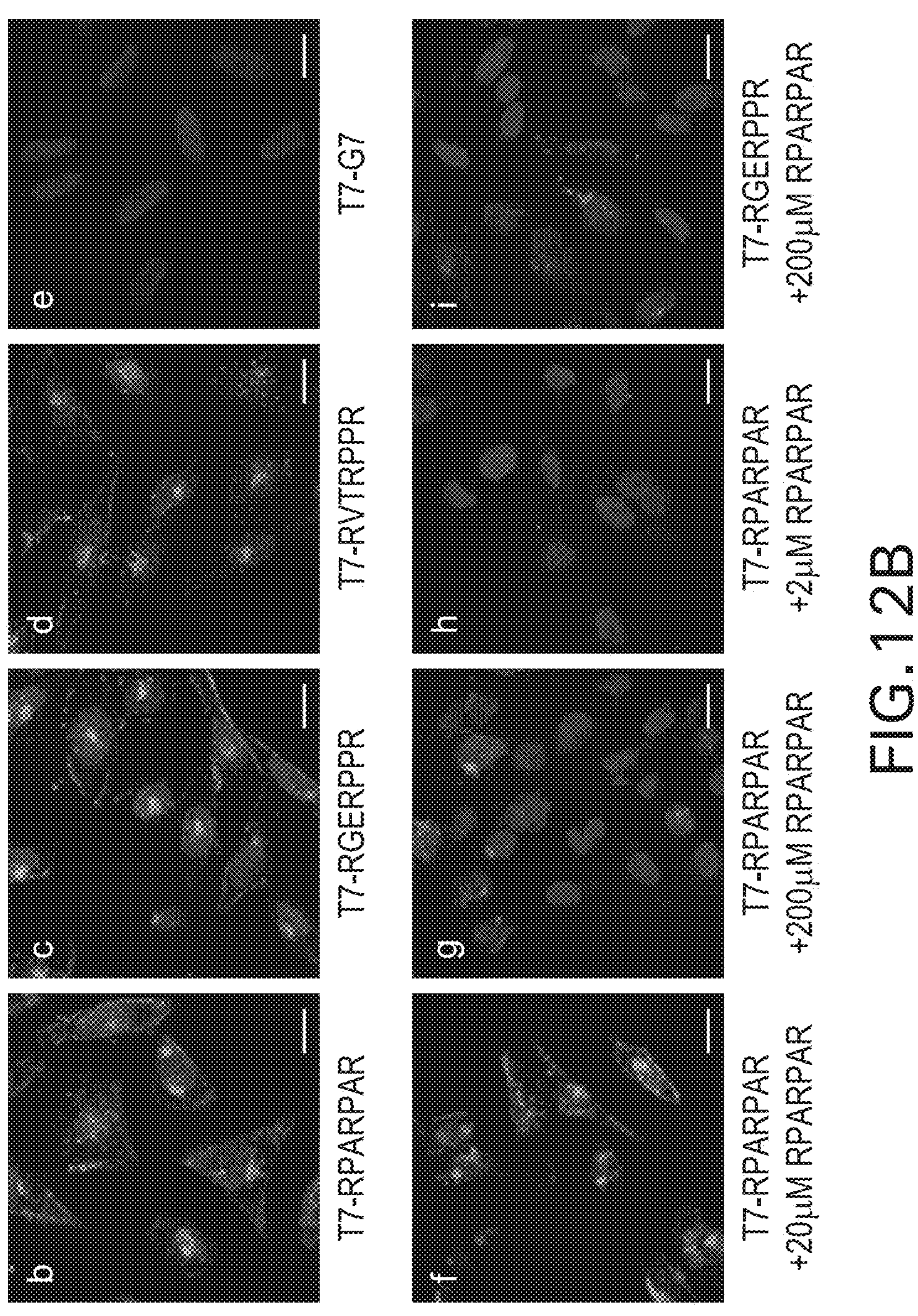

Binding studies using individual phage from selected pools showed that, while the presence of C-terminal arginine (as in G6R) alone was sufficient for weak phage binding to the PPC-1 cells (FIGS. 11A and 11C, panel d), robust binding and internalization can be seen in the presence of an RXXR (SEQ ID NO:25) motif, as in RPARPAR (SEQ ID NO:2) (FIGS. 11A, 11B, and 11C, panel c), RGERPPR (SEQ ID NO:27) and RVTRPPR (SEQ ID NO:28) (FIGS. 12A and 12B, panels c, d). Similar structure of the internalizing RXXR (SEQ ID NO: 25) peptides and their ability to compete with each other (FIGS. 12A and 12B, panel i) indicated a shared binding mechanism. RPARPAR (SEQ ID NO:2) peptide was used as a prototypic CendR peptide in subsequent studies.

Figure 13:
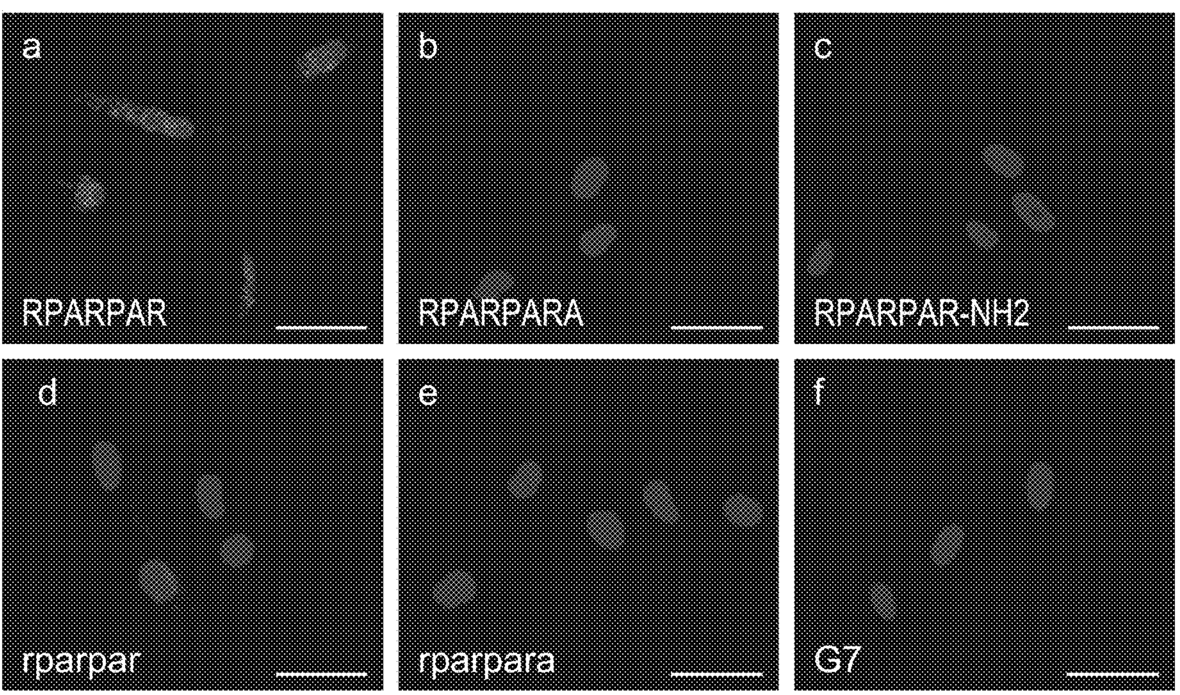
FIG. 13 shows the internalization (light colored dots) of RPARPAR (SEQ ID NO: 2) qdots by PPC-1 cells: Effect of peptide modification. PPC-1 cells were incubated for 2 hours with qdots functionalized with the following peptides: (a) RPARPAR (SEQ ID NO:2), (b) RPARPARA (SEQ ID NO:3), (c) RPARPAR-$NH_2$ (SEQ ID NO:2), (d) D-rparpar, (e) D-rparpara, and (f) G7. Cells were stained with nuclear stain DAPI and imaged using confocal microscope. Scale bars: 50 μm.
Figure 14:
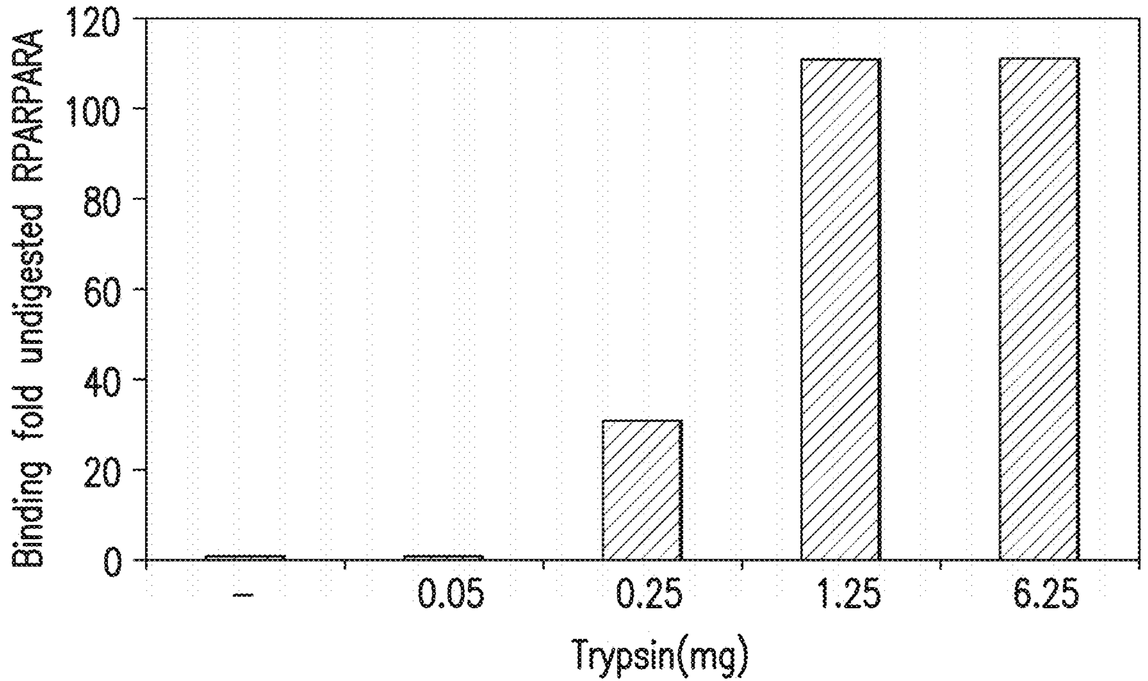
FIG. 14 shows that trypsin cleavage enhances binding of RPARPARA (SEQ ID NO: 3) phage to the PPC-1 cells. $10^9$ pfu of RPARPARA (SEQ ID NO:3) phage was treated with indicated amounts of trypsin at 37° C. followed by phage binding assay at 4° C. The data are representative of 4 independent binding experiments.
Figure 15A:
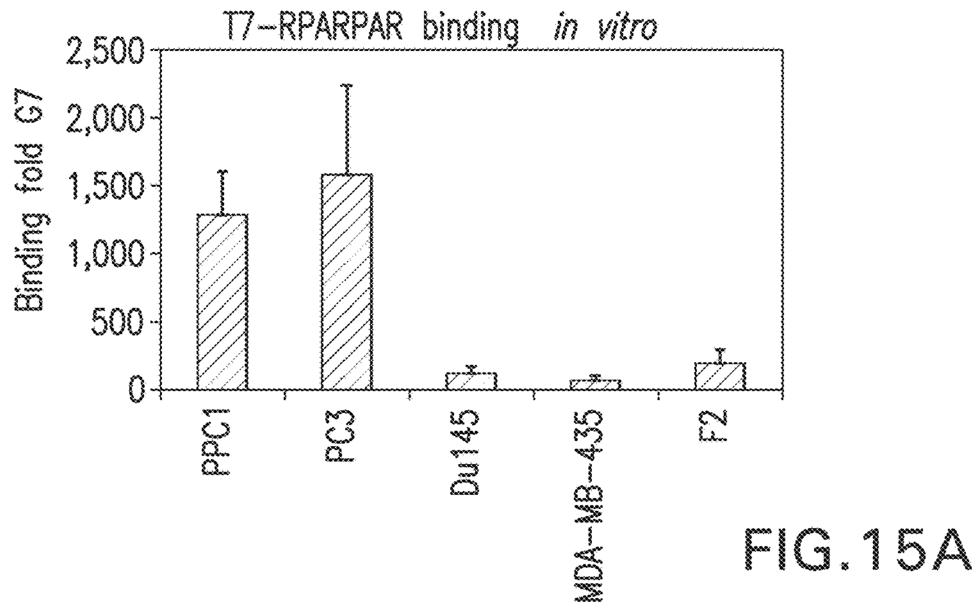
FIGS. 15A-15D show that CendR phage binds to many types of cells.
Figure 15B:
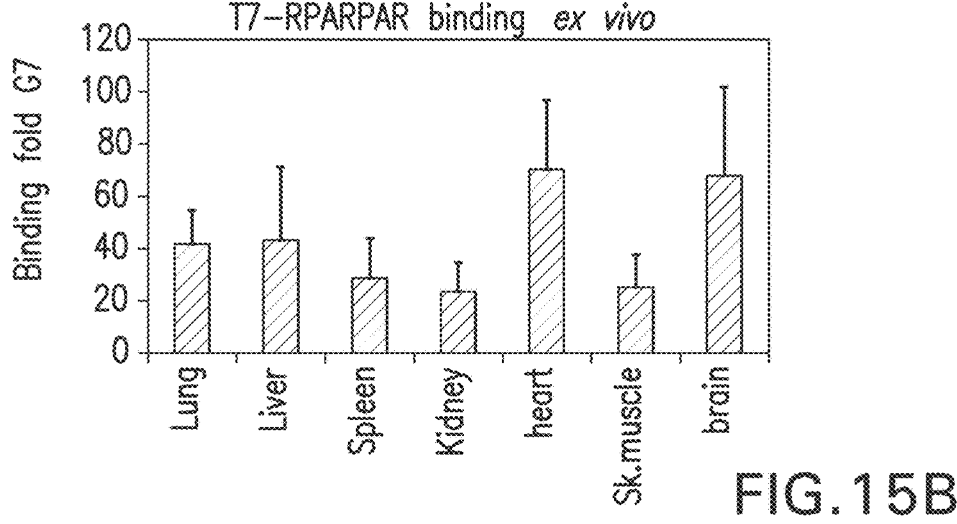
Figure 15C:
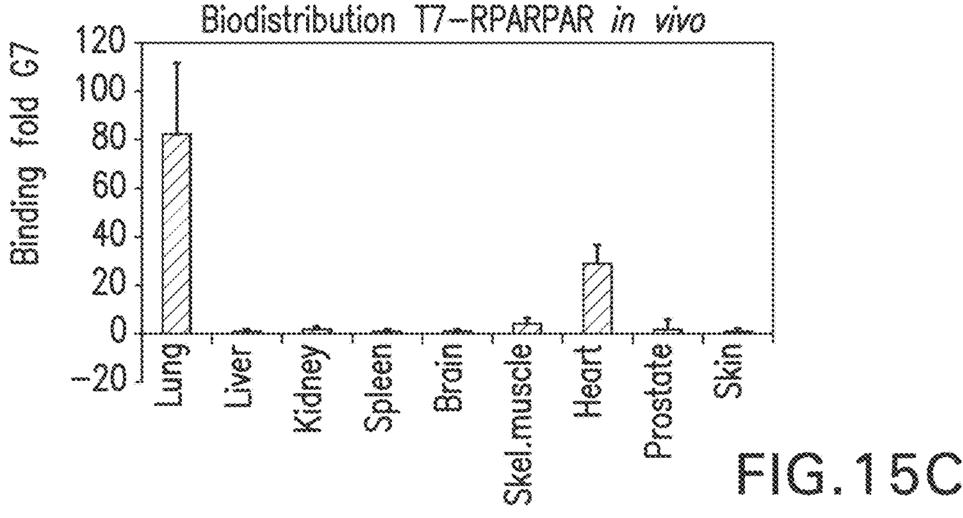
Figure 15D:
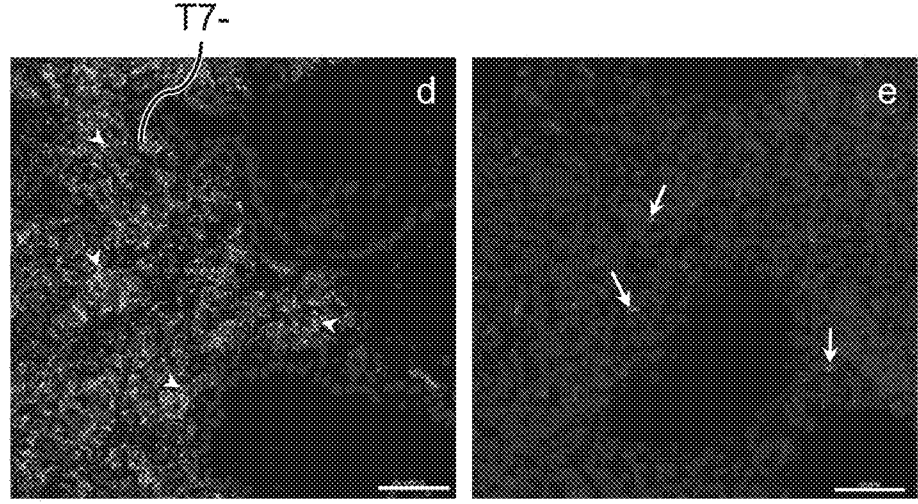

Structural features of the internalizing peptides were assessed to define the contribution of individual arginine residues to RPARPAR (SEQ ID NO:2) phage binding. It indicated that C-terminal arginine (or lysine) was critical for phage binding, and the other two basic amino acids increase the interaction in a dose- and position-dependent manner (FIGS. 11A and 11B). The interaction with cells did not involve other phage elements, as RPARPAR (SEQ ID NO:2)-functionalized quantum dots (qdots) bound and were internalized in a manner indistinguishable from the phage particles (FIG. 11C, panels f, g, and FIG. 13, panels a, f). Interestingly, a peptide comprised of D-amino acids (D-rparpar) had a greatly reduced ability to trigger uptake of quantum dots (FIG. 13, panel d), indicating the involvement of a chiral binding site. Masking the C-terminal RXXR (SEQ ID NO:25) element with an additional C-terminal amino acid (as in RPARPARA (SEQ ID NO:3)) abolished the binding of phage to PPC-1 cells (FIG. 11B); binding of RPARPARA (SEQ ID NO: 3) phage was restored by treatment of the peptide with trypsin (which cleaves after basic residues and presumably exposes a C-terminal arginine; FIG. 14). Internalization of qdots was similarly prevented by addition of an alanine to the C-terminus of the RPARPAR (SEQ ID NO: 2) peptide (FIG. 13, panel b). Amidation of the C-terminal carboxyl group also blocked qdot internalization (FIG. 11C, panel c). These findings indicate that internalization occurs in the presence of terminal basic amino acid with a free carboxyl group. Collectively, the library screening and structure-function studies define the CendR motif (R/K) XX (R/K) (SEQ ID NO: 23) as a trigger for peptide and nanoparticle uptake into PPC-1 cells.

ii. Characterization of CendR Internalization

To assess conservation of CendR internalization mechanism binding of the RPARPAR (SEQ ID NO:2) and its derivatives were studied to different target cells: a panel of cultured human cell lines and primary cells derived from several normal mouse organs (FIG. 15). Tumor cells of different origin bound the RPARPAR-phage (SEQ ID NO:2), including prostate cancer cells other than PPC-1 (PC-3, Du-145), breast cancer (4T1), and pancreatic carcinoma (MIA PaCa-2, PDAC1.3), melanoma cells (B16F10) and MDA-MB-435 human cancer cells. CendR phage binding was also seen with murine vascular endothelial cells (F2) and human umbilical vein endothelial cells (HUVEC). An exception was M21 melanoma cells, which did not bind RPARPAR (SEQ ID NO:2) phage over control phage. Primary cells derived from a panel of normal mouse organs also bound RPARPAR (SEQ ID NO:2) phage (FIG. 15B). In agreement with promiscuous binding, intravenously injected RPARPAR phage accumulated strongly in the first-met vascular beds: in the lungs and, to a lesser extent, the heart (FIG. 15C). In the lungs, phage immunoreactivity was seen throughout the tissue for the RPARPAR (SEQ ID NO:2) (FIG. 15D, panel d) and not control phage (FIG. 15D, panel e), which indicated that the CendR phage not only bound and was internalized by the cells lining the vessels, but was also able to penetrate into tissue parenchyma. Thus, RPARPAR (SEQ ID NO:2) peptide is an internalizing peptide that is capable of entering into various types of cells and that can also promote tissue penetration.

Figure 16A:
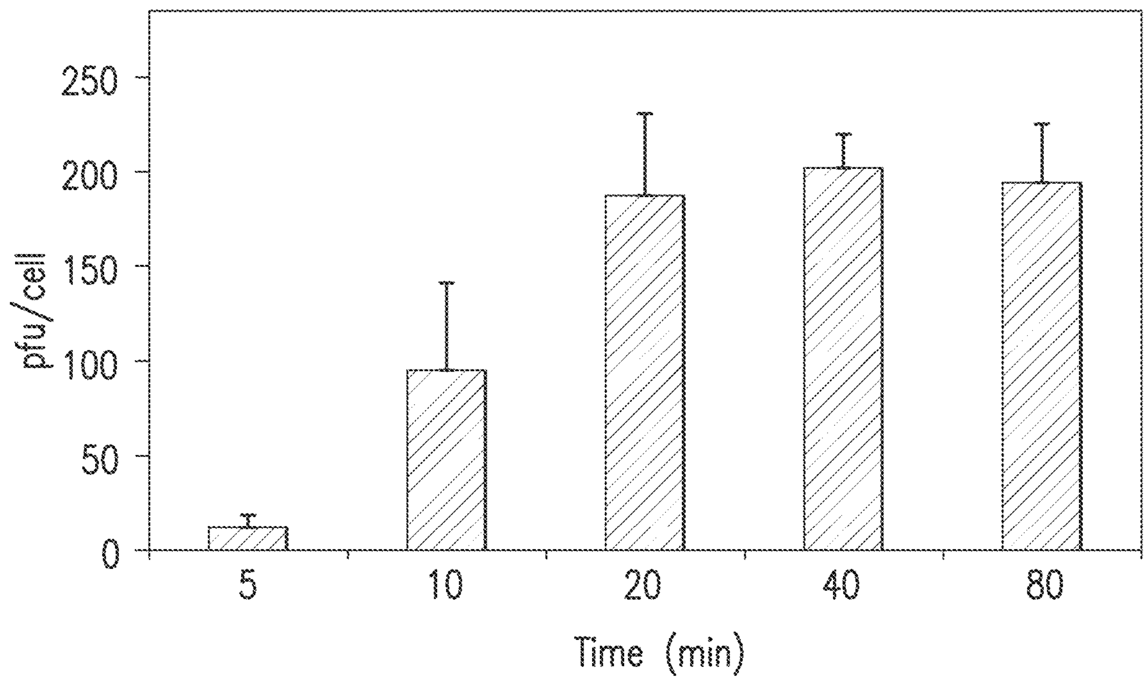
FIGS. 16A and 16B show the dynamics of binding and internalization of RPARPAR (SEQ ID NO:2) phage to the PPC-1 cells.
Figure 16B:
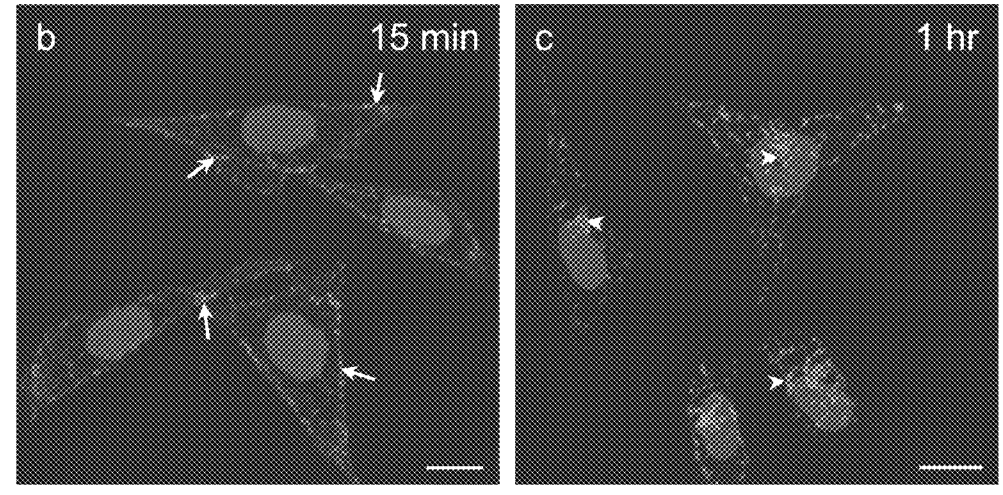

Binding of RPARPAR (SEQ ID NO:2) phage to cells at 4° C. was rapid, reaching a plateau in 20 minutes (FIG. 16A). At 37° C., RPARPAR (SEQ ID NO:2) phage and qdots showed plasma membrane association in 15 minutes and perinuclear accumulation in 1 hour after addition of the cells (FIG. 16B, panels b, c). Such qdot internalization was seen with live, unfixed cells, excluding that the intracellular accumulation was due to a processing artifact (FIG. 16B, panels b, c).

Figure 17A:
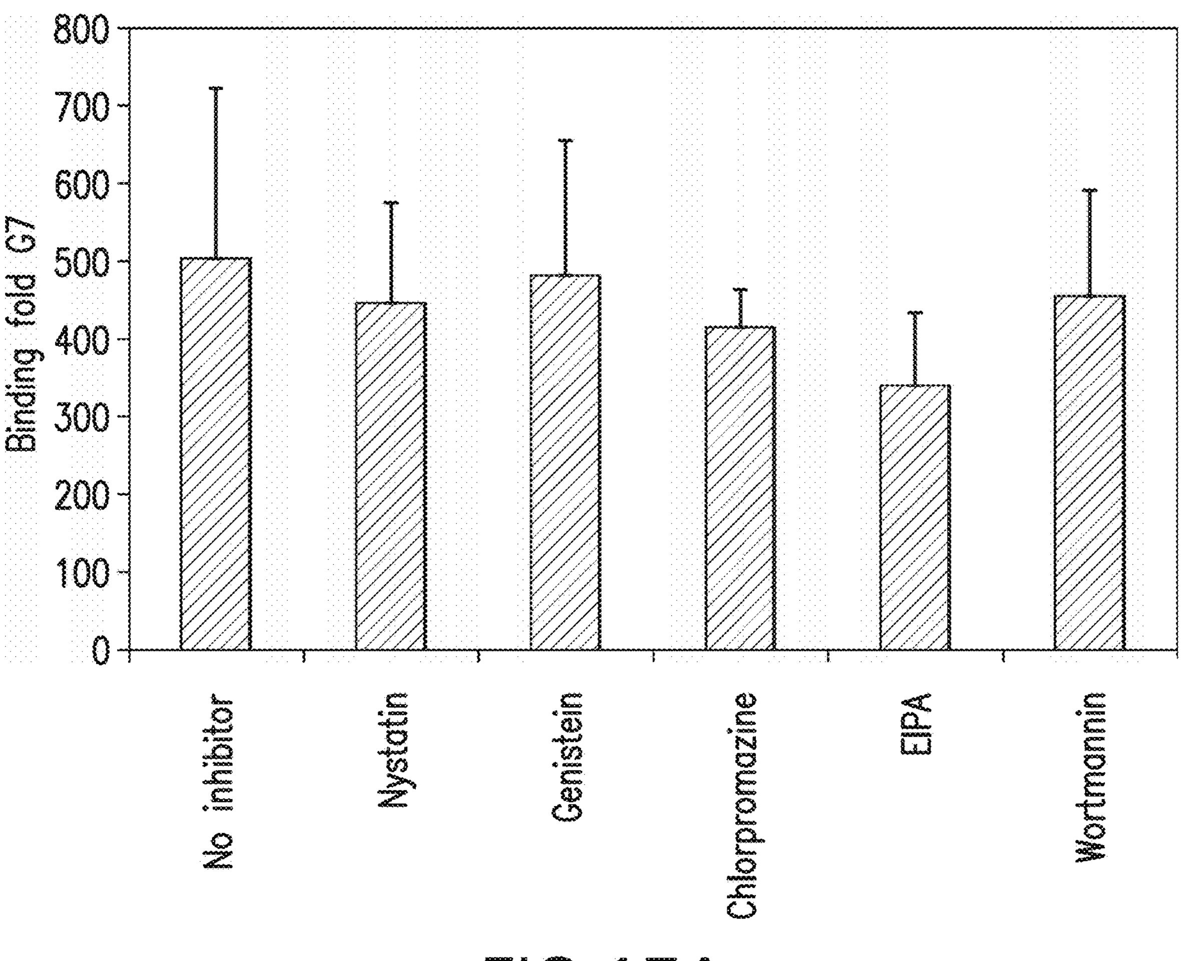
FIGS. 17A, 17B and 17C show that the RPARPAR (SEQ ID NO:2) phage is internalized by PPC-1 cells via an unconventional pathway.
Figure 17B:
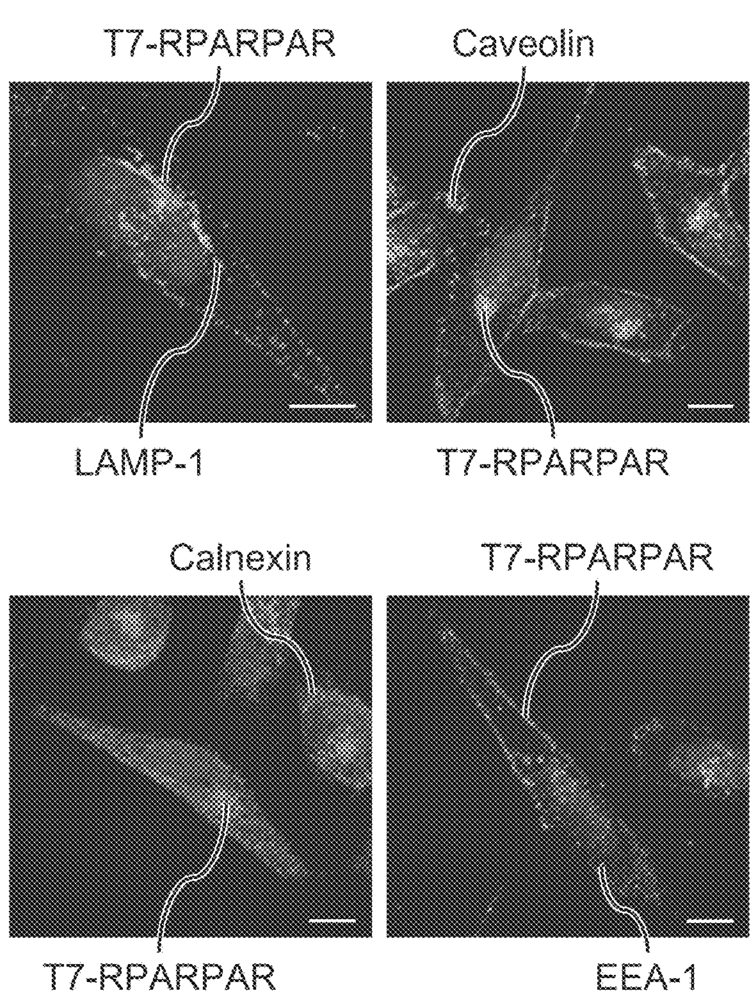
Figure 17C:
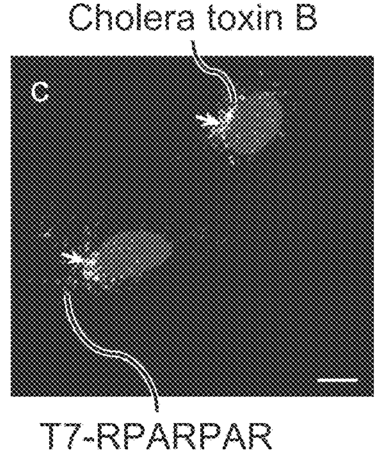

A panel of inhibitors of various endocytosis pathways was also studied: clathrin-dependent uptake (chloropromazine), caveolar endocytosis (genistein, nystatin), and macropinocytosis [5-(N-ethyl-N-isopropyl) amiloride, and wortmannin]. None of these inhibitors affected the uptake of the CendR peptides (FIG. 17A). Similarly, co-staining of internalized RPARPAR (SEQ ID NO:2) phage with a panel of subcellular compartment markers did not show any clear overlap in staining pattern (FIG. 17B). Interestingly, there was a significant overlap in the distribution of RPARPAR (SEQ ID NO:2) phage immunoreactivity and labeled cholera toxin subunit B (FIG. 17C). Although the endocytosis pathway of cholera toxin subunit B remains to be defined, it indicated to be independent of dynamin and involve both clathrin-dependent and independent mechanisms (Torgersen, M. et al. 2001).

iii. CendR Internalization is Dependent on NRP-1

Trypsin treatment of PPC-1 cells prior to binding resulted in decreased binding of RPARPAR (SEQ ID NO:2) phage particles (data not shown), indicating the involvement of a cell surface protein in the RPARPAR (SEQ ID NO:2) binding and internalization. Interaction with cell surface glycosaminoglycans is involved in internalization of cationic CPP (Tyagi, M., et al. 2001, Sandgren, S. et al. 2002). However, enzymatic digestion (heparinase III and chondroitinase ABC) and competition with heparin and chondroitin sulfate had no effect on RPARPAR (SEQ ID NO:2) phage binding to the PPC-1 cells (data not shown). To identify other potential RPARPAR (SEQ ID NO:2) interacting proteins, fractionated PPC-1 tumor xenograft extracts by affinity chromatography on the RPARPAR (SEQ ID NO:2) peptide was immobilized on agarose beads. Elution with a buffer containing free RPARPAR (SEQ ID NO: 2) peptide released a 130 kDa protein, identified by MALDI-TOF mass spectroscopy as NRP-1 (FIG. 18A).

Several lines of evidence supported the role of NRP-1 as the CendR receptor: The M21 melanoma cells, which do not bind nor internalize RPARPAR (SEQ ID NO:2), expressed trace amounts of NRP-1. Forced expression of NRP-1 rendered these cells capable of binding and internalizing RPARPAR (SEQ ID NO:2) (and not RPARPARA (SEQ ID NO: 3)) phage (FIG. 18C, panels e, f), whereas cells transfected with an NPR-1 binding pocket mutant (Vander Kooi, C. W. et al., 2007). did not confer RPARPAR (SEQ ID NO:2) binding (FIG. 18B). Finally, immunofluorescent co-staining showed that RPARPAR (SEQ ID NO: 2) phage and qdots co-localize with NRP-1 at the cell surface and inside the cells (FIG. 18C, panels c-e).

Figure 19A:
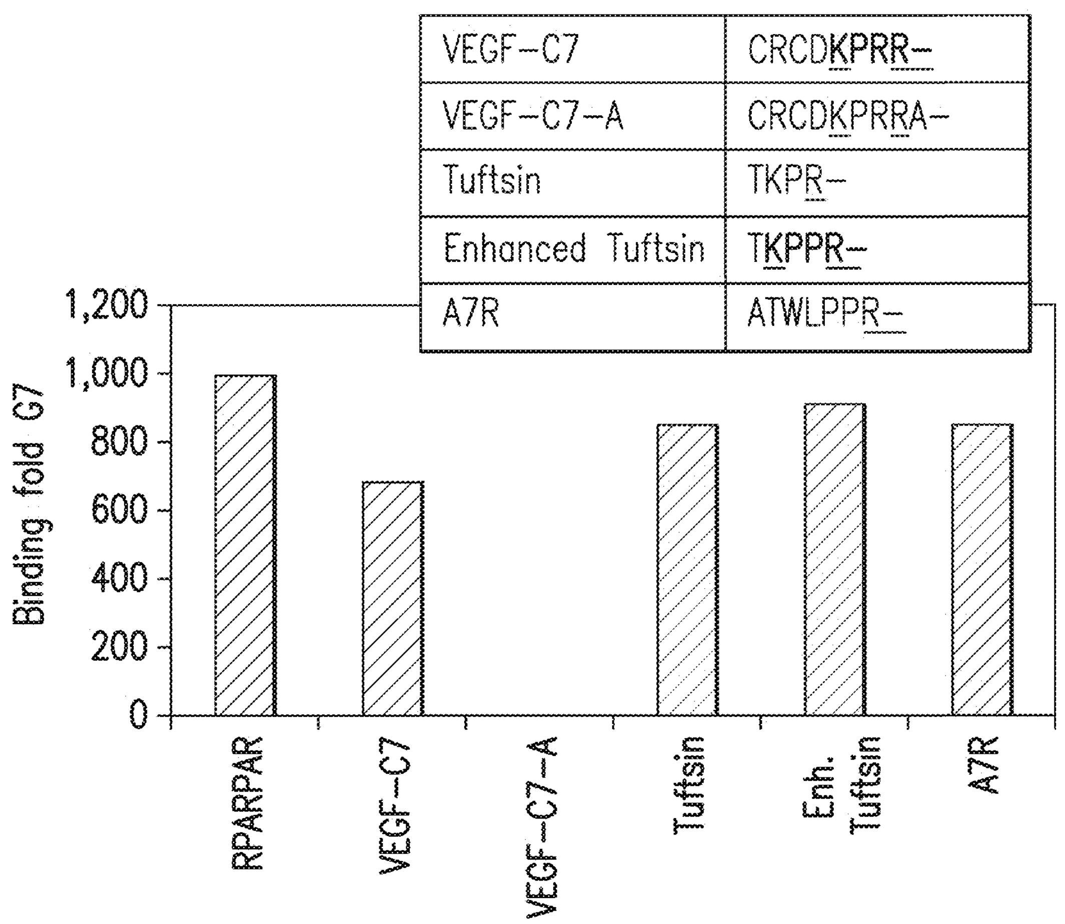
FIGS. 19A and 19B show the binding of phage displaying RPARPAR (SEQ ID NO: 2) and known NRP-1 ligand peptides to the PPC-1 cells.
Figure 19B:
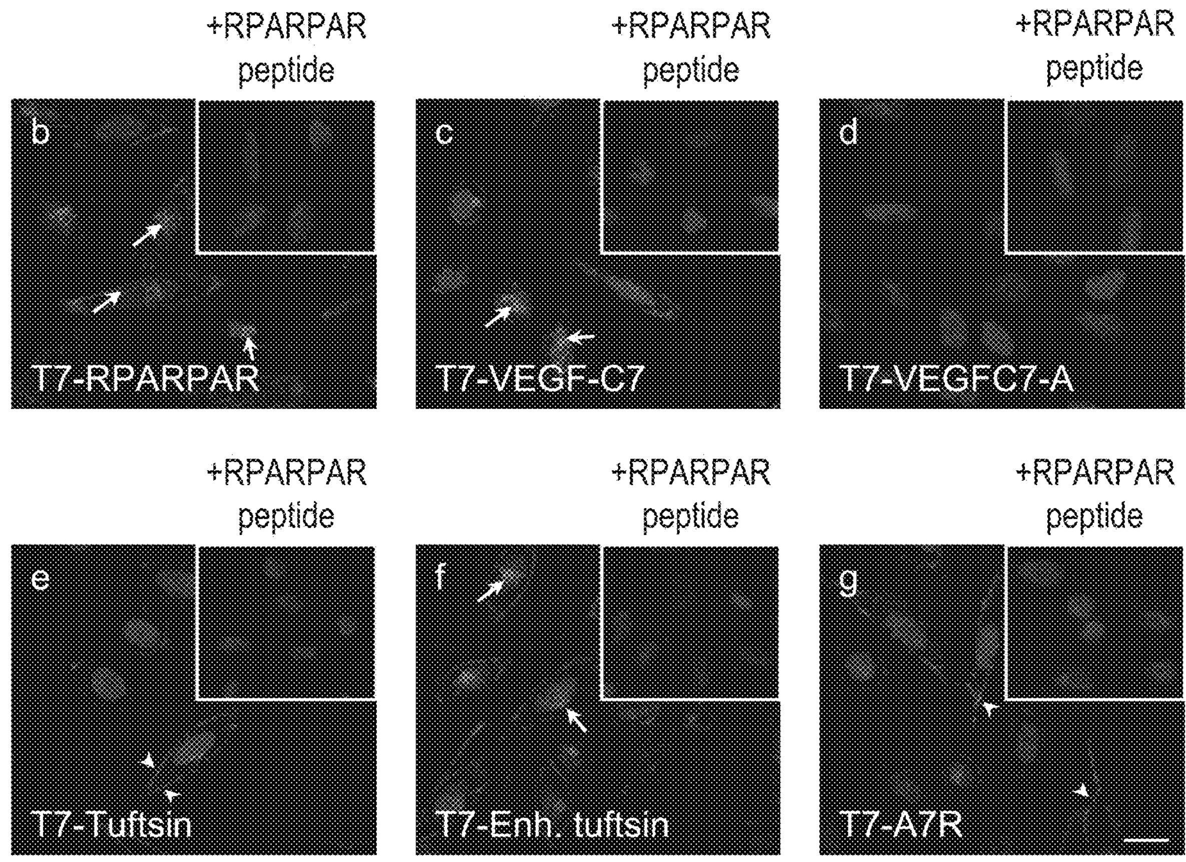

VEGF-165, binds to NRP-1 using its C-terminal CendR-like sequence encoded by exon 8 (CRCDKPRR (SEQ ID NO:30)) (Jia, H. et al. 2006, Soker, S. et al. 1998). Several other peptides such as A7R (ATWLPPR (SEQ ID NO:31)) (Starzec, A. et al. 2006), immunomodulatory peptide tuftsin (TKPR (SEQ ID NO:32)) and its variant enhanced tuftsin (TKPPR (SEQ ID NO:33)) (von Wronski, M. A. et al. 2006) bind to the same site on the NRP-1 (Geretti, E et al. 2008). T7 phage displaying seven C-terminal amino acids of VEGF-165, enhanced tuftsin or A7R bound and were taken up by PPC-1 cells, and the binding and internalization were reduced when unlabelled RPARPAR (SEQ ID NO:2) peptide was included in the binding buffer or an alanine residue was added to the C-terminus of VEGF-C7 (FIG. 19). These studies showed that CendR peptides were internalized via a pathway that involves NRP-1 as a critical component.

iv. Activation of a Cryptic CendR Motif by Proteolysis

An exciting implication of the C-end Rule is the possibility of rationally designing proteolytically activated internalizing peptides (pro-CendR). As shown above, treatment of RPARPARA (SEQ ID NO:3) phage with trypsin increased the binding of the phage to cells by more than 100 fold (FIG. 14), indicating that proteolysis can be used for unmasking of latent CendR elements. The human degradome contains more than 550 proteases (Puente, X. S. et al. 2003), many of which expose C-terminal arginine and lysine residues and do so in the context of a highly defined target sequence. Such proteases could be used to attain target cell-selective pro-CendR activation. Urokinase-type activator (uPA) is a central player in pericellular proteolysis cascades that are important in tissue remodeling during development and in pathological conditions such as tumor invasion and metastasis, neovascularization, and inflammation (Andreasen, P. A et al. 2000, Waisman, 2003). The association of uPA activity with tumors, its strong substrate selectivity, and its preference for arginine as the P1 residue, make uPA an attractive candidate for pro-CendR activation.

Figure 20A:
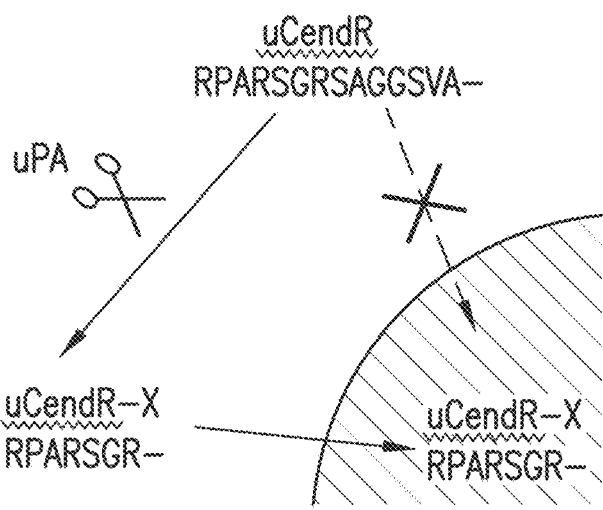
FIGS. 20A-20C show urokinase dependent CendR peptide.
Figure 20B:
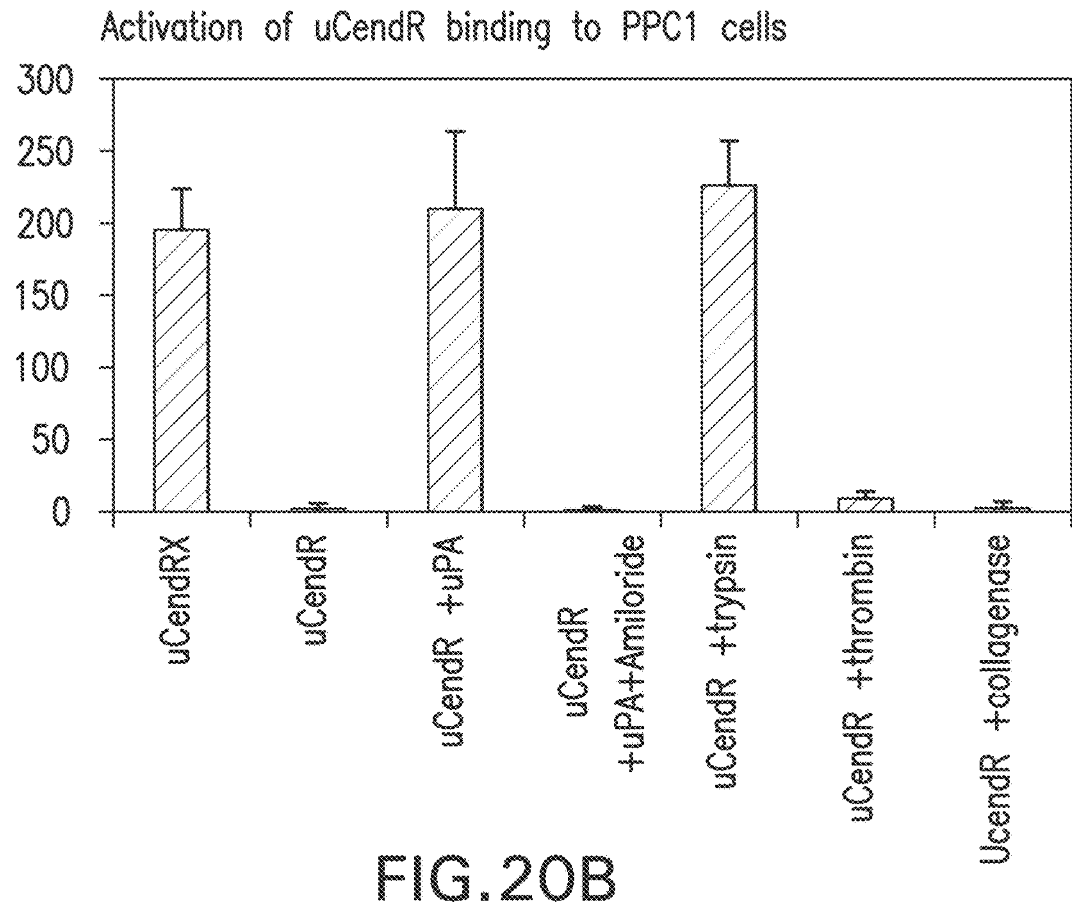
Figure 20C:
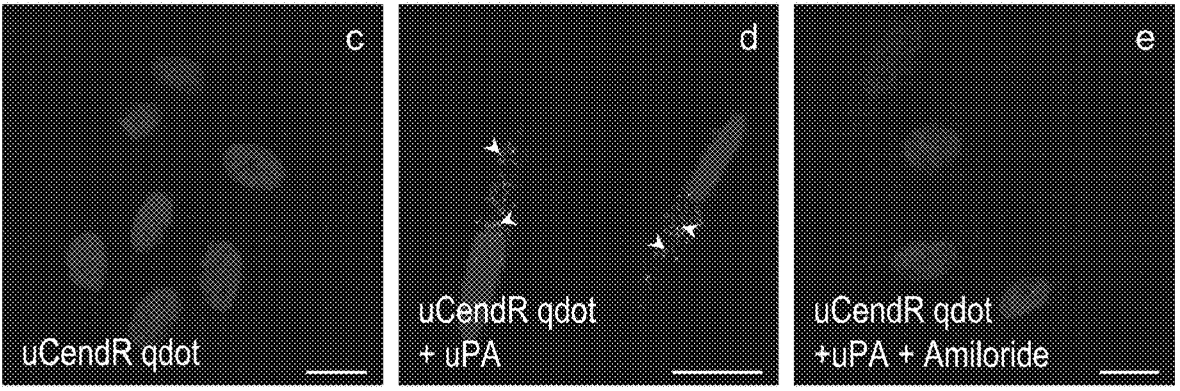

A peptide was designed that incorporates uPA recognition site (Ke, S. H. et al. 1997) and a latent CendR element (RPARSGRSAGGSVA (SEQ ID NO:34), CendR sequence italicized, FIG. 20A). Phage displaying uPA cleavable CendR (uPA-CendR) peptide did not bind to PPC-1 cells over control G7 phage, however, the binding was elevated more than 100 fold by pretreatment with uPA prior to cell binding (FIG. 20B). Qdots coated with RPARSGRSAGGSVA (SEQ ID NO:34) were also internalized in uPA sensitive fashion (FIG. 20C, panels c-e). Exposing uPA-CendR phage to trypsin greatly enhanced the binding, but phage treatment with collagenase-I or thrombin had no effect. Although thrombin cleaves after a basic residue, it apparently did not recognize the uPA substrate sequence in the peptide, whereas trypsin was sufficiently promiscuous to produce the cleavage. These studies showed that a cryptic CendR peptide can be unmasked and turned into an internalizing peptide by proteases. Moreover, a protease with restricted expression pattern can be used for target specific activation of the internalizing function of CendR peptides. Amiloride inhibited uptake (FIG. 20C, panel e).

2. Discussion

Figure 21:
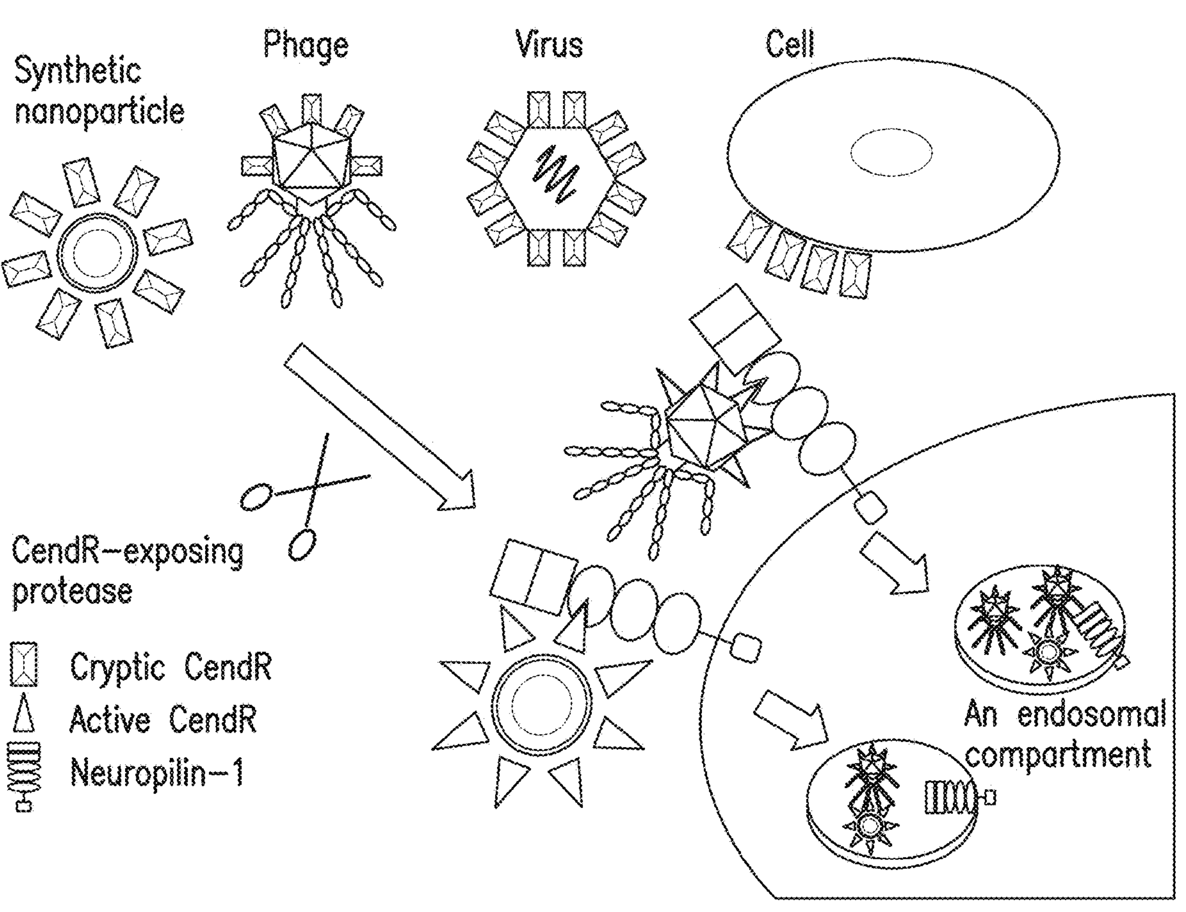
FIG. 21 shows the CendR internalization pathway. The identified internalization motif (CendR motif) that is active when positioned at the protein C-terminus. Peptides containing the CendR motif in a position other than the C-terminus (cryptic CendR peptides) are not internalized; however, their binding to neuropilin-1 and internalization can be triggered by proteolytic cleavage. The CendR pathway leads to the uptake of biological and synthetic nanoparticles (bacteriophage and qdots). CendR pathway can also be relevant to interaction of cells with other biological agents, such as viruses and other cells.

The studies reveal a previously unrecognized cellular internalization pathway, termed CendR (FIG. 21). Salient features of CendR are: (i) R/KXXR/K (SEQ ID NO:23) recognition motif, (ii) C-terminal exposure of the motif for binding and internalizing activity, (iii) NRP-1 involvement in the binding and internalization, and (iv) conversion of cryptic CendR motifs into active ones through proteolytic processing.

A group of heart-homing peptides contain an exposed CendR motif (Zhang, L. et al. 2005) but the CendR motif can also be cryptic. Several tumor-homing peptides with cell-penetrating properties contain cryptic CendR motifs (Laakkonen, P., et al. 2002b; Porkka, K. et al., 2002; Jarvinen, T. A. et al. 2007; Zhang, L. et al. 2006). In addition to the CendR motif, these peptides possess a sequence that binds to a specific receptor. An integrin-binding iRGD peptide described in (Sugahara, K. N. et al., 2008) provides an explanation of how such peptides work; the specific homing element concentrates the peptide at the target (tumor), a protease exposes the CendR motif and subsequent NRP-1 binding causes cellular uptake of the peptide (and its payload, if any).

Many of cationic CPP contain active or cryptic CendR elements (Langel, 2007). The basic domain of HIV-1 TAT protein with a CendR motif inhibits VEGFA-165 binding to NRP-1 (Jia, H. et al. 2001), but the mechanism of binding and uptake of cationic CPP is still not clear. The most important difference between cationic CPP and CendR peptides is that CCP composed of D-amino acids are active (Polyakov, V. et al. 2000, Gammon, S. T. et al. 2003), whereas the results herein show that CendR uptake is dependent on specific recognition of L-peptides only. Also, many of the CPP can internalize C-terminally anchored cargo, in clear contradiction to the core CendR concept. It is possible that CendR is one of several parallel pathways that could be involved in the uptake of cationic CPP.

The physiological significance of the CendR-mediated internalization system is not well understood, but CendR elements are present throughout the proteome, and many serine and cysteine proteases are capable of activating them (Barrett, Alan et al. 1998). Proprotein convertases and membrane proteases such as matriptase could be particularly relevant, as cleavage by these enzymes exposes an RXXR (SEQ ID NO:25) sequence at the C-terminus of various endogenous proteins (peptide hormones, growth factors, adhesion molecules, proteases) (Thomas, G., 2002, Uhland, K. 2006). Enabling the NRP-1 co-receptor function, receptor activation, and cellular uptake of active proteins are possible functions of the physiological CendR sequences.

Viruses and other micro-organisms appear to have hijacked the CendR mechanism as a facilitator of infection. Proteolytic cleavage of viral coat proteins with concomitant exposure of CendR elements appears to be a recurring theme in the infectivity of many viral pathogens (Table 2).

TABLE 2

Examples of human pathogenic viruses with surface CendR elements

| Virus | Protein | Sequence [*- cleavage] | SEQ ID NO: | Reference |
|---|---|---|---|---|
| Human cytomegalovirus | Envelope glycoprotein B (UL55) | LNITHRTRR*STSDN | 35 | Vey, M. et al., 1995 |

TABLE 2-continued

Examples of human pathogenic viruses with surface CendR elements

| Virus | Protein | Sequence [*- cleavage] | SEQ ID NO: | Reference |
|---|---|---|---|---|
| Measles virus | Fusion protein | SVASSRRHKR*FAG VV | 36 | Varsanyi, T. M., et al. 1985 |
| Tick-born encephalitis virus | PreM protein | KQEGSRTRR*SVLIP | 37 | Chambers, T. J., et al. 1990 |
| Respiratory syncytial virus | Fusion protein | PATNNRARR*ELPRF | 38 | Gonzalez-Reyes, L. et al. 2001 |
| Influenza A virus (H5N1) | Hemagglutinin | PQRERRRKKR*GLF GA | 39 | Steinhauer, D. A., 1999 |
| HIV-1 | Envelope precursor gp160 | RRVVQREKR*AVGI G | 40 | Moulard, M. et al. 2000 |
| Zaire ebolavirus | Virion spike glycoprotein precursor | LITGGRRTR*REAIV | 41 | Wool-Lewis, R. J. et al. 1999 |
| Mumps virus | Fusion protein | PSSGSRRHKR*FAGI A | 42 | Elango, N. et al. 1989 |
| Yellow fever virus | PreM protein | CDSAGRSRR*SRRAI | 43 | Ruiz-Linares, A. et al. 1989 |
| Human herpesvirus 4 | BALF4 (glycoprotein B) | AAVLRRRR*RDAGN | 44 | Johannsen, E. et al. 2004 |
| Human metapneumo-virus | Fusion glycoprotein precursor | QIENPRQSR*FVLGA | 45 | Biacchesi, S. et al., 2006 |
| Human T-lymphotropic virus-2 | Env propeptide | PPPATRRRR*AVPIA | 46 | Sjoberg, M. et al. 2006 |
| Crimean-congo hemorrhagic fever virus | Glycoprotein precursor | PSPTNRSKR*NLKME | 47 | Sanchez, A. J., et al. 2006 |

Cleavage of viral surface proteins by the ubiquitously expressed protease, furin, is an important contributing factor to the systemic spread of several viruses, whereas infectivity of viruses that are sensitive to proteases with a restricted expression pattern can limit infection to the tissues that express the appropriate protease. This concept is exemplified in influenza virus (Steinhauer, D. A. et al. 1999). Haemagglutinins of locally infective mammalian and avirulent avian-influenza viruses are cleaved at a single arginine residue; such cleavage is restricted to limited cell types, such as those of the respiratory and alimentary tracts. In contrast, virulent avian-influenza viruses that cause systemic infection are activated by furin to expose a polybasic CendR element. It is indicated herein that inhibiting CendR-mediated internalization and tissue penetration of pathogens and their products can provide a novel way of combating infectious diseases.

The CendR technology could have many other biotechnology applications, for example, improvements in the delivery of cell type-specific nanoparticle. Nanoparticles coated with pre-exposed CendR peptides would be taken up in the first vascular beds that the particles encounter (heart and lungs, after intravenous injection of RPARPAR (SEQ ID NO: 2) phage). As shown by Sugahara et al. 2008, cryptic CendR sequences could be useful in delivering cargos to peripheral tissues. Blood plasma contains high concentrations of general (e.g. alpha-2-macroglobulin) and enzyme-specific (e.g. alpha-2 antiplasmin, antithrombin) protease inhibitors. This likely provides protection against premature CendR activation in the blood. Active proteases are typically confined to the immediate pericellular area. These proteases can activate cryptic CendR peptides on nanoparticles that have reached a target tissue through passive accumulation or by homing peptide-mediated delivery. Tissue-specific proteases capable of unmasking a cryptic CendR sequence can further enhance in vivo target selectivity. The cellular uptake mediated by the activated CendR element provides a mechanism for the processed peptide and its cargo to accumulate at the target tissue or cell. Another important conclusion from the studies is that CendR elements could promote the spreading of nanoparticles in tissues, and that selective CendR mediated internalization and tissue penetration can be achieved by combining docking-based and protease-sensitive CendR targeting elements. The iRGD peptide described in the accompanying report (Sugahara et al. 2008), and possibly other internalizing vascular homing peptides with cryptic CendR elements discussed therein, illustrate this paradigm. It is also indicated that in analogy with the phage and other nanoparticles studied, various infectious agents could use the CendR system to facilitate their spreading through tissues.

3. Methods

Animal procedures. All the animal experimentation was performed using BALB/c nude mice (Harlan Sprague Dawley, Inc., Indianapolis, IN) according to procedures approved by the Animal Research Committee at University of California, Santa Barbara.

Phage display. For in vivo phage display, mice were injected intravenously with $10^{10}$ plaque-forming units (pfu) of T7 phage followed by perfusion of the circulatory system and determination of the bound phage in target organs by titration. For cell binding studies on cultured cells (in vitro display) and organ-derived cell suspensions (ex vivo display), the cells were incubated with $10^9$ pfu of phage at 4° C., washed, lysed, and quantified by titration. Incubation at 37° C. followed by low pH wash (glycine-HCl, pH 2.5) was used to assess the amount of internalized phage.

Labeling of qdots. Biotinylated peptides were used to functionalize the 605 ITK streptavidin qdots (Invitrogen, Carlsbad, CA) according to the manufacturer's instructions.

Immunofluorescence. Cultured cells and tissue sections were fixed with 4% buffered paraformaldehyde or cold (−20° C.) methanol followed by incubations with appropriate primary and Alexa-labelled secondary antibodies and nuclear staining with DAPI or Hoechst 342 DNA dyes.

Affinity chromatography. PPC-1 tumors were lysed in PBS containing 200 mM n-octyl-beta-D-glucopyranoside, followed by incubation with RPARPAR (SEQ ID NO:2)-coated Sulfolink-beads (Pierce, Rockford, IL) and elution in lysis buffer containing 2 mM free RPARPAR (SEQ ID NO:2) peptide. Gel fragments excised from silver stained gel of eluted fractions were subjected to MALDI-TOF mass spectrometry at the Burnham Institute for Medical Research Proteomics Resource.

Mice and tissues. All animal experimentation was performed according to procedures approved by the Animal Research Committee at the University of California, Santa Barbara. For tumor injections and before sacrificing, the mice were anesthetized with intraperitoneal injections of xylazine (10 mg/kg) and ketamine (50 mg/kg). BALB/c athymic nude mice (Harlan Sprague Dawley, Inc., Indianapolis, IN) were used for tumor xenografts and in vivo and ex vivo phage display experiments. Orthotopic prostate tumor xenografts were generated by injecting $10^6$ PPC-1 cells (Zhang, L. et al. 2006) into the ventral lobe of the prostate. For histological analysis, tissues were fixed in 4% paraformaldehyde, cryoprotected in phosphate buffered saline solution containing 30% sucrose, and sectioned at 10 μm.

Cell lines. PPC-1, PC-3, Du-145, 4T1, MIA PaCa-2, PDAC1.3, B16F10, M21, and MDA-MB-435 cell lines were maintained in the Dulbecco's Modified Eagle Medium (DMEM) supplemented with 10% fetal bovine serum and penicillin/streptomycin. Human umbilical vein endothelial cells were cultured according to the manufacturer's instructions.

Phage display. T7-select phage display system was used for phage library construction (library diversity—$10^8$) and individual phage cloning according the manufacturer's instructions (EMD Biosciences, Gibbstown, NJ). Phage was purified by precipitation with PEG-8000 (Sigma, St. Louis, MO) followed by $CsCl_2$ gradient ultracentrifugation and dialysis. The sequences of displayed peptides were determined from the DNA encoding the insert-containing region at the C-terminus of the T7 major coat protein gp10.

For biopanning and phage binding studies (Hoffman, J. A. et al., 2004), cultured cells were grown to confluence and harvested with trypsin and mouse organs were dissociated using Medimachine (BD Biosciences, San Jose, CA). To measure phage binding, $10^6$ cells in binding buffer (DMEM containing 1% BSA) were incubated with $10^9$ pfu/ml of T7 phage for 1 hour at 4° C. The cells were washed 4 times with the binding buffer, lysed in LB bacterial growth medium containing 1% NP-40, and titrated. Phage internalization assays used the same procedure, except that the cells were incubated with the phage at 37° C., and that an acidic buffer (500 mM sodium chloride, 0.1 M glycine, 1% BSA, pH 2.5) was used instead of binding buffer in the second wash.

Centrifugation on a silicone oil cushion (1.03 g/ml) was used to separate unbound phage from cells during time course experiments. Inhibitors of phage binding and internalization (heparin, chondroitin, glycocalyx removal enzymes, endocytosis inhibitors, free peptides, quantum dots and UV-inactivated phage) were added to the cells 20 minutes prior to incubation with phage. Endocytosis inhibitors used in this study were the following: nystatin (50 μg/ml), genistein (100 μg/ml), chlorpromazine (5 μg/ml), 5-(N-ethyl-N-isopropyl) amiloride (100 μM), wortmannin (10 μM).

In vivo phage homing studies in mice were carried out by injecting $10^{10}$ pfu of T7 phage into tail vein and 10 minutes to 1 hour later, the mice were perfused with DMEM through the left ventricle of the heart. The organs of interest were collected, homogenized in 1% NP40 and the phage was quantified by titration.

Peptide synthesis and qdot labeling. The peptides were synthesized using Fmoc/t-Bu chemistry on a microwave assisted automated peptide synthesizer (Liberty, CEM Corporation). Peptides were purified by HPLC using 0.1% TFA in acetonitrile-water mixtures to 90%-95% purity by HPLC and validated by Q-TOF mass spectral analysis.

Streptavidin ITK-605 quantum dots (Invitrogen, Carlsbad, CA) were functionalized with biotinylated peptides by incubation with 100 fold molar excess of peptide followed by removal of free peptide by dialysis.

Affinity chromatography. Orthotopic PPC-1 tumors were homgenized in PBS containing 400 mM n-octyl-beta-D-glucopyranoside, 1 mM $MgSO_4$, 1 mM $MnCl_2$, 1 mM $CaCl_2$) and 1 tablet/5 ml of EDTA-free protease inhibitors cocktail (Sigma, St. Louis, MO). After 6 hours of extraction on a rotating platform at 4° C., the lysate was cleared by centrifugation (20 minutes at 14,000 rpm in refrigerated microcentrifuge) and loaded to an affinity column prepared by coupling cysteine-tagged RPARPAR (SEQ ID NO:2) peptide to Sulfolink coupling gel according to the manufacturer's instructions (Pierce, Rockford, IL). After overnight binding, the column was washed with a column wash buffer containing 200 mM n-octyl-beta-D-glucopyranoside, but otherwise identical to the lysis buffer, followed by elution with 2 mM free RPARPAR peptide in the same buffer.

Samples of the wash and elution fractions were separated using Novex 4-20% Tris-glycine polyacrylamide gels (Invitrogen, Carlsbad, CA), silver stained using Silver Snap kit (Pierce, Rockford, IL) and subjected to MALDI-TOF mass spectrometry at the Burnham Institute for Medical Research Proteomics Facility. Affinity chromatography samples were immunoblotted and probed with antibodies followed by chemiluminescent detection of binding.

Immunofluorescence staining. Cultured cells ($2\times10^5$ cells) were grown in 6-well tissue culture plates on collagen-I coated coverslips (BD Biosciences, San Jose, CA) overnight at 37° C. in 5% $CO_2$, and incubated with $10^8$ pfu of T7 phage. The cells were fixed in 4% paraformaldehyde or cold (−20° C.) methanol, and stained with antibodies. Nuclei were stained with DAPI or Hoechst 542. A polyclonal rabbit anti-T7 antibody was generated in-house as described previously (Laakkonen, P. et al. 2002b), except that an additional phage purification step using $CsCl_2$ centrifugation was included. Other primary antibodies used were rat anti-mouse CD31 monoclonal antibody (BD Biosciences), rabbit anti-NRP-1, mouse anti-human Lamp-1, mouse anti-human caveolin (Millipore, Temecula, CA), mouse anti-NRP-1 (Miltenyi Biotec Inc., Auburn, CA), mouse anti-human EEA-1 (BD Biosciences, San Jose, CA). The secondary antibodies, Alexa594 goat antibodies to mouse, rat, and rabbit immunoglobulins and Alexa488 donkey anti-rabbit antibody were from Invitrogen (Carlsbad, CA). Cells and tissue sections were examined by confocal microscopy (Fluoview 500, Olympus America Inc., Center Valley, PA).

DNA constructs and transfection. Expression construct of the wild type NRP-1 cDNA in pcDNA3.1 (+) was a kind gift of Dr. Michael Klagsbrun. Site directed mutagenesis was used to generate triple mutation of the VEGF-165 binding site in the b1 domain of NRP-1 (S346A-E348A-349A) by replacing TCAAAAGAAACC (SEQ ID NO:48) (encoding amino acids SKET) with GCTAAAGCTGCT (SEQ ID NO:49) (encoding AKAA).

M21 melanoma cells were transiently transfected with these constructs using lipofectamine according to manufacturer's instructions (Invitrogen, Carlsbad, CA).

Protease treatment of phage and qdots. $10^9$ phage particles or 50 µl of peptide-coated qdots phage were treated with 50 iu of uPA, 25 µg of crystalline trypsin, 50 iu of thrombin, or 25 µg of collagenase type I (all Sigma, St. Louis, Mo).

Statistical analysis. Data were analyzed by students t-test and one way analysis of variance (ANOVA) followed by suitable post-hoc test (Table 3).

TABLE 3

| Statistical significance[†] | | | |
|---|---|---|---|
| FIG. | Method | p value[§] | |
| 11A | t-test, 2 tailed | ** | p = 0.0029 |
| | | ** | p = 0.0013 |
| | | * | p = 0.0135 |
| 15C | t-test, 2 tailed | ** | p = 0.0012 |
| | | *** | p = 0.0001 |
| 18B | one way ANOVA | *** | p < 0.0001 |
| | | *** | p < 0.0001 |
| | | *** | p < 0.0001 |
| 20B | one way ANOVA | *** | p < 0.0001 |
| | | *** | p < 0.0001 |
| | | *** | p < 0.0001 |
| 12A[¶] | t-test, 2 tailed | ** | p < 0.00278 |
| | | * | p < 0.01403 |
| | | ** | p < 0.00698 |

[¶]FIG. 12A.
[§]The p values correspond to the asterisks from left to right in each figure. Single asterisk, $p < 0.05$; double asterisk, $p < 0.01$; triple asterisk, $p < 0.001$.
[†]n = 3 for all statistical analyses.

Throughout this application, various publications are referenced. The disclosures of these publications in their entireties are hereby incorporated by reference into this application in order to more fully describe the state of the art to which this invention pertains.

REFERENCES

Abi-Habib R J, Liu S, Bugge T H, Leppla S H, Frankel A E. (2004) A urokinase-activated recombinant diphtheria toxin targeting the granulocyte-macrophage colony-stimulating factor receptor is selectively cytotoxic to human acute myeloid leukemia blasts. Blood. 104, 2143-8.

Akerman, M. E., Chan, W. C. W., Laakkonen, P., Bhatia, S. N., and Ruoslahti, E. (2002) Nanocrystal targeting in vivo. Proc. Natl. Acad. Sci. USA 99, 12617-12621.

Allen, J. W., Johnson, R. S., and Bhatia, S. N. (2005). Hypoxic inhibition of 3-methylcholanthrene-induced CYP1A1 expression is independent of HIF-1alpha. Toxicol Lett 155, 151-159.

Altin J G, Pagler E B. (1995) A one-step procedure for biotinylation and chemical cross-linking of lymphocyte surface and intracellular membrane-associated molecules. Anal Biochem. 224, 382-9.

Andreasen, P. A., Egelund, R., and Petersen, H. H., The plasminogen activation system in tumor growth, invasion, and metastasis. Cell. Mol. Life Sci. 57, 25-40 (2000).

Arap, W., Pasqualini, R., and Ruoslahti, E. (1998) Cancer treatment by targeted drug delivery to tumor vasculature in a mouse model. Science 279, 377-380.

Arap, W., W. Haedicke, M. Bernasconi, R. Kain, D. Rajotte, S. Krajewski, H. M. Ellerby, D. E. Bredesen, R. Pasqualini, and E. Ruoslahti, (2002) Targeting the prostate for destruction through a vascular address. Proc. Natl Acad. Sci. USA 99, 1527-1531.

Assa-Munt, N., Jia, X., Laakkonen, P., and Ruoslahti, E. (2001) Solution structures and integrin binding activities of an RGD peptide with two isomers. Biochemistry 40, 2373-2378.

Backhaus, R., Zehe, C., Wegehingel, S., Kehlenbach, A., Schwappach, B., and Nickel, W. (2004) Unconventional protein secretion: membrane translocation of FGF-2 does not require protein unfolding. J. Cell Sci. 117, 1727-1736.

Barrett, Alan J., Rawlings, Neil D., and Woessner, J. F., Handbook of proteolytic enzymes. (Academic Press, San Diego, 1998).

Bartlett, D W., Su, H., Hildebrandt, I J., Weber, W. A., Davis, ME. (2007). Impact of tumor-specific targeting on the biodistribution and efficacy of siRNA nanoparticles measured by multimodality in vivo imaging. Proc. Natl. Acad. Sci USA. 104, 15549-15554.

Biacchesi, S. et al., Modification of the trypsin-dependent cleavage activation site of the human metapneumovirus fusion protein to be trypsin independent does not increase replication or spread in rodents or nonhuman primates. J. Virol. 80, 5798-5806 (2006).

Blasi F, Carmeliet P. (2002) uPAR: a versatile signalling orchestrator. Nat Rev Mol Cell Biol. 3, 932-43.

Brewis, N. D., Phelan, A., Normand, N., Choolun, E., and O'Hare, P. (2003) Particle assembly incorporating a VP22-BH3 fusion protein, facilitating intracellular delivery, regulated release, and apoptosis. Mol. Ther. 7, 262-270.

Brown, D. and Ruoslahti, E. (2004) Metadherin, a novel cell-surface protein in breast tumors that mediates lung metastasis. Cancer Cell 5, 365-374.

Chambers, T. J., Hahn, C. S., Galler, R., and Rice, C. M., Flavivirus genome organization, expression, and replication. Annu. Rev. Microbiol. 44, 649-688 (1990).

Choi Y, McCarthy J R, Weissleder R, Tung C H. (2006) Conjugation of a photosensitizer to an oligoarginine-based cell-penetrating peptide increases the efficacy of photodynamic therapy. ChemMedChem. 1, 458-463.

Christian, S., Pilch, J., Porkka, K., Laakkonen, P., and Ruoslahti, E. (2003) Nucleolin expressed at the cell surface is a marker of endothelial cells in tumor blood vessels. J Cell Biol. 163, 871-878.

Debela M, Magdolen V, Schechter N, Valachova M, Lottspeich F, Craik C S, Choe Y, Bode W, Goettig P. (2006) Specificity profiling of seven human tissue kallikreins reveals individual subsite preferences J Biol Chem. 281, 25678-88.

Derfus, A., Chen A., Dal-Hee M., Ruoslahti, E., Bhatia, S., (2007) Targeted Quantum Dot Conjugates for siRNA Delivery Bioconjug Chem. 18, 1391-6.

Derossi D, Chassaing G, Prochiantz A. (1998) Trojan peptides: the penetratin system for intracellular delivery. Trends Cell Biol. 8, 84-7.

Deshayes S. Morris M C. Divita G. Heitz F. 2005 Interactions of primary amphipathic cell penetrating peptides with model membranes: consequences on the mechanisms of intracellular delivery of therapeutics. Current Pharmaceutical Design. 11, 3629-38. Devine, D. V. and Bradley, A. J. (1998) The complement system in liposome clearance: can complements deposition be inhibited? Adv Drug Delivery Rev 32, 19-39.

Dharap S S, Minko T. (2003) Targeted proapoptotic LHRH-BH3 peptide. Pharm Res. 20, 889-96.

Duchardt F. Fotin-Mleczek M. Schwarz H. Fischer R. Brock R. (2007) A comprehensive model for the cellular uptake of cationic cell-penetrating peptides. Traffic. 8, 848-66.

Dykxhoorn, D. M., Palliser, D., and Lieberman, J. (2006) The silent treatment: siRNAs as small molecule drugs. Gene Ther. 13, 541-552.

Elango, N., Varsanyi, T. M., Kovamees, J., and Norrby, E., The mumps virus fusion protein mRNA sequence and homology among the paramyxoviridae proteins. J. Gen. Virol. 70, 801-807 (1989).

Elliott, G. and O'Hare, P. (1997) Intercellular trafficking and protein delivery by a herpesvirus structural protein. Cell 88, 223-233.

Esmon, C. T., Cell mediated events that control blood coagulation and vascular injury. Annu. Rev. Cell. Biol. 9, 1-26 (1993).

Fenart, L. and Cecchelli R. (2003) Protein transport in cerebral endothelium. In vitro transcytosis of transferrin. Meth. Mol. Med. 89, 277-290.

Fogal, Zhang, and Ruoslahti, Mitochondrial/Cell surface protein p32/gC1qR as a molecular target in tumor cells and tumor stroma. Cancer Res. 68:7210-7218 (2008).

Frankel, A. D. and Pabo, C. O., Cellular uptake of the tat protein from human immunodeficiency virus. Cell 55, 1189-1193 (1988).

Gammon, S. T. et al., Quantitative Analysis of Permeation Peptide Complexes Labeled with Technetium-99m: Chiral and Sequence-Specific Effects on Net Cell Uptake Bioconjugate Chem. 14, 368-376 (2003).

Geier, M. R., Trigg, M. E., and Merril, C. R. (1973) Fate of bacteriophage lambda in non-immune germ-free mice. Nature 246, 221-223.

Geretti, E., Shimizu, A., and Klagsbrun, M., Neuropilin structure governs VEGF and semaphorin binding and regulates angiogenesis. Angiogenesis 11, 31-39 (2008).

Ghebrehiwet, B., Jesty, J., and Peerschke, E. I. (2002). gC1q-R/p33: structure-function predictions from the crystal structure. Immunobiology 205, 421-432.

Gonzalez-Reyes, L. et al., Cleavage of the human respiratory syncytial virus fusion protein at two distinct sites is required for activation of membrane fusion. Proc. Natl. Acad. Sci. USA 98, 9859-9864 (2001).

Gordon, V. M. et al., Proteolytic activation of bacterial toxins by eukaryotic cells is performed by furin and by additional cellular proteases. Infect. Immun. 63, 82-87 (1995).

Green, M. and Loewenstein, P. M., Autonomous functional domains of chemically synthesized human immunodeficiency virus tat trans-activator protein. Cell 55, 1179-1188 (1988).

Hansen M, Wind T, Blouse G E, Christensen A, Petersen H H, Kjelgaard S, Mathiasen L, Holtet T L, Andreasen P A. (2005) A urokinase-type plasminogen activator-inhibiting cyclic peptide with an unusual P2 residue and an extended protease binding surface demonstrates new modalities for enzyme inhibition. J Biol Chem. 280, 38424-37.

Hoffman, J. A. et al., Progressive vascular changes in a transgenic mouse model of squamous cell carcinoma. Cancer Cell 4, 383-391 (2003).

Hoffman, J. A., Giraudo E., Singh, M., Inoue, M., Porkka, K., Hanahan' D., and Ruoslahti E. (2003) Progressive vascular changes in a transgenic mouse model of squamous cell carcinoma. Cancer Cell 4, 383-391.

Hoffman, J. A., Laakkonen, P., Porkka, K., Bernasconi, M., and Ruoslahti, E. (2004) In vivo and ex vivo selections using phage-displayed libraries. In Phage Display: A Practical Approach, T. Clarkson and H. Lowman, eds. (Oxford, U.K.: Oxford University Press), Chap 10, p 171.

Hood, J. D., Bednarski, M., Frausto, R., Guccione, S., Reisfeld, R. A., Xiang, R., and Cheresh, D. A. (2002) Tumor regression by targeted gene delivery to the neovasculature. Science 296, 2404-2407.

Jain, R K. (2005) Normalization of tumor vasculature: An emerging concept in anti-angiogenic therapy. Science 307, 58-62.

Jarvinen T. and Ruoslahti E. (2007). Molecular changes in the vasculature of injured tissues. Am. J. Path. 171:702-711.

Jia, H. et al., Characterization of a bicyclic peptide neuropilin-1 (NP-1) antagonist (EG3287) reveals importance of vascular endothelial growth factor exon 8 for NP-1 binding and role of NP-1 in KDR signaling. J. Biol. Chem. 281, 13493-13502 (2006).

Jia, H. et al., Cysteine-rich and basic domain HIV-1 Tat peptides inhibit angiogenesis and induce endothelial cell apoptosis. Biochem. Biophys. Res. Commun. 283, 469-479 (2001).

Johannsen, E. et al., Proteins of purified Epstein-Barr virus. Proc. Natl. Acad. Sci. USA 101, 16286-16291 (2004).

Joliot, A., Pernelle, C., Deagostini-Bazin, H., and Prochiantz, A., Antennapedia homeobox peptide regulates neural morphogenesis. Proc. Nat.l Acad. Sci. USA 88, 1864-1868 (1991).

Joyce, J. A., Laakkonen P., Bernasconi, M., Bergers, G., Ruoslahti, E., and Hanahan, D. (2003) Stage-specific vascular markers revealed by phage display in a mouse model of pancreatic islet tumorigenesis. Cancer Cell 4, 393-403.

Ke, S. H. et al., Optimal subsite occupancy and design of a selective inhibitor of urokinase. J. Biol. Chem. 272, 20456-20462 (1997).

Kelly K A. Nahrendorf M. Yu A M. Reynolds F. Weissleder R. (2006). In vivo phage display selection yields atherosclerotic plaque targeted peptides for imaging. Molecular Imaging & Biology. 8(4):201-207.

Kerbel, R. S. and B. A. Kamen, (2004) The anti-angiogenic basis of metronomic chemotherapy. Nat Rev Cancer 4, 423-436.

Klenk H D, Garten W. (1994) Host cell proteases controlling virus pathogenicity. Trends Microbiol. 1994 2, 39-43.

Kruithof E K. (1988) Plasminogen activator inhibitors—a review. Enzyme. 40, 113-21. Laakkonen, P., Akerman, M. E., Biliran, H., Yang, M., Ferrer, F., Karpanen, T., Hoffman, R. M., and Ruoslahti, E. (2004) Antitumor activity of a homing peptide that targets tumor lymphatics and tumor cells. Proc. Natl. Acad. Sci. USA. 101, 9381-9386.

Laakkonen, P., Porkka, K., Hoffman, J. A., and Ruoslahti, E., A tumor-homing peptide with a targeting specificity related to lymphatic vessels. Nature Med. 8, 751-755 (2002b).

Laakkonen, P., Porkka, K., Hoffman, J. A., and Ruoslahti, E. (2002a) A tumor-homing peptide with a lymphatic vessel-related targeting specificity. Nature Med 8, 743-751.

Langel, Ülo, Handbook of cell-penetrating peptides, 2nd ed. (CRC/Taylor & Francis, Boca Raton, 2007).

Li, H., Sun, H., and Qian, Z. M. (2002) The role of the transferrin-transferrin-receptor system in drug delivery and targeting. Trends Pharmacol. Sci. 23, 206-209.

Li, S-D. and Huang, L. (2006). Ann N.Y. Acad. Sci. 1082, 1-8.

Liu S, Bugge T H, Leppla S H. (2001) Targeting of tumor cells by cell surface urokinase plasminogen activator-dependent anthrax toxin. J Biol Chem. 276, 17976-84.

Mae M. Langel U. (2006). Cell-penetrating peptides as vectors for peptide, protein and oligonucleotide delivery. Current Opinion in Pharmacology. 6, 509-514.

McCarthy J R. Kelly K A. Sun E Y. Weissleder R. (2007). Targeted delivery of multifunctional magnetic nanoparticles. Nanomedicine. 2, 153-167.

Meade B R. Dowdy S F. (2007). Exogenous siRNA delivery using peptide transduction domains/cell penetrating peptides. Advanced Drug Delivery Reviews. 59(2-3):134-40.

Medarova Z, Pham W, Farrar C, Petkova V, Moore A. (2007) In vivo imaging of siRNA delivery and silencing in tumors. Nat Med. 13, 372-7.

Merril, C. R., Biswas, B., Carlton, R., Jensen, N.C., Creed, G. J., Zullo, S., and Adhya, S. (1996) Long-circulating bacteriophage as antibacterial agents. Proc. Natl. Acad. Sci. USA 93, 3188-3192.

Moghimi, S. M., Hunter, A. C. & Murray, J. C. (2001). Long-circulating and target-specific nanoparticles: Theory to practice. Pharm. Rev. 53, 283-318.

Moulard, M. and Decroly, E., Maturation of HIV envelope glycoprotein precursors by cellular endoproteases. Biochim. Biophys. Acta 1469, 121-132 (2000).

Newton J R. Kelly K A. Mahmood U. Weissleder R. Deutscher S L. (2006). In vivo selection of phage for the optical imaging of PC-3 human prostate carcinoma in mice. Neoplasia (New York). 8, 772-780.

Nyberg P, Ylipalosaari M, Sorsa T, Salo T. (2006) Trypsins and their role in carcinoma growth. Exp Cell Res. 312, 1219-28.

Pakalns. T., Haverstick, K. L., Fields, G. B., McCarthy, J. B., Mooradian, D. L., and Tirrell, M. (1999) Cellular recognition of synthetic peptide amphiphiles in self-assembled monolayer films. Biomaterials. 20, 2265-2279.

Palmacci, S. and Josephson, L. (ed. Patent, U. S.) (Advanced Magnetics, Inc. (Cambridge, MA) USA, 1993).

Park, J-H., v Maltzahn G. A., Zhang, L., Schwartz, M. P., Ruoslahti, E., Bhatia, S. N., and Sailor, M. J. Magnetic iron oxide nanoworms for tumor targeting and imaging. Adv. Mater. 20:1630-1635 (2008).

Pasqualini R. Koivunen E. Ruoslahti E. (1997). Alpha v integrins as receptors for tumor targeting by circulating ligands. [see comment]. Nat. Biotech. 15, 542-546.

Pilch J, Brown D M, Komatsu M, Jarvinen T A, Yang M, Peters D, Hoffman R M, Ruoslahti E. (2006) Peptides selected for binding to clotted plasma accumulate in tumor stroma and wounds. Proc Natl Acad Sci USA. 103, 2800-4.

Pirollo K F, Rait A, Zhou Q, Hwang S H, Dagata J A, Zon G, Hogrefe R I, Palchik G, Chang E H. (2007) Materializing the potential of small interfering RNA via a tumor-targeting nanodelivery system. Cancer Res. 67, 2938-43.

Polyakov, V. et al., Novel Tat-Peptide Chelates for Direct Transduction of Technetium-99m and Rhenium into Human Cells for Imaging and Radiotherapy Bioconjugate Chem. 11, 762-771 (2000).

Poon G M, Gariepy J. (2007) Cell-surface proteoglycans as molecular portals for cationic peptide and polymer entry into cells. Biochem Soc Trans. 35,788-93.

Porkka, K. et al., A fragment of the HMGN2 protein homes to the nuclei of tumor cells and tumor endothelial cells in vivo. Proc. Natl. Acad. Sci. USA 99, 7444-7449 (2002).

Porkka, K., Laakkonen, P., Hoffman, J. A., Bernasconi, M., and Ruoslahti, E. (2002) Targeting of peptides to the nuclei of tumor cells and tumor endothelial cells in vivo. Proc. Natl. Acad. Sci. USA. 99, 7444-7449.

Puente X S, Sanchez L M, Overall C M, Lopez-Otin C. (2003) Human and mouse proteases: a comparative genomic approach. Nat Rev Genet. 4,544-58.

Rijken D C. (1995) Plasminogen activators and plasminogen activator inhibitors: biochemical aspects. Baillieres Clin Haematol. 8, 291-312.

Rubinstein, D. B., Stortchevoi, A., Boosalis, M., Ashfaq, R., Ghebrehiwet, B., Peerschke, E. I., Calvo, F., and Guillaume, T. (2004). Receptor for the globular heads of C1q (gC1q-R, p33, hyaluronan-binding protein) is preferentially expressed by adenocarcinoma cells. Int J Cancer 110, 741-750.

Ruiz-Linares, A. et al., Processing of yellow fever virus polyprotein: role of cellular proteases in maturation of the structural proteins. J. Virol. 63, 4199-4209 (1989).

Ruoslahti, E. (2002) Specialization of tumour vasculature. Nat. Rev. Cancer 2, 83-90. Sanchez, A. J., Vincent, M. J., Erickson, B. R., and Nichol, S. T., Crimean-congo hemorrhagic fever virus glycoprotein precursor is cleaved by Furin-like and SKI-1 proteases to generate a novel 38-kilodalton glycoprotein. J. Virol. 80, 514-525 (2006).

Sandgren, S., Cheng, F., and Belting, M., Nuclear targeting of macromolecular polyanions by an HIV-Tat derived peptide. Role for cell-surface proteoglycans. J. Biol. Chem. 277, 38877-38883 (2002).

Simberg D, Duza T, Park J H, Essler M, Pilch J, Zhang L, Derfus A M, Yang M, Hoffman R M, Bhatia S, Sailor M J, Ruoslahti E. (2007) Biomimetic amplification of nanoparticle homing to tumors. Proc Natl Acad Sci USA. 104, 932-936.

Sjoberg, M., Wallin, M., Lindqvist, B., and Garoff, H., Furin cleavage potentiates the membrane fusion-controlling intersubunit disulfide bond isomerization activity of leukemia virus Env. J. Virol. 80, 5540-5551 (2006).

Soker, S. et al., Neuropilin-1 is expressed by endothelial and tumor cells as an isoform-specific receptor for vascular endothelial growth factor. Cell 92, 735-745 (1998).

Sokoloff, A. V., Bock, I., Zhang, G., Sebestyen, M. G., and Wolff, J. A. (2000) The interactions of peptides with the innate immune system studied with use of T7 phage peptide display. Mol. Ther. 2, 131-139.

Sokoloff, A. V., Wong, S. C., Ludtke, J. J., Sebestyen, M. G., Subbotin, V. M., Zhang, G., Budker, T., Bachhuber, M., Sumita, Y., and Wolff, J. A. (2003) A new peptide ligand that targets particles and heterologous proteins to hepatocytes in vivo. Mol. Ther. 8, 867-872.

Starzec, A. et al., Antiangiogenic and antitumor activities of peptide inhibiting the vascular endothelial growth factor binding to neuropilin-1. Life Sci. 79, 2370-2381 (2006).

Steinhauer, D. A., Role of hemagglutinin cleavage for the pathogenicity of influenza virus. Virology 258, 1-20 (1999).

Sternlicht, M. D. and Werb, Z., How matrix metalloproteinases regulate cell behavior. Annu. Rev. Cell. Dev. Biol. 17, 463-513 (2001).

Sugahara, K. N. et al., iRGD: A tissue-penetrating peptide for tumor targeting. Submitted to Nature (2008)

Thomas, G., Furin at the cutting edge: from protein traffic to embryogenesis and disease. Nature Rev. Mol. Cell. Biol. 3, 753-766 (2002).

Torgersen, M. L., Skretting, G., van Deurs, B., and Sandvig, K., Internalization of cholera toxin by different endocytic mechanisms. J. Cell. Sci. 114, 3737-3747 (2001).

Tyagi, M., Rusnati, M., Presta, M., and Giacca, M., Internalization of HIV-1 tat requires cell surface heparan sulfate proteoglycans. J. Biol. Chem. 276, 3254-3261 (2001).

Uhland, K., Matriptase and its putative role in cancer. Cell. Mol. Life Sci. 63, 2968-2978 (2006).

Uprichard, S. L. (2005) The therapeutic potential of RNA interference. FEBS Lett. 579, 5996-6007.

Vander Kooi, C. W. et al., Structural basis for ligand and heparin binding to neuropilin B domains. Proc. Natl. Acad. Sci. USA 104, 6152-6157 (2007).

Varsanyi, T. M., Jornvall, H., and Norrby, E., Isolation and characterization of the measles virus F1 polypeptide: comparison with other paramyxovirus fusion proteins. Virology 147, 110-117 (1985).

Vey, M. et al., Proteolytic processing of human cytomegalovirus glycoprotein B (gpUL55) is mediated by the human endoprotease furin. Virology 206, 746-749 (1995).

von Wronski, M. A. et al., Tuftsin binds neuropilin-1 through a sequence similar to that encoded by exon 8 of vascular endothelial growth factor. J. Biol. Chem. 281, 5702-5710 (2006).

Wadia, J. S., and Dowdy, S. F. (2002) Protein transduction technology. Curr. Opin. Biotech. 13, 52-56.

Waisman, David Morton, Plasminogen: structure, activation, and regulation. (Kluwer Academic/Plenum Publishers, New York, 2003).

Weissleder, R., Bogdanov, A., Neuwelt, E. A. & Papisov, M. (1995). Long-circulating iron oxide for MR imaging. Adv. Drug Deliv. Rev. 16, 321-334.

Wool-Lewis, R. J. and Bates, P., Endoproteolytic processing of the ebola virus envelope glycoprotein: cleavage is not required for function. J. Virol. 73, 1419-1426 (1999).

Zhang, L. et al., Lymphatic zip codes in premalignant lesions and tumors. Cancer Res. 66, 5696-5706 (2006).

Zhang, L., Hoffman, J. A., and Ruoslahti, E., Molecular profiling of heart endothelial cells. Circulation 112, 1601-1611 (2005).

Zorko M, Langel U. (2005) Cell-penetrating peptides: mechanism and kinetics of cargo delivery. Adv Drug Deliv Rev. 57, 529-45.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

What is claimed is:

1. A method of forming an activatable CendR element, the method comprising (a) selecting an amino acid sequence for internalization into a cell, tissue penetration, or both, wherein the amino acid sequence comprises a CendR element comprising a terminal carboxyl group, (b) causing a blocking group to be covalently coupled to the terminal carboxyl group of the CendR element, wherein a bond coupling the blocking group and the CendR element is cleavable, wherein the blocking group covalently coupled to the CendR element reduces or prevents internalization into a cell, tissue penetration, or both, wherein the activatable CendR element comprises the selected amino acid sequence and the blocking group, wherein cleavage of the activatable CendR element exposes the terminal carboxyl group of the CendR element, wherein the amino acid sequence is circular, and wherein the CendR element comprises the sequence KLAK (amino acids 11-14 of SEQ ID NO:5), KPAR (amino acids 4-7 of SEQ ID NO: 114), KPER (amino acids 4-7 of SEQ ID NO:90), KPLR (amino acids 4-7 of SEQ ID NO: 63), KPRR (amino acids 5-8 of SEQ ID NO: 126), KQAR (amino acids 4-7 of SEQ ID NO: 64), KRDR (amino acids 3-6 of SEQ ID NO:89), KRER (amino acids 4-7 of SEQ ID NO:91), KTAR (amino acids 3-6 of SEQ ID NO:56), RGDK (amino acids 2-5 of SEQ ID NO:4), RPAK (amino acids 4-7 of SEQ ID NO: 112), or RTPK (amino acids 4-7 of SEQ ID NO:84).

2. The method of claim 1, wherein the activatable CendR element is a protease-activatable CendR element.

3. The method of claim 1, wherein the amino acid sequence is selected for internalization into a cell.

4. The method of claim 1, wherein the amino acid sequence is selected for tissue penetration.

5. The method of claim 1, wherein the amino acid sequence is selected for internalization into a cell and tissue penetration.

6. The method of claim 1, wherein the blocking group covalently coupled to the CendR element reduces or prevents internalization into a cell.

7. The method of claim 1, wherein the blocking group covalently coupled to the CendR element reduces or prevents tissue penetration.

8. The method of claim 1, wherein the blocking group covalently coupled to the CendR element reduces or prevents internalization into a cell and tissue penetration.

9. An activatable CendR element made by a method comprising (a) selecting an amino acid sequence for internalization into a cell, tissue penetration, or both, wherein the amino acid sequence comprises a CendR element comprising a terminal carboxyl group, (b) causing a blocking group to be covalently coupled to the to the terminal carboxyl group of the CendR element, wherein a bond coupling the blocking group and the CendR element is cleavable, wherein the blocking group covalently coupled to the CendR element reduces or prevents internalization into a cell, tissue penetration, or both, wherein the activatable CendR element comprises the selected amino acid sequence and the blocking group, wherein cleavage of the activatable CendR element exposes the terminal carboxyl group of the CendR element, and wherein the amino acid sequence is circular, and wherein the CendR element comprises the sequence KLAK (amino acids 11-14 of SEQ ID NO:5), KPAR (amino acids 4-7 of SEQ ID NO: 114), KPER (amino acids 4-7 of SEQ ID NO:90), KPLR (amino acids 4-7 of SEQ ID NO: 63), KPRR (amino acids 5-8 of SEQ ID NO: 126), KQAR (amino acids 4-7 of SEQ ID NO: 64), KRDR (amino acids 3-6 of SEQ ID NO:89), KRER (amino acids 4-7 of SEQ ID NO:91), KTAR (amino acids 3-6 of SEQ ID NO:56), RGDK (amino acids 2-5 of SEQ ID NO:4), RPAK (amino acids 4-7 of SEQ ID NO:112), or RTPK (amino acids 4-7 of SEQ ID NO:84).

10. The CendR element of claim 9, wherein the activatable CendR element is a protease-activatable CendR element.

11. The CendR element of claim 9, wherein the method further comprises, prior to step (b), selecting the bond coupling the blocking group and the terminal carboxyl group to be cleavable by a protease present in proximity to the cell.

12. The CendR element of claim 9, wherein the blocking group is coupled to the C-terminal amino acid of the CendR element.

13. The CendR element of claim 9, wherein the blocking group is coupled to an amino acid of the CendR element other than the C-terminal amino acid of the CendR element.

14. The CendR element of claim 9, wherein a cargo composition is covalently coupled or non-covalently associated with a protein or peptide comprising the selected amino acid sequence, wherein the cargo composition is coupled or associated with the protein or peptide on the N terminal side of the CendR element.

15. The CendR element of claim 9, wherein the amino acid sequence is selected for internalization into a cell.

16. The CendR element of claim 9, wherein the amino acid sequence is selected for tissue penetration.

17. The CendR element of claim 9, wherein the amino acid sequence is selected for internalization into a cell and tissue penetration.

18. The CendR element of claim 9, wherein the blocking group covalently coupled to the CendR element reduces or prevents internalization into a cell.

19. The CendR element of claim 9, wherein the blocking group covalently coupled to the CendR element reduces or prevents tissue penetration.

20. The CendR element of claim 9, wherein the blocking group covalently coupled to the CendR element reduces or prevents internalization into a cell and tissue penetration.

* * * * *